(12) United States Patent
Dinsmore et al.

(10) Patent No.: US 6,410,534 B1
(45) Date of Patent: Jun. 25, 2002

(54) INHIBITORS OF PRENYL-PROTEIN TRANSFERASE

(75) Inventors: Christopher J. Dinsmore, Schwenksville; Ian M. Bell, Harleyville; Douglas C. Beshore, Lansdale; Theresa M. Williams, Harleysville, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/347,673

(22) Filed: Jun. 29, 1999

Related U.S. Application Data

(60) Provisional application No. 60/091,596, filed on Jul. 2, 1998.

(51) Int. Cl.[7] ............. A61K 31/4188; A61P 13/12; A61P 9/10; C07D 487/08; C07D 498/08
(52) U.S. Cl. ............. 514/249; 540/457; 540/458; 540/459; 540/461; 540/468; 540/469; 540/471; 540/472; 540/476; 540/477; 514/250
(58) Field of Search ................. 540/456, 457, 540/458, 459, 461, 468, 469, 471, 472, 476, 477; 514/249, 250

(56) References Cited

U.S. PATENT DOCUMENTS 5,756,528 A 5/1998 Anthony et al. ............ 514/399

FOREIGN PATENT DOCUMENTS

| WO | WO 95/10515 | 4/1995 |
|---|---|---|
| WO | WO 96/30363 | 10/1996 |
| WO | WO 96/31111 | 10/1996 |
| WO | WO 96/31477 | 10/1996 |
| WO | WO 96/31478 | 10/1996 |
| WO | WO 97/27752 | 8/1997 |
| WO | WO 97/27852 | 8/1997 |
| WO | WO 97/27853 | 8/1997 |
| WO | WO 97/27854 | 8/1997 |
| WO | WO 97/36583 | 10/1997 |
| WO | WO 97/36584 | 10/1997 |
| WO | WO 98/11091 | 3/1998 |

OTHER PUBLICATIONS

J. Med. Chem. vol. 42 No. 19 1999 3779–3784 Williams et al "N–Arylpiperazinone Inhibitors of Farnesyltransferase: Discovery and Biological Activity".
Exp. Opin. Ther. Patents (1998) 8(5):553–569 Williams "Inhibitors of Protein Farnesylation 1998".
Exp. Opin. Ther. Patents (1999) 9(9):1263–1280 Williams "Inhibitors of protein prenylation 1999".
Nature Medicine, vol. 1, No. 8, 792–796 1995 Kohl et al "Inhibition of farnesyltransferase induces regression of mammary and salivary carcinomas in ras transgenic mice".
Proc. Natl. Acad. Sci. USA, vol. 91, 9141–9145 1994 Kohl et al "Protein farnesyltransferase inhibitors block the growth of ras–dependent tumors in nude mice".
Exp. Opin. Ther. Patents (1996) 6(12):1295–1304 Graham et al "Oncologic, Endocrine & Metabolic. Inhibitors of protein farnesylation".
Exp. Opin. Ther. Patents (1995) 5(12):1269–1285 Graham "Oncologic, Endocrine & Metabolic. Inhibitors of protein farnesylation: a new approach to cancer chemotherapy".
Cancer Research 55 5302–5309 (1995) Sepp–Lorenzino et al "A Peptidomimetic Inhibitor of Farnesyl:Protein Transferase Blocks the Anchorage–dependent and –independent Growth of Human Tumor Cell Lines".

*Primary Examiner*—Mark L. Berch
*Assistant Examiner*—Kahsey Habte
(74) *Attorney, Agent, or Firm*—David A. Muthard; Mark R. Daniel

(57) ABSTRACT

The present invention is directed to peptidomimetic macrocyclic compounds which inhibit prenyl-protein transferase and the prenylation of the oncogene protein Ras. The invention is further directed to chemotherapeutic compositions containing the compounds of this invention and methods for inhibiting prenyl-protein transferase and the prenylation of the oncogene protein Ras.

25 Claims, No Drawings

INHIBITORS OF PRENYL-PROTEIN TRANSFERASE

RELATED APPLICATION

The present patent application claims the benefits of provisional application Ser. No. 60/091,596, filed Jul. 2, 1998, which was pending on the data of the filing of the present invention.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The term prenyl-protein transferase may be used to generally refer to farnesyl-protein transferase and geranylgeranyl-protein transferase. The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit prenyl-protein transferase and thus, the post-translational prenylation of proteins. It is a further object of this invention to develop chemotherapeutic compositions containing the compounds of this invention and methods for producing the compounds of this invention.

SUMMARY OF THE INVENTION

The present invention comprises peptidomimetic macrocyclic compounds which inhibit the prenyl-protein transferase. Further contained in this invention are chemotherapeutic compositions containing these prenyl-protein transferase inhibitors and methods for their production.

The compounds of this invention are illustrated by the formula A:

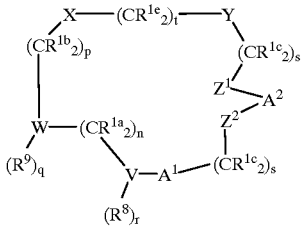

DETAILED DESCRIPTION OF THE INVENTION

The compounds of this invention are useful in the inhibition of prenyl-protein transferase and the prenylation of the oncogene protein Ras. In a first embodiment of this invention, the inhibitors of prenyl-protein transferase are illustrated by the formula A:

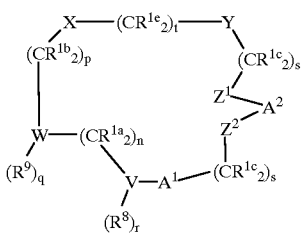

wherein:

$R^{1a}$, $R^{1b}$, $R^{1c}$, $R^{1d}$ and $R^{1e}$ are independently selected from:
  a) hydrogen,
  b) unsubstituted or substituted aryl, unsubstituted or substituted heterocycle, cycloalkyl, alkenyl, alkynyl, $R^{10}O$—, $R^{11}S(O)_m$—, $R^{10}C(O)NR^{10}$—, $(R^{10})_2N$—C(O)—, CN, NO$_2$, $(R^{10})_2N$—$C(NR^{10})$—, $R^{10}C(O)$—, $R^{10}OC(O)$—, N$_3$, -N(R^{10})_2$, or $R^{11}OC(O)NR^{10}$—,
  c) unsubstituted or substituted $C_1$–$C_6$ alkyl wherein the substitutent on the substituted $C_1$–$C_6$ alkyl is selected from unsubstituted or substituted aryl, heterocyclic, cycloalkyl, alkenyl, alkynyl, perfluoroalkyl, halogen, $R^{10}O$—, $R^4S(O)_m$—$^4S(O)_2NR^{10}$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, N$_3$, —N(R^{10})_2$, and $R^{11}OC(O)NR^{10}$—;

or two $R^{1a}$s, two $R^{1b}$s, two $R^{1c}$s, two $R^{1d}$s or two $R^{1e}$s, on the same carbon atom may be combined to form —(CH$_2$)$_v$—;

$R^4$ is selected from $C_{1-4}$ alkyl, $C_{3-6}$ cycloalkyl, heterocycle, aryl, unsubstituted or substituted with:
  a) $C_{1-4}$ alkoxy,
  b) aryl or heterocycle,
  c) halogen,
  d) HO,
  e) 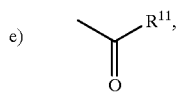
  f) —SO$_2$R$^{11}$,
  g) N(R$^{10}$)$_2$, or
  h) $C_{1-4}$ perfluoroalkyl;

$R^6$ and $R^7$ are independently selected from:
  1) hydrogen,
  2) $R^{10}C(O)$—, or $R^{10}OC(O)$—, and
  3) $C_1$–$C_6$ alkyl, $C_2$–$C_6$ alkenyl, $C_2$–$C_6$ alkynyl, $C_{3-6}$ cycloalkyl, heterocycle, aryl, aroyl, heteroaroyl, arylsulfonyl, heteroarylsulfonyl, $C_6$–$C_{10}$ multicyclic alkyl ring, unsubstituted or substituted with one or more substituents selected from:
    a) $R^{10}O$—,
    b) aryl or heterocycle,
    c) halogen,
    d) $R^{10}C(O)NR^{10}$—,
    e) 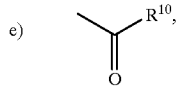
    f) —SO$_2$R$^{11}$,
    g) N(R$^{10}$)$_2$,
    h) $C_{3-6}$ cycloalkyl,
    i) $C_6$–$C_{10}$ multicyclic alkyl ring,
    j) $C_1$–$C_6$ perfluoroalkyl,
    k) $(R^{10})_2N$—$C(NR^{10})$—,
    l) $R^{10}OC(O)$—,
    m) $R^{11}OC(O)NR^{10}$—,
    n) CN, and
    o) NO$_2$; or
$R^6$ and $R^7$ may be joined in a ring;
$R^8$ is independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{12}O$—, $R^{11}S(O)_m$—, $R^{10}C(O)NR^{10}$—, $(R^{10})_2NC(O)$—, $R^{10}_2N$—$C(NR^{10})$—, CN, NO$_2$, $R^{10}C(O)$—, $R^{10}OC(O)$—, N$_3$, —N(R$^{10}$)$_2$, or $R^{11}OC(O)NR^{10}$—, and
  c) $C_1$–$C_6$ alkyl unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}_2N$—$C(NR^{10})$—, CN, $R^{10}C(O)$—, $R^{10}OC(O)$—, N$_3$, —N(R$^{10}$)$_2$, or $R^{10}OC(O)NH$—;

$R^9$ is selected from:
  a) hydrogen,
  b) $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, NO$_2$, $R^{10}C(O)$—, $R^{10}OC(O)$—, N$_3$, —N(R$^{10}$)$_2$, or $R^{11}OC(O)NR^{10}$—, and
  c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $R^{10}OC(O)$—, N$_3$, —N(R$^{10}$)$_2$, or $R^{11}OC(O)NR^{10}$—;

$R^{10}$ is independently selected from hydrogen, $C_1$–$C_6$ alkyl, unsubstituted or substituted benzyl, unsubstituted or substituted aryl and unsubstituted or substituted heterocycle;

$R^{11}$ is independently selected from $C_1$–$C_6$ alkyl unsubstituted or substituted aryl and unsubstituted or substituted heterocycle;

$R^{12}$ is independently selected from hydrogen, $C_1$–$C_6$ alkyl, $C_1$–$C_3$ perfluoroalkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is selected from a bond, —C(O)—, —C(O)$NR^{10}$—, —$NR^{10}$C(O)—, O, —N($R^{10}$)—, —S(O)$_2$N($R^{10}$)—, —N($R^{10}$)S(O)$_2$—, and S(O)$_m$;

$A^2$ is selected from a bond, —C(O)—, —C(O)$NR^{10}$—, —$R^{10}$C(O)—, O, —N($R^{10}$)—, —S(O)$_2$N($R^{10}$)—, —N($R^{10}$)S(O)$_2$—, S(O)$_m$ and —C($R^{1d}$)$_2$—;

W is heteroaryl;

V is selected from:
  a) heteroaryl, and
  b) aryl;

X and Y are independently selected from —C(O)—, —C(O)$NR^{10}$—, —$NR^{10}$C(O)—, —$NR^{10}$C(O)-O—, —O—C(O)$NR^{10}$—, —$NR^{10}$C(O)$NR^{10}$—, —C(O)$NR^{10}$C(O)—, O, —N($R^{10}$)—, —S(O)$_2$N($R^{10}$)—, —N($R^{10}$)S(O)$_2$— and S(O)$_m$;

$Z^1$ is selected from unsubstituted or substituted aryl and unsubstituted or substituted heterocycle, wherein the substituted aryl or substituted heterocycle is substituted with one or more of:
  1) $C_{1-8}$ alkyl, $C_{2-8}$ alkenyl or $C_{2-8}$ alkynyl, unsubstituted or substituted with:
    a) $C_{1-4}$ alkoxy,
    b) $NR^6R^7$,
    c) $C_{3-6}$ cycloalkyl,
    d) aryl or heterocycle,
    e) HO,
    f) —S(O)$_m$$R^4$,
    g) —C(O)$NR^6R^7$,
    h) —Si($C_{1-4}$ alkyl)$_3$, or
    i) $C_{1-4}$ perfluoroalkyl;
  2) substituted or unsubstituted aryl or substituted or unsubstituted heterocycle,
  3) halogen,
  4) $OR^6$,
  5) $NR^6R^7$,
  6) CN,
  7) $NO_2$,
  8) $CF_3$,
  9) —S(O)$_m$$R^4$,
  10) —OS(O)$_2$$R^4$,
  11) —C(O)$NR^6R^7$,
  12) —C(O)$OR^6$, or
  13) $C_3$–$C_6$ cycloalkyl;

$Z^2$ is selected from a bond, unsubstituted or substituted aryl and unsubstituted or substituted heteroaryl, wherein the substituted aryl or substituted heteroaryl is substituted with one or more of:
  1) $C_{1-8}$ alkyl, $C_{2-8}$ alkenyl or $C_{2-8}$ alkynyl, unsubstituted or substituted with:
    a) $C_{1-4}$ alkoxy,
    b) $NR^6R^7$,
    c) $C_{3-6}$ cycloalkyl,
    d) aryl or heterocycle,
    e) HO,
    f) —S(O)$_m$$R^4$,
    g) —C(O)$NR^6R^7$,
    h) —Si($C_{1-4}$ alkyl)$_3$, or
    i) $C_{1-4}$ perfluoroalkyl;
  2) substituted or unsubstituted aryl or substituted or unsubstituted heterocycle,
  3) halogen,
  4) $OR^6$,
  5) $NR^6R^7$,
  6) CN,
  7) $NO_2$,
  8) $CF_3$,
  9) —S(O)$_m$$R^4$,
  10) —OS(O)$_2$$R^4$,
  11) —C(O)$NR^6R^7$,
  12) —C(O)$OR^6$, or
  13) $C_3$–$C_6$ cycloalkyl;

m is 0, 1 or 2;
n is 0, 1, 2, 3 or 4;
p is 0, 1, 2, 3 or 4;
q is 1 or 2;
r is 0 to 5;
s is independently 0, 1, 2 or 3;
t is 1, 2, 3 or 4; and
v is 2 to 6;

or a pharmaceutically acceptable salt or stereoisomer thereof.

In a second embodiment of this invention, the inhibitors of prenyl-protein transferase are illustrated by the formula A:

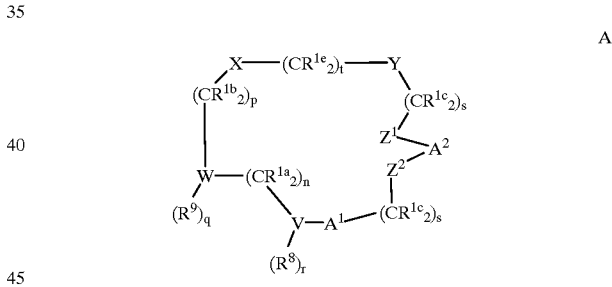

wherein:

$R^{1a}$, $R^{1b}$, $R^{1c}$, $R^{1d}$ and $R^{1e}$ are independently selected from:
  a) hydrogen,
  b) aryl, heterocycle, $C_3$–$C_{10}$ cycloalkyl, $C_2$–$C_6$ alkenyl, $C_2$–$C_6$ alkynyl, $R^{10}O$—, $R^{11}$S(O)$_m$—, $R^{10}$C(O)$NR^{10}$—, ($R^{10}$)$_2$N—C(O)—, CN, $NO_2$, ($R^{10}$)$_2$N—C($NR^{10}$)—, $R^{10}$C(O)—, $R^{10}$OC(O)—, $N_3$, —N($R^{10}$)$_2$, or $R^{11}$OC(O)$NR^{10}$—,
  c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}$S(O)$_m$—, $R^{10}$C(O)$NR^{10}$—, ($R^{10}$)$_2$N—C(O)—, CN, ($R^{10}$)$_2$N—C($NR^{10}$)—, $R^{10}$C(O)—, $R^{10}$OC(O)—, $N_3$, —N($R^{10}$)$_2$, and $R^{11}$OC(O)-$NR^{10}$—;

$R^4$ is selected from $C_{1-4}$ alkyl, $C_{3-6}$ cycloalkyl, heterocycle, aryl, unsubstituted or substituted with:
  a) $C_{1-4}$ alkoxy,
  b) aryl or heterocycle,
  c) halogen, d) HO, e) 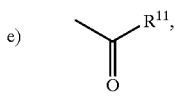

f) —SO$_2$R$^{11}$, or
g) N(R$^{10}$)$_2$;

R$^6$ and R$^7$ are independently selected from H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
  a) C$_{1-4}$ alkoxy,
  b) aryl or heterocycle,
  c) halogen,
  d) HO, e) 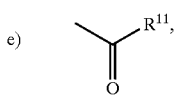

f) —SO$_2$R$^{11}$, or
  g) N(R$^{10}$)$_2$; or
R$^6$ and R$^7$ may be joined in a ring;
R$^8$ is independently selected from:
  a) hydrogen,
  b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, N$_3$, —N(R$^{10}$)$_2$, or R$^{11}$OC(O)NR$^{10}$—, and
  c) C$_1$–C$_6$ alkyl unsubstituted or substituted by unsubstituted or substituted aryl, unsubstituted or substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, R$^{10}$OC(O)—, N$_3$, —N(R$^{10}$)$_2$, or R$^{10}$OC(O)NH—;
R$^9$ is selected from:
  a) hydrogen,
  b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, N$_3$, —N(R$^{10}$)$_2$, or R$^{11}$OC(O)NR$^{10}$—, and
  c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, R$^{10}$OC(O)—, N$_3$, —N(R$^{10}$)$_2$, or R$^{11}$OC(O)NR$^{10}$—;
R$^{10}$ is independently selected from hydrogen, C$_1$–C$_6$ alkyl, benzyl, unsubstituted or substituted aryl and unsubstituted or substituted heterocycle;
R$^{11}$ is independently selected from C$_1$–C$_6$ alkyl unsubstituted or substituted aryl and unsubstituted or substituted heterocycle;
A$^1$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, and S(O)$_m$;
A$^2$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, S(O)$_m$ and —C(R$^{1d}$)$_2$—;

W is heteroaryl;
V is selected from:
  a) heteroaryl, and
  b) aryl;
X and Y are independently selected from —C(O)—, —C(O)NR$^{10}$—, —NR$^{10}$C(O)—, —NR$^{10}$C(O)-O—, —O—C(O)NR$^{10}$—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$— and S(O)$_m$;
Z$^1$ is selected from unsubstituted or substituted aryl and unsubstituted or substituted heteroaryl, wherein the substituted aryl or substituted heteroaryl is substituted with one or more of:
  1) C$_{1-4}$ alkyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^4$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$,
  9) —S(O)$_m$R$^4$,
  10) —C(O)NR$^6$R$^7$, or
  11) C$_3$–C$_6$ cycloalkyl;
Z$^2$ is selected from a bond, unsubstituted or substituted aryl and unsubstituted or substituted heteroaryl, wherein the substituted aryl or substituted heteroaryl is substituted with one or more of:
  1) C$_{1-4}$ alkyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^4$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$,
  9) —S(O)$_m$R$^4$,
  10) —C(O)NR$^6$R$^7$, or
  11) C$_3$–C$_6$ cycloalkyl;
m is 0, 1 or 2;
n is 0, 1, 2, 3 or 4;
p is 0, 1, 2, 3 or 4;
q is 1 or 2;
r is 0 to 5;
s is independently 0, 1, 2 or 3; and
t is 1, 2, 3 or 4;
or a pharmaceutically acceptable salt or stereoisomer thereof.

In a third embodiment of this invention, the inhibitors of prenyl-protein transferase are illustrated by the formula A:

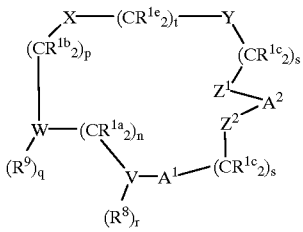

wherein:

$R^{1a}$ and $R^{1d}$ is independently selected from hydrogen and $C_1$–$C_6$ alkyl;

$R^{1b}$, $R^{1c}$ and $R^{1e}$ are independently selected from:
a) hydrogen,
b) aryl, heterocycle, cycloalkyl, $R^{10}O$—, —$N(R^{10})_2$ or $C_2$–$C_6$ alkenyl, and
c) unsubstituted or substituted $C_1$–$C_6$ alkyl wherein the substitutent on the substituted $C_1$–$C_6$ alkyl is selected from unsubstituted or substituted aryl, heterocycle, cycloalkyl, alkenyl, $R^{10}O$— and —$N(R^{10})_2$;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from H; $C_{1-4}$ alkyl, $C_{3-6}$ cycloalkyl, aryl and heterocycle, unsubstituted or substituted with:
a) $C_{1-4}$ alkoxy,
b) halogen, or
c) aryl or heterocycle;

$R^8$ is independently selected from:
a) hydrogen,
b) unsubstituted or substituted aryl, unsubstituted or substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by: unsubstituted or substituted aryl, unsubstituted or substituted heterocycle, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1$–$C_6$ alkyl, benzyl, unsubstituted or substituted aryl and unsubstituted or substituted heterocycle;

$R^{11}$ is independently selected from $C_1$–$C_6$ alkyl, unsubstituted or substituted aryl and unsubstituted or substituted heterocycle;

$A^1$ is selected from a bond, —C(O)13 , —C(O)$NR^{10}$—, —$NR^{10}C(O)$—, O, —$N(R^{10})$—, —$S(O)_2N(R^{10})$—, —$N(R^{10})S(O)_2$—, and $S(O)_m$;

$A^2$ is selected from a bond, —C(O)—, —C(O)$NR^{10}$—, —$NR^{10}C(O)$—, O, —$N(R^{10})$—, —$S(O)_2N(R^{10})$—, —$N(R^{10})S(O)_2$—, $S(O)_m$ and —$C(R^{1d})_2$—;

V is selected from:
a) heteroaryl selected from imidazolyl, pyridinyl, thiazolyl, indolyl, quinolinyl, isoquinolinyl, and thienyl, and
b) aryl;

W is a heterocycle selected from imidazolyl, pyridinyl, thiazolyl, indolyl, quinolinyl, or isoquinolinyl;

X and Y are independently selected from —C(O)—, —C(O)$NR^{10}$—, —$NR^{10}C(O)$—, —$NR^{10}C(O)NR^{10}$—, —C(O)$NR^{10}C(O)$—, O, —$N(R^{10})$—, —$S(O)_2N(R^{10})$—, —$N(R^{10})S(O)_2$—, and $S(O)_m$;

$Z^1$ is selected from unsubstituted or substituted aryl or unsubstituted or substituted heteroaryl, wherein the substituted aryl or substituted heteroaryl is independently substituted with one or two of:
1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) —$S(O)_mR^4$, or
   g) —$C(O)NR^6R^7$,
2) aryl or heterocycle,
3) halogen,
4) $OR^6$,
5) $NR^6R^7$,
6) CN,
7) $NO_2$,
8) $CF_3$,
9) —$S(O)_mR^4$,
10) —$C(O)NR^6R^7$, or
11) $C_3$–$C_6$ cycloalkyl;

$Z^2$ is selected from a bond, unsubstituted or substituted aryl and unsubstituted or substituted heteroaryl, wherein the substituted aryl or substituted heteroaryl is substituted independently with one or two of:
1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) —$S(O)_mR^4$, or
   g) —$C(O)NR^6R^7$,
2) aryl or heterocycle,
3) halogen,
4) $OR^6$,
5) $NR^6R^7$,
6) CN,
7) $NO_2$,
8) $CF_3$,
9) —$S(O)_mR^4$,
10) —$C(O)NR^6R^7$, or
11) $C_3$–$C_6$ cycloalkyl;

m is 0, 1 or 2;
n is 0, 1, 2, 3 or 4;
p is 0, 1, 2, 3 or 4;
q is 1 or 2;
r is 0 to 5;

s is independently 0, 1, 2 or 3; and
t is 1, 2, 3 or 4;
or a pharmaceutically acceptable salt or stereoisomer thereof.

In a fourth embodiment of this invention, the inhibitors of prenyl-protein transferase are illustrated by the formula B:

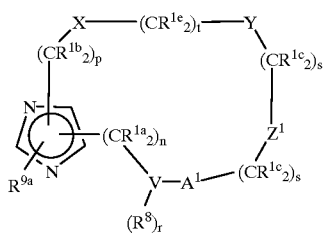

B wherein:
$R^{1a}$, $R^{1b}$ and $R^{1c}$ are independently selected from:
  a) hydrogen,
  b) aryl, heterocycle, cycloalkyl, $R^{10}O—$, $—N(R^{10})_2$ or $C_2-C_6$ alkenyl, and
  c) $C_1-C_6$ alkyl unsubstituted or substituted by aryl, heterocycle, cycloalkyl, alkenyl, $R^{10}O—$, or $—N(R^{10})_2$;

$R^{1e}$ is independently selected from:
  a) hydrogen,
  b) unsubstituted or substituted aryl, unsubstituted or substituted heterocycle, cycloalkyl, alkenyl, alkynyl, $R^{10}O—$, $R^{11}S(O)_m—$, $R^{10}C(O)NR^{10}—$, $(R^{10})_2N—C(O)—$, CN, NO$_2$, $(R^{10})_2N—C(NR^{10})—$, $R^{10}C(O)—$, $R^{10}OC(O)—$, $N_3$, $—N(R^{10})_2$, or $R^{11}OC(O)NR^{10}—$,
  c) unsubstituted or substituted $C_1-C_6$ alkyl wherein the substitutent on the substituted $C_1-C_6$ alkyl is selected from unsubstituted or substituted aryl, heterocyclic, cycloalkyl, alkenyl, alkynyl, perfluoroalkyl, halogen, $R^{10}O—$, $R^4S(O)_m—$, $R^4S(O)_2NR^{10}—$, $R^{10}C(O)NR^{10}—$, $(R^{10})_2N—C(O)—$, CN, $(R^{10})_2N—C(NR^{10})—$, $R^{10}C(O)—$, $R^{10}OC(O)—$, $N_3$, $—N(R^{10})_2$, and $R^{11}OC(O)-NR^{10}—$;

or two $R^{1e}$s, on the same carbon atom may be combined to form $—(CH_2)_v—$;

$R^4$ is selected from $C_{1-4}$ alkyl and $C_{3-6}$ cycloalkyl, unsubstituted or substituted with:
  a) $C_{1-4}$ alkoxy,
  b) halogen, or
  c) aryl or heterocycle;

$R^6$ and $R^7$ are independently selected from H; $C_{1-6}$ alkyl, $C_{3-6}$ cycloalkyl, $C_6-C_{10}$ multicyclic alkyl ring, heterocycle, aryl, aroyl, heteroaroyl, arylsulfonyl, heteroarylsulfonyl, unsubstituted or substituted with one or two:
  a) $C_{1-4}$ alkoxy,
  b) aryl or heterocycle,
  c) halogen,
  d) HO,
  e) 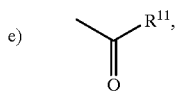

f) $—SO_2R^{11}$,
  g) $N(R^{10})_2$,
  h) $C_{3-6}$ cycloalkyl,
  i) $C_6-C_{10}$ multicyclic alkyl ring; or $R^8$ is independently selected from:
  a) hydrogen,
  b) unsubstituted or substituted aryl, $C_1-C_6$ alkyl, $C_2-C_6$ alkenyl, $C_2-C_6$ alkynyl, $C_1-C_6$ perfluoroalkyl, F, Cl, $R^{12}O—$, $R^{10}C(O)NR^{10}—$, CN, NO$_2$, $(R^{10})_2N—C(NR^{10})—$, $R^{10}C(O)—$, $—N(R^{10})_2$, or $R^{11}OC(O)NR^{10}—$, and
  c) $C_1-C_6$ alkyl substituted by: unsubstituted or substituted aryl, $C_1-C_6$ perfluoroalkyl, $R^{10}O—$, $R^{10}C(O)NR^{10}—$, $(R^{10})_2N—C(NR^{10})—$, $R^{10}C(O)—$, $—N(R^{10})_2$, or $R^{11}OC(O)NR^{10}—$;

$R^{9a}$ is hydrogen or methyl;
$R^{10}$ is independently selected from hydrogen, $C_1-C_6$ alkyl, benzyl and unsubstituted or substituted aryl;
$R^{11}$ is independently selected from $C_1-C_6$ alkyl and unsubstituted or substituted aryl;
$R^{12}$ is independently selected from hydrogen, $C_1-C_6$ alkyl, unsubstituted or substituted benzyl, unsubstituted or substituted aryl, unsubstituted or substituted heterocycle, and $C_1-C_6$ alkyl substituted with unsubstituted or substituted aryl or unsubstituted or substituted heterocycle;

$A^1$ is selected from a bond, $—C(O)-$ and O;
V is selected from:
  a) heteroaryl selected from imidazolyl, pyridinyl, thiazolyl, indolyl, quinolinyl, isoquinolinyl, and thienyl, and
  b) aryl;

X and Y are independently selected from $—C(O)—$, $—C(O)NR^{10}—$, $—NR^{10}C(O)—$, $—NR^{10}C(O)NR^{10}—$, $—C(O)NR^{10}C(O)—$, O, $—N(R^{10})—$, $—S(O)_2N(R^{10})—$, $—N(R^{10})S(O)_2—$, and $S(O)_m$;

$Z^1$ is selected from unsubstituted or substituted aryl or unsubstituted or substituted heterocycle, wherein the substituted aryl or substituted heterocycle is independently substituted with one or two of:
  1) $C_{1-8}$ alkyl, $C_{2-8}$ alkenyl or $C_{2-8}$ alkynyl, unsubstituted or substituted with:
    a) $C_{1-4}$ alkoxy,
    b) $NR^6R^7$,
    c) $C_{3-6}$ cycloalkyl,
    d) aryl or heterocycle,
    e) HO,
    f) $—S(O)_mR^4$,
    g) $—C(O)NR^6R^7$,
    h) $—Si(C_{1-4}$ alkyl$)_3$, or
    i) $C_{1-4}$ perfluoroalkyl;
  2) substituted or unsubstituted aryl or substituted or unsubstituted heterocycle,
  3) halogen,
  4) $OR^6$,
  5) $NR^6R^7$,
  6) CN,
  7) NO$_2$,
  8) CF$_3$,
  9) $—S(O)_mR^4$,
  10) $—OS(O)_2R^4$,
  11) $—C(O)NR^6R^7$,
  12) $—C(O)OR^6$, or
  13) $C_3-C_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;
or a pharmaceutically acceptable salt or stereoisomer thereof.

In a fifth embodiment of this invention, the inhibitors of prenyl-protein transferase are illustrated by the formula B:

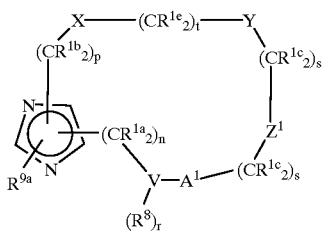

B wherein:
$R^{1a}$ and $R^{1e}$ are independently selected from hydrogen or $C_1$–$C_6$ alkyl;
$R^{1b}$ and $R^{1c}$ is independently selected from:
  a) hydrogen,
  b) aryl, heterocycle, cycloalkyl, $R^{10}O$—, —$N(R^{10})_2$ or $C_2$–$C_6$ alkenyl, and
  c) $C_1$–$C_6$ alkyl unsubstituted or substituted by aryl, heterocycle, cycloalkyl, alkenyl, $R^{10}O$—, or —$N(R^{10})_2$;
$R^4$ is selected from $C_{1-4}$ alkyl and $C_{3-6}$ cycloalkyl, unsubstituted or substituted with:
  a) $C_{1-4}$ alkoxy,
  b) halogen, or
  c) aryl or heterocycle;
$R^6$ and $R^7$ are independently selected from:
  a) hydrogen,
  b) $C_1$–$C_6$ alkyl, $C_2$–$C_6$ alkenyl, $C_2$–$C_6$ alkynyl, $R^{10}C(O)$- or $R^{10}OC(O)$- and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;
$R^8$ is independently selected from:
  a) hydrogen,
  b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by: unsubstituted or substituted aryl, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;
$R^{9a}$ is hydrogen or methyl;
$R^{10}$ is independently selected from hydrogen, $C_1$–$C_6$ alkyl, benzyl and unsubstituted or substituted aryl;
$R^{11}$ is independently selected from $C_1$–$C_6$ alkyl and unsubstituted or substituted aryl;
$A^1$ is selected from a bond, —C(O)- and O;
V is selected from:
  a) heteroaryl selected from imidazolyl, pyridinyl, thiazolyl, indolyl, quinolinyl, isoquinolinyl, and thienyl, and
  b) aryl;

X and Y are independently selected from —C(O)—, —C(O)$NR^{10}$—, —$NR^{10}C(O)$—, —$NR^{10}C(O)NR^{10}$, —C(O)$NR^{10}C(O)$—, O, —$N(R^{10})$—, —$S(O)_2N(R^{10})$—, —$N(R^{10})S(O)_2$—, and $S(O)_m$;
$Z^1$ is selected from unsubstituted or substituted aryl or unsubstituted or substituted heteroaryl, wherein the substituted aryl or substituted heteroaryl is independently substituted with one or two of:
  1) $C_{1-4}$ alkyl, unsubstituted or substituted with:
    a) $C_{1-4}$ alkoxy,
    b) $NR^6R^7$,
    c) $C_{3-6}$ cycloalkyl,
    d) aryl or heterocycle,
    e) HO,
    f) —$S(O)_mR^4$, or
    g) —$C(O)NR^6R^7$,
  2) aryl or heterocycle,
  3) halogen,
  4) $OR^6$,
  5) $NR^6R^7$,
  6) CN,
  7) $NO_2$,
  8) $CF_3$,
  9) —$S(O)_mR^4$,
  10) —$C(O)NR^6R^7$, or
  11) $C_3$–$C_6$ cycloalkyl;
m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;
or a pharmaceutically acceptable salt or stereoisomer thereof.

A preferred embodiment of the compounds of this invention is illustrated by the formula C-1:

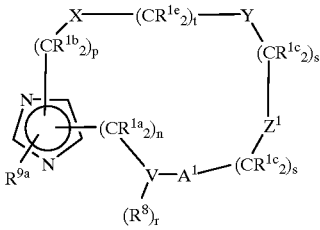

C-1 wherein:
$R^{1a}$, $R^{1b}$ and $R^{1c}$ are independently selected from:
  a) hydrogen,
  b) aryl, heterocycle, cycloalkyl, $R^{10}O$—, —$N(R^{10})_2$ or $C_2$–$C_6$ alkenyl, and
  c) $C_1$–$C_6$ alkyl unsubstituted or substituted by aryl, heterocycle, cycloalkyl, alkenyl, $R^{10}O$—, or —$N(R^{10})_2$;
$R^{1e}$ is independently selected from:
  a) hydrogen,
  b) unsubstituted or substituted aryl, unsubstituted or substituted heterocycle, cycloalkyl, alkenyl, alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, c) unsubstituted or substituted $C_1$–$C_6$ alkyl wherein the substitutent on the substituted $C_1$–$C_6$ alkyl is selected from unsubstituted or substituted aryl, heterocyclic, cycloalkyl, alkenyl, alkynyl, perfluoroalkyl, halogen, $R^{10}O$—, $R^4S(O)_m$—, $R^4S(O)_2NR^{10}$—, $R^{10}C(O)NR^{10}$—, $(R^{10})_2N$—C(O)—, CN, $(R^{10})_2N$—C($NR^{10}$)—, $R^{10}C(O)$—, $R^{10}OC(O)$—, $N_3$, —$N(R^{10})_2$, and $R^{11}OC(O)$-$NR^{10}$—;

or two $R^{1e}$s, on the same carbon atom may be combined to form —$(CH_2)_v$—;

$R^4$ is selected from $C_{1-4}$ alkyl and $C_{3-6}$ cycloalkyl, unsubstituted or substituted with:

a) $C_{1-4}$ alkoxy, b) halogen, or c) aryl or heterocycle;

$R^6$ and $R^7$ are independently selected from H; $C_{1-6}$ alkyl, $C_{3-6}$ cycloalkyl, $C_6$–$C_{10}$ multicyclic alkyl ring, heterocycle, aryl, aroyl, heteroaroyl, arylsulfonyl, heteroarylsulfonyl, unsubstituted or substituted with one or two:

a) $C_{1-4}$ alkoxy, b) aryl or heterocycle, c) halogen, d) HO, e) 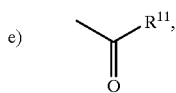

f) —$SO_2R^{11}$, g) $N(R^{10})_2$, h) $C_{3-6}$ cycloalkyl, i) $C_6$–$C_{10}$ multicyclic alkyl ring; or $R^8$ is independently selected from:

a) hydrogen, b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O$—, $R^{10}C(O)NR^{10}$—, CN, $NO_2$, $(R^{10})_2N$—C($NR^{10}$)—, $R^{10}C(O)$—, —$N(R^{10})_2$, or $R^{11}OC(O)NR^{10}$—, and c) $C_1$–$C_6$ alkyl substituted by unsubstituted or substituted aryl, $C_1$–$C_6$ perfluoroalkyl, $R^{10}O$—, $R^{10}C(O)NR^{10}$—, $(R^{10})_2N$—C($NR^{10}$)—, $R^{10}C(O)$—, —$N(R^{10})_2$, or $R^{11}OC(O)NR^{10}$—;

$R^{9a}$ is hydrogen or methyl;

$R^{10}$ is independently selected from hydrogen, $C_1$–$C_6$ alkyl, unsubstituted or substituted benzyl and unsubstituted or substituted aryl;

$R^{11}$ is independently selected from $C_1$–$C_6$ alkyl and unsubstituted or substituted aryl;

$R^{12}$ is independently selected from hydrogen, $C_1$–$C_6$ alkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is selected from a bond, —C(O)- and O;

V is phenyl or pyridyl;

X and Y are independently selected from: —C(O)—, —C(O)$NR^{10}$—, —$NR^{10}C(O)$—, —$NR^{10}C(O)NR^{10}$—, —C(O)$NR^{10}C(O)$—, O, —$N(R^{10})$—, —$S(O)_2N(R^{10})$—, —$N(R^{10})S(O)_2$—, and $S(O)_m$;

$Z^1$ is selected from unsubstituted or substituted aryl or unsubstituted or substituted heterocycle, wherein the substituted aryl or substituted heterocycle is substituted with one or two of:

1) $C_{1-8}$ alkyl, $C_{2-8}$ alkenyl or $C_{2-8}$ alkynyl, unsubstituted or substituted with:

a) $C_{1-4}$ alkoxy, b) $NR^6R^7$, c) $C_{3-6}$ cycloalkyl, d) aryl or heterocycle, e) HO, f) —$S(O)_mR^4$, g) —C(O)$NR^6R^7$, h) —Si($C_{1-4}$ alkyl)3, or i) $C_{1-4}$ perfluoroalkyl;

2) substituted or unsubstituted aryl or substituted or unsubstituted heterocycle, 3) halogen,

4) $OR^6$,

5) $NR^6R^7$,

6) CN,

7) $NO_2$,

8) $CF_3$,

9) —$S(O)_mR^4$,

10) —$OS(O)_2R^4$,

11) —C(O)$NR^6R^7$,

12) —C(O)$OR^6$, or

13) $C_3$–$C_6$ cycloalkyl;

m is 0, 1 or 2;

n is 0, 1, 2, 3 or 4;

p is 0, 1, 2, 3 or 4;

r is 0 to 5;

s is independently 0, 1, 2 or 3; and t is 1, 2, 3 or 4;

or a pharmaceutically acceptable salt or stereoisomer thereof.

Another embodiment of the compounds of this invention is illustrated by the formula C:

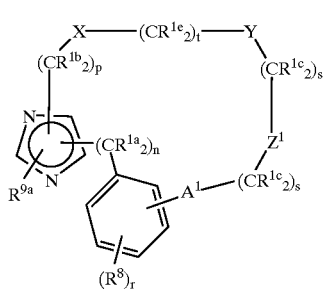

wherein:

$R^{1a}$ and $R^{1e}$ are independently selected from hydrogen and $C_1$–$C_6$ alkyl;

$R^{1b}$ and $R^{1c}$ is independently selected from:

a) hydrogen, b) aryl, heterocycle, cycloalkyl, $R^{10}O$—, —$N(R^{10})_2$ or $C_2$–$C_6$ alkenyl, and c) $C_1$–$C_6$ alkyl unsubstituted or substituted by aryl, heterocycle, cycloalkyl, alkenyl, $R^{10}O$—, or —$N(R^{10})_2$;

$R^4$ is selected from $C_{1-4}$ alkyl and $C_{3-6}$ cycloalkyl, unsubstituted or substituted with:

a) $C_{1-4}$ alkoxy,
b) halogen, or
c) aryl or heterocycle;

$R^6$ and $R^7$ are independently selected from:
a) hydrogen,
b) $C_1$–$C_6$ alkyl, $C_2$–$C_6$ alkenyl, $C_2$–$C_6$ alkynyl, $R^{10}C(O)$- or $R^{10}OC(O)$- and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by unsubstituted or substituted aryl, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;

$R^{10}$ is independently selected from hydrogen, $C_1$–$C_6$ alkyl, benzyl and unsubstituted or substituted aryl;

$R^{11}$ is independently selected from $C_1$–$C_6$ alkyl and unsubstituted or substituted aryl;

$A^1$ is selected from a bond, —C(O)- and O;

X and Y are independently selected from: —C(O)—, —C(O)$NR^{10}$—, —$NR^{10}C(O)$—, —$NR^{10}C(O)NR^{10}$—, —C(O)$NR^{10}C(O)$—, O, —$N(R^{10})$—, —$S(O)_2N(R^{10})$—, —$N(R^{10})S(O)_2$—, and $S(O)_m$;

$Z^1$ is selected from unsubstituted or substituted aryl or unsubstituted or substituted heteroaryl, wherein the substituted aryl or substituted heteroaryl is substituted with one or two of:
1) $C_{1-4}$ alkyl, unsubstituted or substituted with:
 a) $C_{1-4}$ alkoxy,
 b) $NR^6R^7$,
 c) $C_{3-6}$ cycloalkyl,
 d) aryl or heterocycle,
 e) HO,
 f) —$S(O)_mR^4$, or
 g) —$C(O)NR^6R^7$,
2) aryl or heterocycle,
3) halogen,
4) $OR^6$,
5) $NR^6R^7$,
6) CN,
7) $NO_2$,
8) $CF_3$,
9) —$S(O)_mR^4$,
10) —$C(O)NR^6R^7$, or
11) $C_3$–$C_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;

or a pharmaceutically acceptable salt or stereoisomer thereof.

In another embodiment of this invention, the inhibitors of prenyl-protein transferase are illustrated by the formula D:

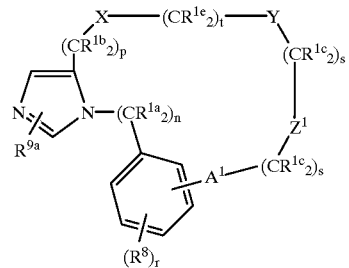

D wherein:
$R^{1a}$, $R^{1b}$ and $R^{1c}$ are independently selected from:
a) hydrogen,
b) aryl, heterocycle, cycloalkyl, $R^{10}O$—, —$N(R^{10})_2$ or $C_2$–$C_6$ alkenyl, and
c) $C_1$–$C_6$ alkyl unsubstituted or substituted by aryl, heterocycle, cycloalkyl, alkenyl, $R^{10}O$—, or —$N(R^{10})_2$;

$R^{1e}$ is independently selected from:
a) hydrogen,
b) aryl, heterocycle, cycloalkyl, alkenyl, alkynyl, $R^{10}O$—, $R^{11}S(O)_m$—, $R^{10}C(O)NR^{10}$—, $(R^{10})_2N$—C(O)—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) unsubstituted or substituted $C_1$–$C_6$ alkyl wherein the substitutent on the substituted $C_1$–$C_6$ alkyl is selected from unsubstituted or substituted aryl, heterocyclic, cycloalkyl, alkenyl, alkynyl, $R^{10}O$—, $R^{11}S(O)_m$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, $N_3$, —$N(R^{10})_2$, and $R^{11}OC(O)$-$NR^{10}$—;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from H; $C_{1-6}$ alkyl, $C_{3-6}$ cycloalkyl, $C_6$–$C_{10}$ multicyclic alkyl ring, aryl, aroyl, arylsulfonyl, unsubstituted or substituted with one or two:
a) $C_{1-4}$ alkoxy,
b) aryl,
c) halogen,
d) HO, e) 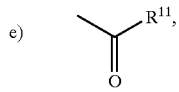

f) —$SO_2R^{11}$,
g) $N(R^{10})_2$,
h) $C_{3-6}$ cycloalkyl,
i) $C_6$–$C_{10}$ multicyclic alkyl ring; or $R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and c) $C_1$–$C_6$ alkyl substituted by unsubstituted or substituted aryl, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;

$R^{10}$ and $R^{12}$ are independently selected from hydrogen, $C_1$–$C_6$ alkyl, unsubstituted or substituted benzyl and unsubstituted or substituted aryl;

$R^{11}$ is independently selected from $C_1$–$C_6$ alkyl and unsubstituted or substituted aryl;

$A^1$ is selected from a bond, —C(O)- and O;

X and Y are independently selected from: —C(O)—, —C(O)NR$^{10}$—, —NR$^{10}$C(O)—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$—, and S(O)$_m$;

$Z^1$ is selected from unsubstituted or substituted aryl or unsubstituted or substituted heterocycle, wherein the substituted aryl or substituted heterocycle is substituted with one or two of:

1) $C_{1-8}$ alkyl, $C_{2-8}$ alkenyl or $C_{2-8}$ alkynyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) —S(O)$_m$R$^4$,
   g) —C(O)NR$^6$R$^7$,
   h) —Si(C$_{1-4}$ alkyl)$_3$, or
   i) $C_{1-4}$ perfluoroalkyl;

2) substituted or unsubstituted aryl or substituted or unsubstituted heterocycle,
3) halogen,
4) $OR^6$,
5) $NR^6R^7$,
6) CN,
7) $NO_2$,
8) $CF_3$,
9) —S(O)$_m$R$^4$,
10) —OS(O)$_2$R$^4$,
11) —C(O)NR$^6$R$^7$,
12) —C(O)OR$^6$, or
13) $C_3$–$C_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;

or a pharmaceutically acceptable salt or stereoisomer thereof.

In another embodiment of this invention, the inhibitors of prenyl-protein transferase are illustrated by the formula D:

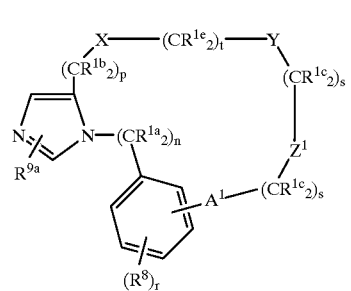

wherein:

$R^{1a}$ and $R^{1e}$ are independently selected from hydrogen and $C_1$–$C_6$ alkyl;

$R^{1b}$ and $R^{1c}$ is independently selected from:
a) hydrogen,
b) aryl, heterocycle, cycloalkyl, $R^{10}O$—, —$N(R^{10})_2$ or $C_2$–$C_6$ alkenyl, and
c) $C_1$–$C_6$ alkyl unsubstituted or substituted by aryl, heterocycle, cycloalkyl, alkenyl, $R^{10}O$—, or —$N(R^{10})_2$;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from:
a) hydrogen,
b) $C_1$–$C_6$ alkyl, $C_2$–$C_6$ alkenyl, $C_2$–$C_6$ alkynyl, $R^{10}C(O)$- or $R^{10}OC(O)$- and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—C$(NR^{10})$—, $R^{10}C(O)$—, —$N(R^{10})_2$, or $R^{11}OC(O)NR^{10}$—, and
c) $C_1$–$C_6$ alkyl substituted by unsubstituted or substituted aryl, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;

$R^{10}$ is independently selected from hydrogen, $C_1$–$C_6$ alkyl, benzyl and unsubstituted or substituted aryl;

$R^{11}$ is independently selected from $C_1$–$C_6$ alkyl and unsubstituted or substituted aryl;

$A^1$ is selected from a bond, —C(O)- and O;

X and Y are independently selected from: —C(O)—, —C(O)NR$^{10}$—, —NR$^{10}$C(O)—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$—, and S(O)$_m$;

$Z^1$ is selected from unsubstituted or substituted aryl or unsubstituted or substituted heteroaryl, wherein the substituted aryl or substituted heteroaryl is substituted with one or two of:

1) $C_{1-4}$ alkyl, unsubstituted or substituted with:
   a) $C_{1-4}$ alkoxy,
   b) $NR^6R^7$, c) $C_{3-6}$ cycloalkyl,
d) aryl or heterocycle,
e) HO,
f) —S(O)$_m$R$^4$, or
g) —C(O)NR$^6$R$^7$,
2) aryl or heterocycle,
3) halogen,
4) OR$^6$,
5) NR$^6$R$^7$,
6) CN,
7) NO$_2$,
8) CF$_3$,
9) —S(O)$_m$R$^4$,
10) —C(O)NR$^6$R$^7$, or
11) $C_3$–$C_6$ cycloalkyl;
m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;
or a pharmaceutically acceptable salt or stereoisomer thereof.

In further preferred embodiment of this invention, the inhibitors of prenyl-protein transferase are illustrated by the formula E:

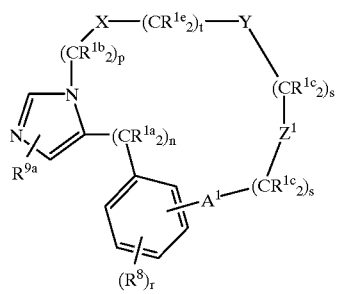

wherein:
R$^{1a}$, R$^{1b}$ and R$^{1c}$ are independently selected from:
a) hydrogen,
b) aryl, heterocycle, cycloalkyl, R$^{10}$O—, —N(R$^{10}$)$_2$ or $C_2$–$C_6$ alkenyl, and
c) $C_1$–$C_6$ alkyl unsubstituted or substituted by aryl, heterocycle, cycloalkyl, alkenyl, R$^{10}$O—, or —N(R$^{10}$)$_2$;

R$^{1e}$ is independently selected from:
a) hydrogen,
b) aryl, heterocycle, cycloalkyl, alkenyl, alkynyl, R$^{10}$O—, R$^{11}$S(O)$_m$—, R$^{10}$C(O)NR$^{10}$—, (R$^{10}$)$_2$N—C(O)—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—,
c) unsubstituted or substituted $C_1$–$C_6$ alkyl wherein the substituent on the substituted $C_1$–$C_6$ alkyl is selected from unsubstituted or substituted aryl, heterocyclic, cycloalkyl, alkenyl, alkynyl, R$^{10}$O—, R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—;

R$^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

R$^6$ and R$^7$ are independently selected from H; $C_{1-6}$ alkyl, $C_{3-6}$ cycloalkyl, $C_6$–$C_{10}$ multicyclic alkyl ring, aryl, aroyl, arylsulfonyl, unsubstituted or substituted with one or two:
a) $C_{1-4}$ alkoxy,
b) aryl,
c) halogen,
d) HO, e) 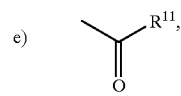

f) —SO$_2$R$^{11}$
g) N(R$^{10}$)$_2$,
h) $C_{3-6}$ cycloalkyl,
i) $C_6$–$C_{10}$ multicyclic alkyl ring; or R$^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, R$^{12}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) $C_1$–$C_6$ alkyl substituted by unsubstituted or substituted aryl, $C_1$–$C_6$ perfluoroalkyl, R$^{10}$O—, R$^{10}$C(O)NR$^{10}$—, (R$^{10}$)$_2$NC(NR$^{10}$)—, R$^{10}$C(O)—, —N(R$^{10}$)$_2$, or R$^{11}$OC(O)NR$^{10}$—;

R$^{9a}$ is hydrogen or methyl;
R$^{10}$ and R$^{12}$ are independently selected from hydrogen, $C_1$–$C_6$ alkyl, unsubstituted or substituted benzyl and unsubstituted or substituted aryl;
R$^{11}$ is independently selected from $C_1$–$C_6$ alkyl and unsubstituted or substituted aryl;
A$^1$ is selected from a bond, —C(O)— and O;
X and Y are independently selected from: —C(O)—, —C(O)NR$^{10}$—, —NR$^{10}$C(O)—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$—, and S(O)$_m$;

Z$^1$ is selected from unsubstituted or substituted aryl or unsubstituted or substituted heterocycle, wherein the substituted aryl or substituted heterocycle is substituted with one or two of:
1) $C_{1-8}$ alkyl, $C_{2-8}$ alkenyl or $C_{2-8}$ alkynyl, unsubstituted or substituted with:
a) $C_{1-4}$ alkoxy,
b) NR$^6$R$^7$,
c) $C_{3-6}$ cycloalkyl,
d) aryl or heterocycle,
e) HO,
f) —S(O)$_m$R$^4$,
g) —C(O)NR$^6$R$^7$,
h) —Si($C_{1-4}$ alkyl)$_3$, or
i) $C_{1-4}$ perfluoroalkyl;
2) substituted or unsubstituted aryl or substituted or unsubstituted heterocycle,
3) halogen,
4) OR$^6$,
5) NR$^6$R$^7$,
6) CN, 7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) C$_3$–C$_6$ cycloalkyl;

m is 0, 1 or 2;
n is 0, 1, 2, 3 or 4;
p is 0, 1, 2, 3 or 4; provided p is 2, 3 or 4 when X is —NR$^{10}$C(O)—, —NR$^{10}$C(O)NR$^{10}$—, O, —N(R$^{10}$)— or N(R$^{10}$)S(O)$_2$—;
r is 0 to 5;
s is independently 0, 1, 2 or 3; and
t is 1, 2, 3 or 4;
or a pharmaceutically acceptable salt or stereoisomer thereof.

In another embodiment of this invention, the inhibitors of prenyl-protein transferase are illustrated by the formula E:

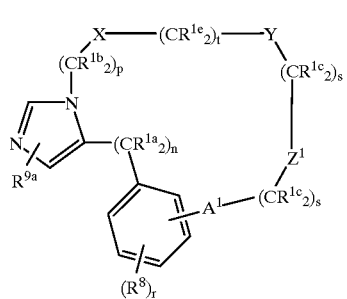

wherein:
R$^{1a}$ and R$^{1e}$ are independently selected from hydrogen and C$_1$–C$_6$ alkyl;
R$^{1b}$ and R$^{1c}$ is independently selected from:
  a) hydrogen,
  b) aryl, heterocycle, cycloalkyl, R$^{10}$O—, —N(R$^{10}$)$_2$ or C$_2$–C$_6$ alkenyl, and
  c) C$_1$–C$_6$ alkyl unsubstituted or substituted by aryl, heterocycle, cycloalkyl, alkenyl, R$^{10}$O—, or —N(R$^{10}$)$_2$;
R$^4$ is selected from C$_{1-4}$ alkyl and C$_{3-6}$ cycloalkyl, unsubstituted or substituted with:
  a) C$_{1-4}$ alkoxy,
  b) halogen, or
  c) aryl or heterocycle;
R$^6$ and R$^7$ are independently selected from:
  a) hydrogen,
  b) C$_1$–C$_6$ alkyl, C$_2$–C$_6$ alkenyl, C$_2$–C$_6$ alkynyl, R$^{10}$C(O)— or R$^{10}$OC(O)— and
  c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O) NR$^{10}$—;
R$^8$ is independently selected from:
  a) hydrogen,
  b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
  c) C$_1$–C$_6$ alkyl substituted by unsubstituted or substituted aryl, C$_1$–C$_6$ perfluoroalkyl, R$^{10}$O—, R$^{10}$C(O)NR$^{10}$—, (R$^{10}$)$_2$NC(NR$^{10}$)—, R$^{10}$C(O)—, —N(R$^{10}$)$_2$, or R$^{11}$OC(O)NR$^{10}$—;

R$^{9a}$ is hydrogen or methyl;
R$^{10}$ is independently selected from hydrogen, C$_1$–C$_6$ alkyl, benzyl and unsubstituted or substituted aryl;
R$^{11}$ is independently selected from C$_1$–C$_6$ alkyl and unsubstituted or substituted aryl;
A$^1$ is selected from a bond, —C(O)— and O;
X and Y are independently selected from —C(O)—, —C(O)NR$^{10}$—, —NR$^{10}$C(O)—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$—, and S(O)$_m$;
Z$^1$ is selected from unsubstituted or substituted aryl or unsubstituted or substituted heteroaryl, wherein the substituted aryl or substituted heteroaryl is substituted with one or two of:
  1) C$_{1-4}$ alkyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^4$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$,
  9) —S(O)$_m$R$^4$,
  10) —C(O)NR$^6$R$^7$, or
  11) C$_3$–C$_6$ cycloalkyl;

m is 0, 1 or 2;
n is 0, 1, 2, 3 or 4;
p is 0, 1, 2, 3 or 4; provided p is 2, 3 or 4 when X is —NR$^{10}$C(O)—, —NR$^{10}$C(O)NR$^{10}$—, O, —N(R$^{10}$)— or N(R$^{10}$)S(O)$_2$—;
r is 0 to 5;
s is independently 0, 1, 2 or 3; and
t is 1, 2, 3 or 4;
or a pharmaceutically acceptable salt or stereoisomer thereof.

Examples of the compounds of the invention are:
20-n-Butyl-17,18,19,20-tetrahydro-17-[2,4-dimethoxybenzyl]-18-oxo-5H-6,10:12,16-dimetheno-21H-imidazo[4,3-l][1,7,10,13]oxatriazacyclononadecine-9-carbonitrile (Compound 1)
20-n-Butyl-17,18,19,20-tetrahydro-18-oxo-5H-6,10:12,16-dimetheno-21H-imidazo[4,3-1][1,7,10,13]oxatriazacyclononadecine-9-carbonitrile, (Compound 2)
20-n-Butyl-17,18,19,20-tetrahydro-18-oxo-17-[3-(trifluoromethyl)phenyl]-5H-6,10:12,16-dimetheno-21H-imidazo[4,3-l][1,7,10,13]oxatriazacyclononadecine-9-carbonitrile (Compound 3)
19,20,21,22-Tetrahydro-19-oxo-5H-12,14-etheno-6,10-metheno-18H-benz[d]imidazo[4,3-k][1,6,9,12]oxatriazacyclooctadecine-9-carbonitrile 19,20,21,22-Tetrahydro-19-oxo-17H-6,10:12,16-dimetheno-16H-imidazo[3,4-h][1,8,11,14]oxatriazacycloeicosine-9-carbonitrile
(20R)-19,20,21,22-Tetrahydro-20-methyl-19-oxo-5H-12,14-etheno-6,10-metheno-18H-benz[d]imidazo[4,3-k][1,6,9,12]oxatriazacyclooctadecine-9-carbonitrile (20S)-19,20,21,22-Tetrahydro-20-methyl-19-oxo-5H-12,14-etheno-6,10-metheno-18H-benz[d]imidazo[4,3-k][1,6,9,12]oxatriazacyclooctadecine-9-carbonitrile (20R)-20-Benzyl-19,20,21,22-tetrahydro-19-oxo-5H-12,14-etheno-6,10-metheno-18H-benz[d]imidazo[4,3-k][1,6,9,12]oxatriazacyclo-octadecine-9-carbonitrile (20S)-20-Benzyl-19,20,21,22-tetrahydro-19-oxo-5H-12,14-etheno-6,10-metheno-18H-benz[d]imidazo[4,3-k][1,6,9,12]oxatriazacyclo-octadecine-9-carbonitrile (20R)-19,20,21,22-Tetrahydro-19-oxo-20-(3-pyridylmethyl)-5H-12,14-etheno-6,10-metheno-18H-benz[d]imidazo[4,3-k][1,6,9,12]oxatriaza-cyclooctadecine-9-carbonitrile (20R)-19,20,21,22-Tetrahydro-19-oxo-20-(thiophen-2-ylmethyl)-5H-12,14-etheno-6,10-metheno-18H-benz[d]imidazo[4,3-k][1,6,9,12]oxatriazacyclooctadecine-9-carbonitrile (20R)-19,20,22,23-Tetrahydro-20-methyl-19,22-dioxo-5H,21H-12,14-etheno-6,10-methenobenz[d]imidazo[4,3-l][1,6,9,13]oxatriazacyclononadecine-9-carbonitrile (20R)-20-Benzyl-19,20,22,23-tetrahydro-19,22-dioxo-5H,21H-12,14-etheno-6,10-methenobenz[d]imidazo[4,3-l][1,6,9,13]-oxatriazacyclononadecine-9-carbonitrile (20R)-19,20,21,22-Tetrahydro-18,20-dimethyl-19-oxo-5H-12,14-etheno-6,10-metheno-18H-benz[d]imidazo[4,3-k][1,6,9,12]oxatriaza-cyclooctadecine-9-carbonitrile (20S)-19,20,21,22-Tetrahydro-18,20-dimethyl-19-oxo-5H-12,14-etheno-6,10-metheno-18H-benz[d]imidazo[4,3-k][1,6,9,12]oxatriazacyclooctadecine-9-carbonitrile 19,20,21,22-Tetrahydro-18-methyl-19-oxo-5H-12,14-etheno-6,10-metheno-18H-benz[d]imidazo[4,3-k][1,6,9,12]oxatriaza-cyclooctadecine-9-carbonitrile 19,20,21,22-Tetrahydro-18,21-dimethyl-19-oxo-5H-12,14-etheno-6,10-metheno-18H-benz[d]imidazo[4,3-k][1,6,9,12]oxatriazacyclooctadecine-9-carbonitrile (20R)-19,20,21,22-Tetrahydro-18,20,21-trimethyl-19-oxo-5H-12,14-etheno-6,10-metheno-18H-benz[d]imidazo[4,3-k][1,6,9,12]oxatriazacyclooctadecine-9-carbonitrile (20S)-19,20,21,22-Tetrahydro-18,20,21-trimethyl-19-oxo-5H-12,14-etheno-6,10-metheno-18H-benz[d]imidazo[4,3-k][1,6,9,12]oxatriazacyclooctadecine-9-carbonitrile 19,20,21,22-Tetrahydro-21-methyl-19-oxo-5H-12,14-etheno-6,10-metheno-18H-benz[d]imidazo[4,3-k][1,6,9,12]oxatriazacyclooctadecine-9-carbonitrile (20R)-19,20,21,22-Tetrahydro-20,21-dimethyl-19-oxo-5H-12,14-etheno-6,10-metheno-18H-benz[d]imidazo[4,3-k][1,6,9,12]oxatriazacyclooctadecine-9-carbonitrile (20S)-19,20,21,22-Tetrahydro-20,21-dimethyl-19-oxo-5H-12,14-etheno-6,10-metheno-18H-benz[d]imidazo[4,3-k][1,6,9,12]oxatriazacyclooctadecine-9-carbonitrile 19,20,21,22-Tetrahydro-21-methyl-19-oxo-17H-6,10:12,16-dimetheno-16H-imidazo[3,4-h][1,8,11,14]oxatriazacycloeicosine-9-carbonitrile (20R)-20-Benzyl-19,20,21,22-tetrahydro-21-methyl-19-oxo-5H-12,14-etheno-6,10-metheno-18H-benz[d]imidazo[4,3-k][1,6,9,12]oxatriazacyclooctadecine-9-carbonitrile (20S)-20-Benzyl-19,20,21,22-tetrahydro-21-methyl-19-oxo-5H-12,14-etheno-6,10-metheno-18H-benz[d]imidazo[4,3-k][1,6,9,12]oxatriazacyclooctadecine-9-carbonitrile (20R)-20,21-Dibenzyl-19,20,21,22-tetrahydro-19-oxo-5H-12,14-etheno-6,10-metheno-18H-benz[d]imidazo[4,3-k][1,6,9,12]oxatriazacyclooctadecine-9-carbonitrile (20S)-20,21-Dibenzyl-19,20,21,22-tetrahydro-19-oxo-5H-12,14-etheno-6,10-metheno-18H-benz[d]imidazo[4,3-k][1,6,9,12]oxatriazacyclo-octadecine-9-carbonitrile 21-Benzyl-19,20,21,22-tetrahydro-19-oxo-5H-12,14-etheno-6,10-metheno-18H-benz[d]imidazo[4,3-k][1,6,9,12]oxatriazacyclo-octadecine-9-carbonitrile (20R)-21-Benzyl-19,20,21,22-tetrahydro-20-methyl-19-oxo-5H-12,14-etheno-6,10-metheno-18H-benz[d]imidazo[4,3-k][1,6,9,12]oxatriaza-cyclooctadecine-9-carbonitrile 18,19,20,21,22,23-Hexahydro-18-oxo-5H-12,14-etheno-6,10-methenobenz[d]imidazo[4,3-l][1,7,10,13]oxatriazacyclononadecine-9-carbonitrile 18,19,20,21,22,23-Hexahydro-18,21-dioxo-5H-12,14-etheno-6,10-methenobenz[d]imidazo[4,3-l][1,7,10,13]oxatriazacyclononadecine-9-carbonitrile 19,20,21,22,23,24-Hexahydro-18,23-dioxo-5H-12,14-etheno-6,10-18H-methenobenz[d]imidazo[4,3-m][1,7,10,14]oxatriazacycloeicosine-9-carbonitrile or the pharmaceutically acceptable salts thereof.

Specific example of the compounds of the instant invention include:

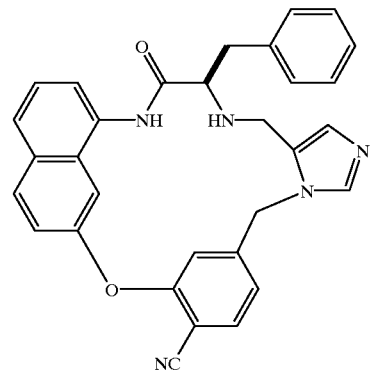

(20R)-20-Benzyl-19,20,21,22-tetrahydro-19-oxo-5H-12,14-etheno-6,10-metheno-18H-benz[d]imidazo[4,3-k][1,6,9,12]oxatriazacyclo-octadecine-9-carbonitrile

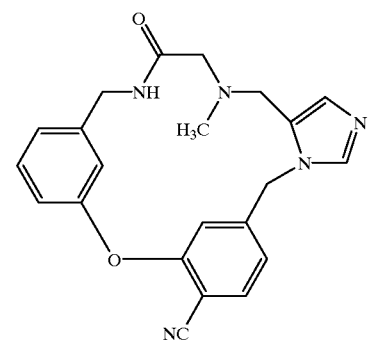

19,20,21,22-Tetrahydro-21-methyl-19-oxo-17H-6,10:12,16-dimetheno-16H-imidazo[3,4-h][1,8,11,14]oxatriazacycloeicosine-9-carbonitrile

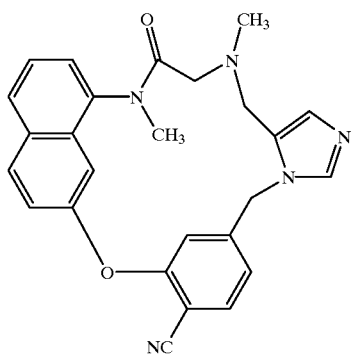

19,20,21,22-Tetrahydro-18,21-dimethyl-19-oxo-5H-12,14-etheno-6,10-metheno-18H-benz[d]imidazo[4,3-k][1,6,9,12]oxatriazacyclo-octadecine-9-carbonitrile

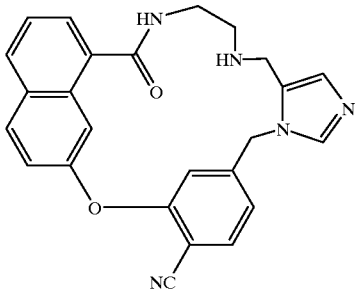

18,19,20,21,22,23-Hexahydro-18-oxo-5H-12,14-etheno-6,10-methenobenz[d]imidazo[4,3-1][1,7,10,13]oxatriazacyclononadecine-9-carbonitrile or a pharmaceutically acceptable salt or stereoisomer thereof.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Sterochemistry of Carbon Compounds* (John Wiley and Sons, New York 1994), in particular pages 1119–1190) When any variable (e.g. aryl, heterocycle, $R^{1a}$, $R^6$ etc.) occurs more than one time in any constituent, its definition on each occurrence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

Preferably, alkenyl is $C_2$–$C_6$ alkenyl.
Preferably, alkynyl is $C_2$–$C_6$ alkynyl.
As used herein, "cycloalkyl" is intended to include cyclic saturated aliphatic hydrocarbon groups having the specified number of carbon atoms. Preferably, cycloalkyl is $C_3$–$C_{10}$ cycloalkyl. Examples of such cycloalkyl elements include, but are not limited to, cyclopropyl, cyclobutyl, cyclopentyl, cyclohexyl and cycloheptyl.

As used herein, the terms "$C_6$–$C_{10}$ multicyclic alkyl ring" and "$C_6$–$C_{10}$ multicyclic ring" are intended to include polycyclic saturated and unsaturated aliphatic hydrocarbon groups having the specified number of carbon atoms. Examples of such multicyclic ring groups includes, but are not limited to:

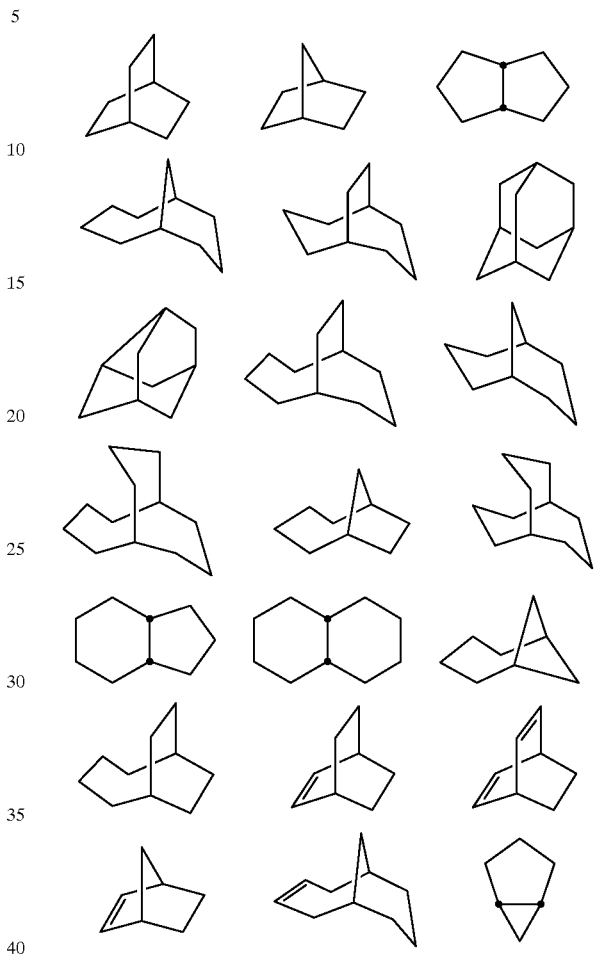

Preferably, $C_6$–$C_{10}$ multicyclic alkyl ring is adamantyl.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic, as used herein, includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein, unless otherwise specifically defined, substituted alkyl, substituted cycloalkyl, substituted aroyl, substituted aryl, substituted heteroaroyl, substituted heteroaryl, substituted arylsulfonyl, substituted heteroarylsulfonyl and substituted heterocycle include moieties containing from 1 to 3 substituents in addition to the point of attachment to the rest of the compound. Preferably, such substituents are selected from the group which includes but is not limited to F, Cl, Br, CF3, NH2, N(C1–C6 alkyl)2, NO2, CN, (C1–C6 alkyl)O—, (aryl)O—, —OH, (C1–C6 alkyl)S(O)m—, (C1–C6 alkyl)C(O)NH—, H2N—C(NH)—, (C1–C6 alkyl)C(O)—, (C1–C6 alkyl)OC(O)—, N3, (C1–C6 alkyl)OC(O)NH—, phenyl, pyridyl, imidazolyl, oxazolyl, isoxazolyl, thiazolyl, thienyl, furyl, isothiazolyl and C1–C20 alkyl.

Preferably, as used herein in the definition of $R^6$ and $R^7$, the substituted $C_{1-6}$ alkyl, substituted $C_{2-6}$ alkenyl, substituted $C_{2-6}$ alkynyl, substituted $C_{3-6}$ cycloalkyl, substituted aroyl, substituted aryl, substituted heteroaroyl, substituted arylsulfonyl, substituted heteroarylsulfonyl, substituted heterocycle and substituted $C_{6-10}$ multicyclic alkyl ring, include moieties containing from 1 to 3 substitutents in addition to the point of attachment to the rest of the compound.

The moiety formed when, in the definition of $R^{1a}$, $R^{1b}$, $R^{1c}$, $R^{1d}$ and $R^{1e}$, two $R^{1a}$s, two $R^{1b}$s, two $R^{1c}$s, two $R^{1d}$s or two $R^{1e}$s, on the same carbon atom are combined to form —(CH$_2$)$_v$— is illustrated by the following:

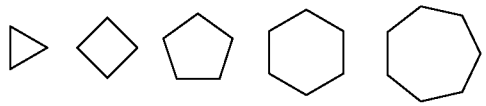

Lines drawn into the ring systems from substituents (such as from $R^8$, $R^9$ etc.) indicate that the indicated bond may be attached to any of the substitutable ring carbon atoms.

Preferably, $R^{1a}$ and $R^{1b}$ are independently selected from: hydrogen, —N(R$^{10}$)$_2$, R$^{10}$C(O)NR$^{10}$— or unsubstituted or substituted $C_1$–$C_6$ alkyl wherein the substituent on the substituted $C_1$–$C_6$ alkyl is selected from unsubstituted or substituted phenyl, —N(R$^{10}$)$_2$, R$^{10}$O— and R$^{10}$C(O)NR$^{10}$—. More preferably, $R^{1a}$ and $R^{1b}$ are hydrogen.

Preferably, $R^{1c}$ is independently selected from: hydrogen, or unsubstituted or substituted $C_1$–$C_6$ alkyl wherein the substituent on the substituted $C_1$–$C_6$ alkyl is selected from unsubstituted or substituted phenyl, —N(R$^{10}$)$_2$, R$^{10}$O— and R$^{10}$C(O)NR$^{10}$—.

Preferably, $R^{1e}$ is selected from:

a) hydrogen, b) substituted or unsubstituted aryl, substituted or unsubstituted heterocycle, $C_3$–$C_6$ cycloalkyl, $C_2$–$C_6$ alkenyl, $C_2$–$C_6$ alkynyl, R$^{10}$O—, —N(R$^{10}$)$_2$, R$^{10}$C(O)NR$^{10}$—, (R$^{10}$)$_2$N—C(O)—, or R$^{10}$OC(O)—, and c) unsubstituted or substituted $C_1$–$C_6$ alkyl wherein the substituent on the substituted $C_1$–$C_6$ alkyl is selected from substituted or unsubstituted aryl, substituted or unsubstituted heterocycle, halo, perfluoroalkyl, $C_3$–$C_6$ cycloalkyl, $C_2$–$C_6$ alkenyl, $C_2$–$C_6$ alkynyl, R$^{10}$O—, R$^4$S(O)$_m$—, R$^{10}$C(O)NR$^{10}$—, (R$^{10}$)$_2$N—C(O)—, CN, N$_3$, (R$^{10}$)$_2$N—C(NR$^{10}$)—, R$^4$S(O)$_2$NR$^{10}$—, —S(O)$_2$N(R$^{10}$)$_2$, R$^{10}$C(O)—, R$^{10}$OC(O)—, —N(R$^{10}$)$_2$, and R$^{11}$OC(O)—NR$^{10}$—;

or two $R^{1e}$s on the same carbon atom may be combined to form —(CH$_2$)$_v$—.

Preferably, $R^4$ is $C_1$–$C_6$ alkyl.

Preferably, $R^6$ and $R^7$ is selected from: hydrogen, unsubstituted or substituted $C_1$–$C_6$ alkyl, unsubstituted or substituted aryl and unsubstituted or substituted cycloalkyl.

Preferably, $R^9$ is hydrogen or methyl.

Preferably, $R^{10}$ is selected from H, $C_1$–$C_6$ alkyl and benzyl.

Preferably, $A^1$ and $A^2$ are independently selected from a bond, —C(O)NR$^{10}$—, —NR$^{10}$C(O)—, O, —N(R$^{10}$)—, —S(O)$_2$N(R$^{10}$)— and —N(R$^{10}$)S(O)$_2$—.

Preferably, V is selected from heteroaryl and aryl. More preferably, V is phenylor pyridyl.

Preferably, X and Y are independently selected from —C(O)NR$^{10}$—, —NR$^{10}$C(O)—, O, —N(R$^{10}$)—, —S(O)$_2$N(R$^{10}$)— and —N(R$^{10}$)S(O)$_2$—.

Preferably, $Z^1$ and $Z^2$ are independently selected from unsubstituted or substituted aryl and unsubstituted or substituted heteroaryl. More preferably, $Z^1$ and $Z^2$ are independently selected from unsubstituted or substituted phenyl, unsubstituted or substituted naphthyl, unsubstituted or substituted pyridyl, unsubstituted or substituted furanyl and unsubstituted or substituted thienyl. Still more preferably, $Z^1$ is selected from unsubstituted or substituted phenyl and unsubstituted or substituted naphthyl. Still more preferably, $Z^2$ is selected from a bond and unsubstituted or substituted phenyl.

Preferably, W is selected from imidazolinyl, imidazolyl, oxazolyl, pyrazolyl, pyrrolidinyl, thiazolyl and pyridyl. More preferably, W is selected from imidazolyl and pyridyl.

Preferably, n is 0, 1, or 2.

Preferably, r is 1 or 2.

Preferably p is 1, 2 or 3.

Preferably s is 0 or 1.

Preferably, the moiety

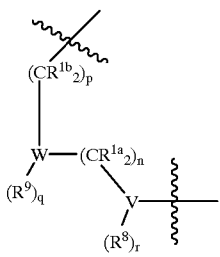

is selected from:

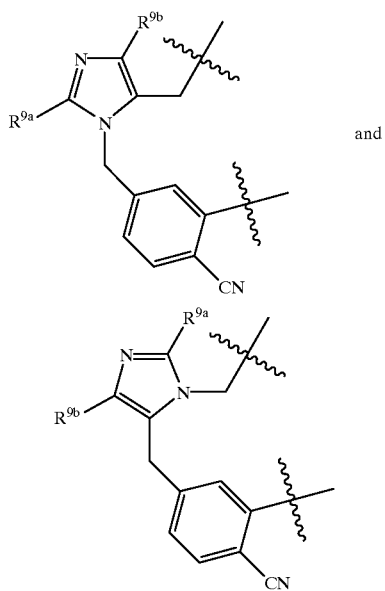

wherein $R^{9a}$ and $R^{9b}$ are independently selected from hydrogen or methyl.

It is intended that the definition of any substituent or variable (e.g., $R^{1a}$, $R^9$, n, etc.) at a particular location in a molecule be independent of its definitions elsewhere in that molecule. Thus, —N($R^{10}$)$_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–14, in addition to other standard manipulations such as ester hydrolysis, cleavage of protecting groups, etc., as may be known in the literature or exemplified in the experimental procedures. Substituents $R^{sub}$ and $R^{sub'}$, as shown in the Schemes, represent the substituents on $Z^1$ and $Z^2$ and other moieties of the instant compounds; however their point of attachment to the ring is illustrative only and is not meant to be limiting.

These reactions may be employed in a linear sequence to provide the compounds of the invention or they may be used to synthesize fragments which are subsequently joined by the alkylation reactions described in the Schemes.

Synopsis of Schemes 1–14:

The requisite intermediates are in some cases commercially available, or can be prepared according to literature procedures. In Scheme 1, for example, the synthesis of a key intermediate in the preparation of macrocyclic compounds of the instant invention containing the preferred benzylimidazolyl moiety is outlined. A suitably substituted fluorotoluene I is brominated and reacted with an imidazolylmethyl acetate to form the intermediate II. Reduction, followed by oxidation provided the aldehyde III which is then reductively alkylated with a suitably substituted amine to provide the intermediate IV.

Scheme 2 illustrates the synthesis of a compound of the instant invention which utilizes intermediate IV. Thus, a suitably substituted hydroxyanaline V is N-protected, for example with by reductive alkylation with 2,4-dimethoxybenzaldehyde, and the resulting secondary amine is reacted with a suitably substituted chloroacetyl chloride to provide intermediate VI. Intermediate VI is then reacted with the imidazolylmethylamine IV to provide the protected amide VII. Intermediate VII may then undergo a cesium carbonate nucleophillic aromatic substitution reaction resulting in an intramolecular cyclization to yield compound VIII of the instant invention. This cyclization reaction depends on the presence of an electronic withdrawing moiety (such as nitro, cyano, and the like) either ortho or para to the fluorine atom. Compound VIII may be N-deprotected to provide instant compound IX, which may itself be further elaborated, for example by boronic acid coupling to give compound X of the instant invention.

Syntheses of compounds of the instant invention wherein the linker "X" is an ether linkage are illustrated in Scheme 3. Thus, the protected amide VI is reacted with a suitably substituted sodium benzylimidazolyl methoxide to provide intermediate XI, intramolecular cyclization as previously described, followed by deprotection provides the instant compound XII, which can be further elaborated as shown.

Scheme 4 illustrates syntheses of instant compounds wherein the linker "X" is an amido linkage. Thus, the primary amine XIII, homologous to intermediate IV is reacted with a suitably substituted bromoacetyl bromide, followed by a reaction with a nucleophile, such as a suitably substituted O-protected hydroxythiophenol. The resulting intermediate XIV is deprotected and intramolecular cyclization as previously described provides compound XV of the instant invention. The sulfur moiety in compound XV also may be oxidized to provide instant compound XVI.

Scheme 5 illustrates the synthetic strategy that is employed when the $R^8$ substitutent is not an electronic withdrawing moiety either ortho or para to the fluorine atom. In the absence of the electronic withdrawing moiety, the intramolecular cyclization can be accomplished via an Ullmann reaction. Thus, the previously described aldehyde III can be converted to the homologous amine XVII. Amine XVII is then reacted with the previously described chloroacetamide VI to provide intermediate XVIII. Intramolecular cyclization may then be affected under Ullmann reaction to provide intermediate XIX, which may be deprotected and reduced to provide the diamino macrocycle of the instant invention XX.

Schemes 6–9 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

Scheme 10 depicts the synthesis of compounds of the instant invention having an imidazolyl moiety incorporated into the macrocyclic ring via different points of attachment. Activated zinc is added to a fluoroaryl methylhalide in THF to form the arylmethyl zinc halide, which is subsequently coupled to an N-protected 4-iodoimidazole to give compound XXI. Regiospecfic alkylation of the imidazole ring is accomplished with ethyl bromoacetate, with subsequent methanolysis of the intermediate imidazolium salt giving XXII. Elaboration of XXII to the primary amine proceeds through standard chemistry. Alkylation of the amine with suitably substituted N-aryl chloroacetamide (similar to the reaction illustrated in Scheme 5) provides the intermediate amide, which can then undergo cyclization as described above to provide the compound of the instant invention XXIII.

Schemes 11–14 illustrate methods of synthesizing compounds of the instant invention that comprise other permutations of the —X—$(CR^{1e}2)_r$—Y— moiety.

SCHEME 1

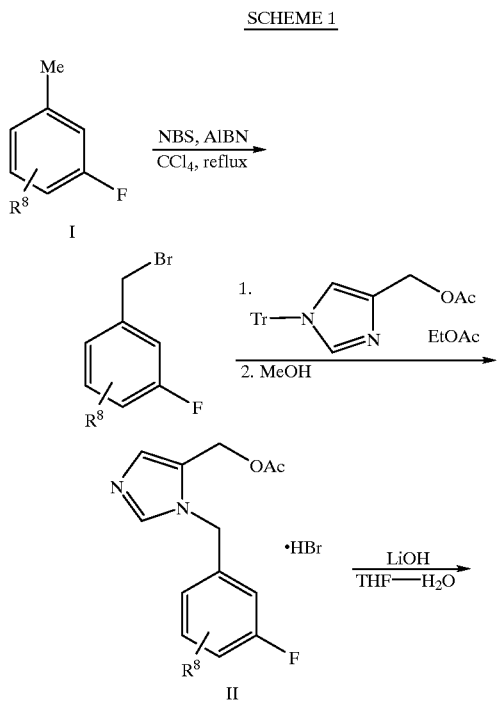

SCHEME 2

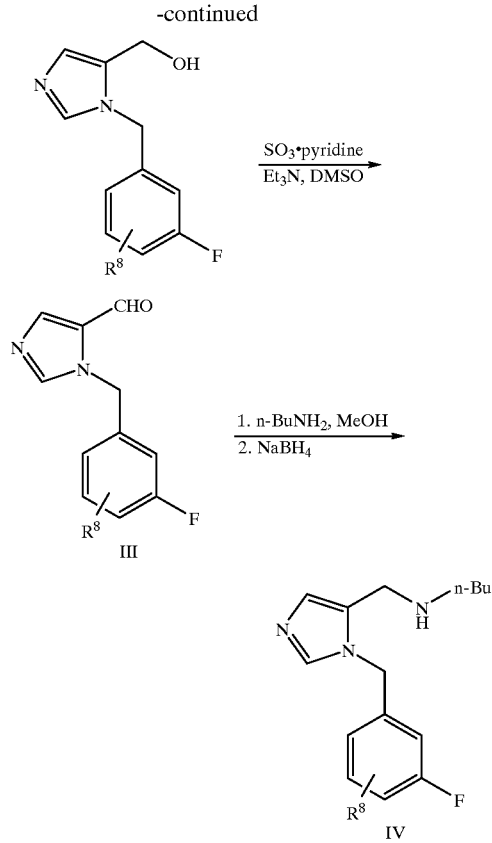

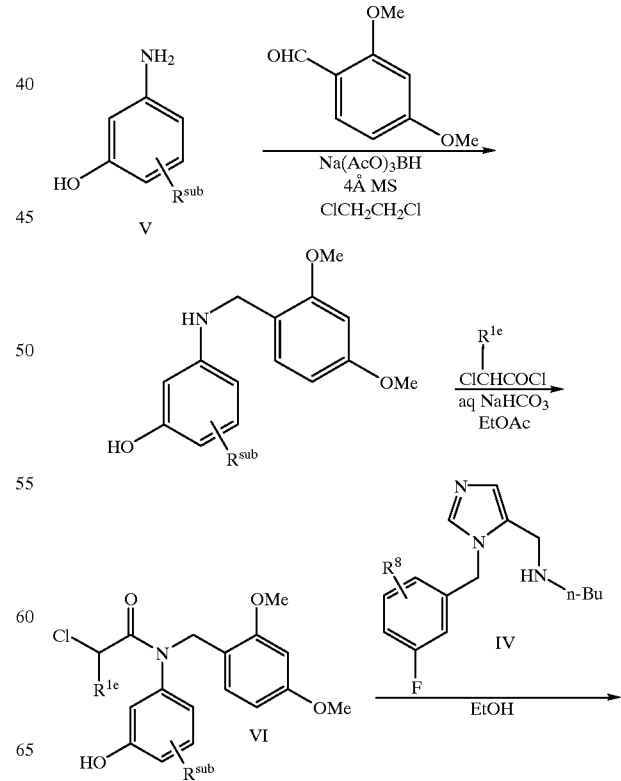

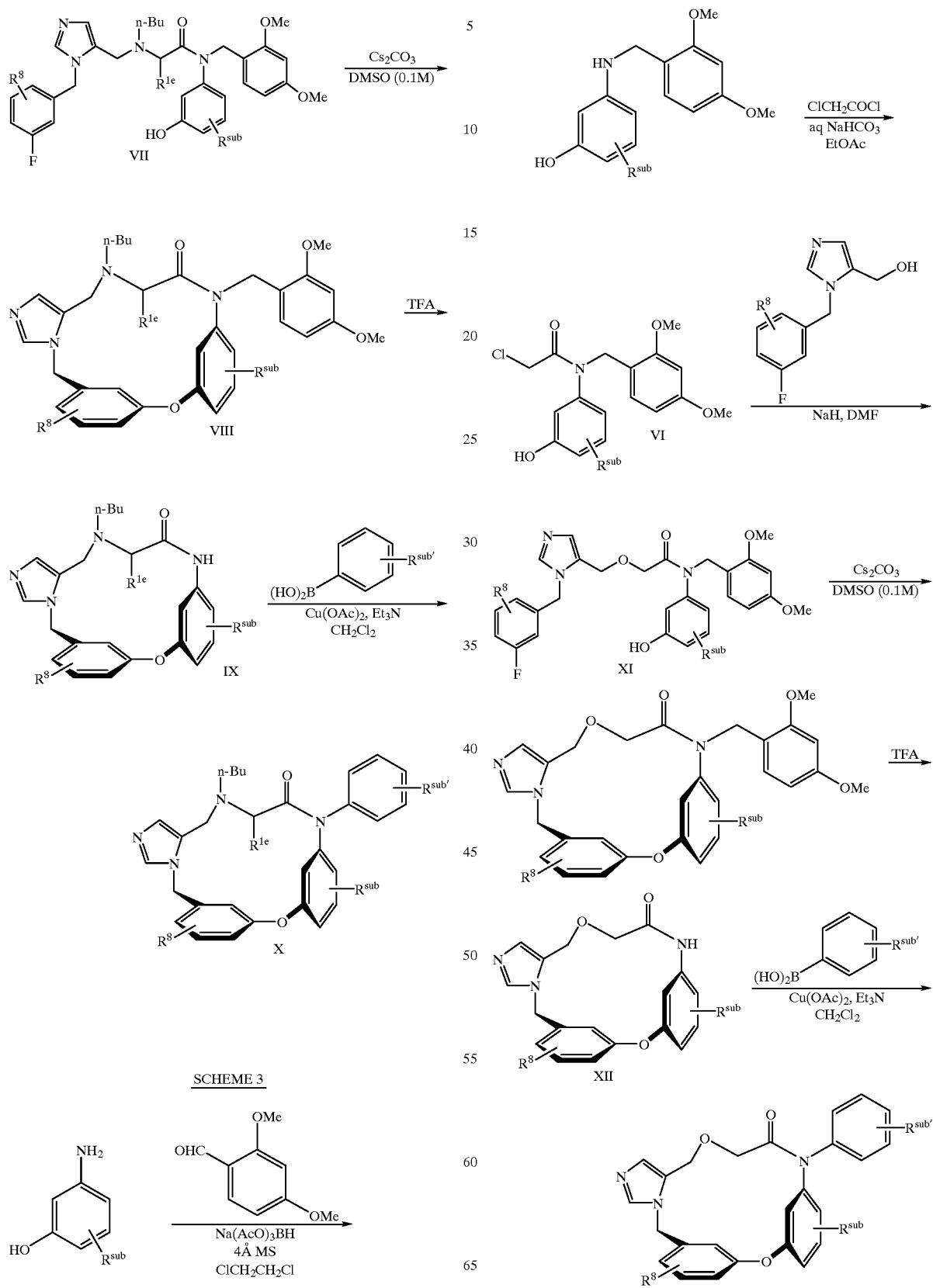

SCHEME 4
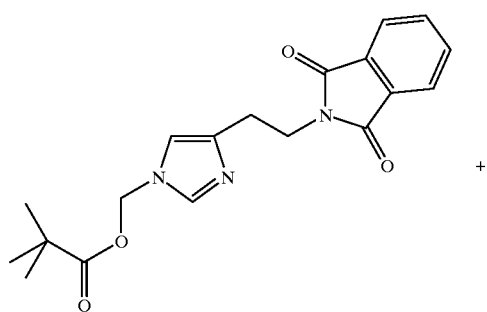
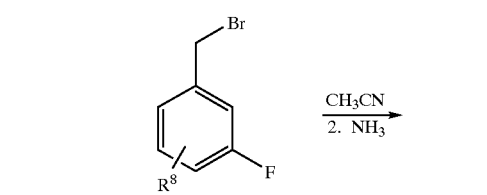
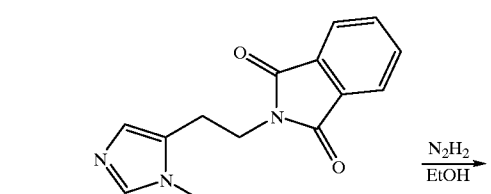
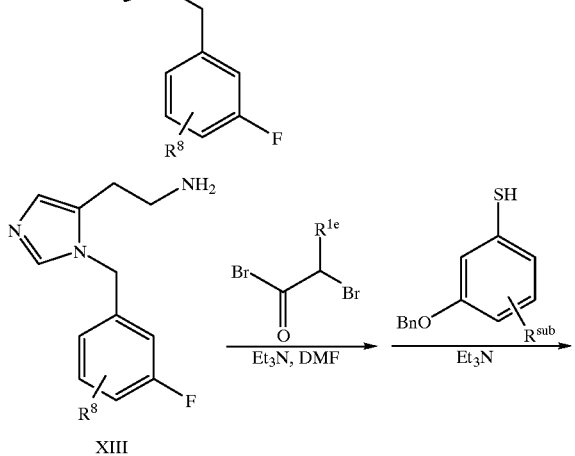
XIV
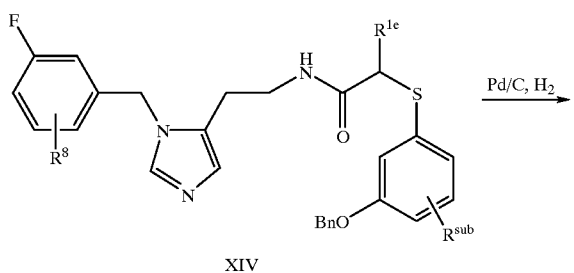
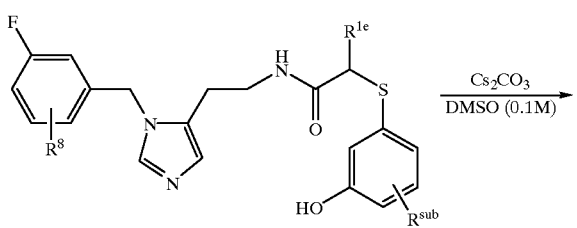
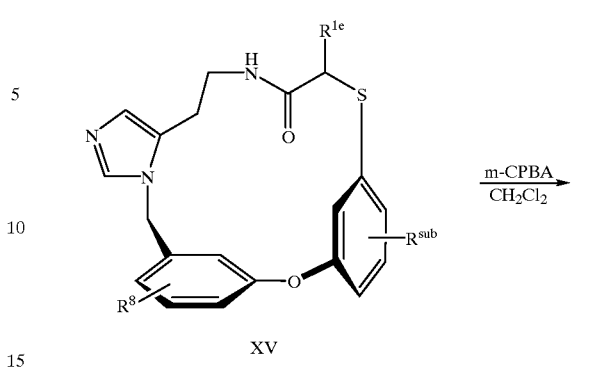
XV
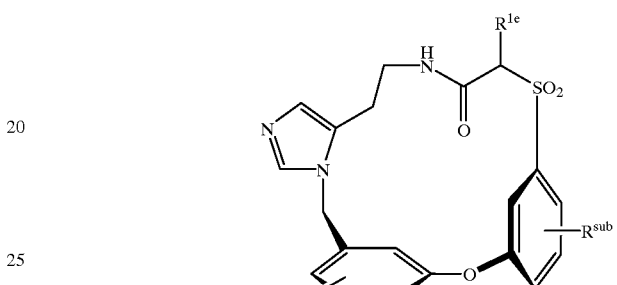
XVI
SCHEME 5
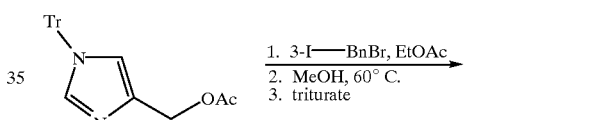
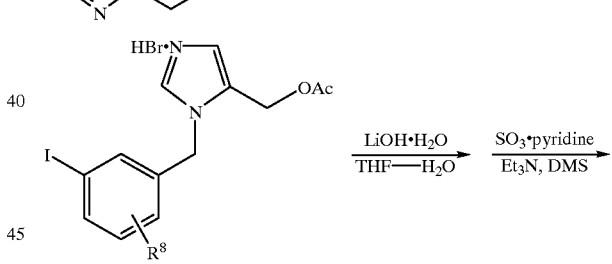
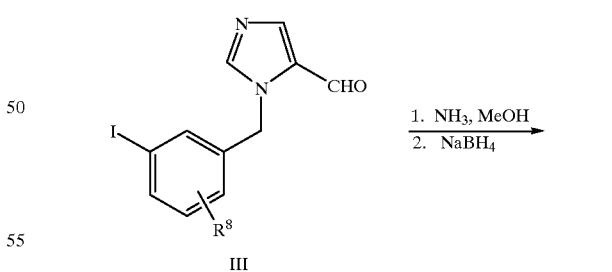
III
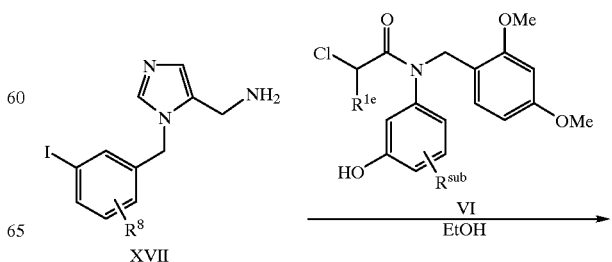
XVII -continued
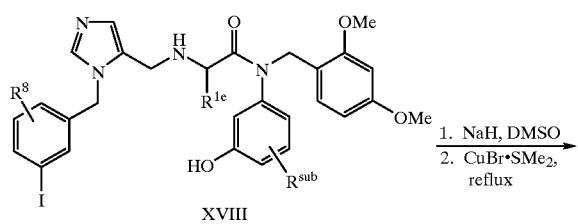
1. NaH, DMSO
2. CuBr·SMe$_2$, reflux
XVIII
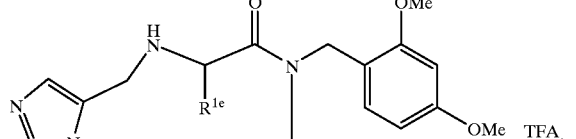
TFA
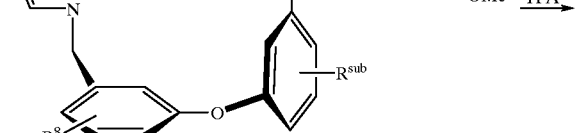
BH$_3$·SMe$_2$
BF$_3$·OEt$_2$
THF
XIX
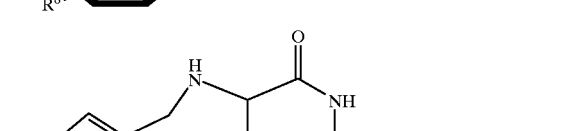
XX
SCHEME 6
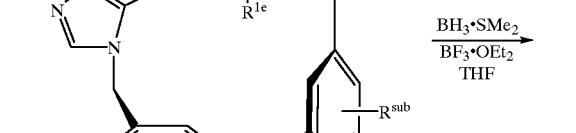
1) HNO$_2$, Br$_2$
2) KMnO$_4$
3) MeOH, H$^+$
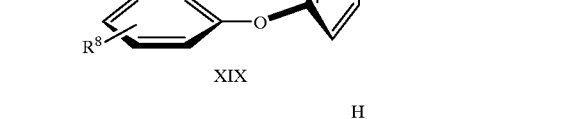
ZnCl$_2$, NiCl$_2$(Ph$_3$P)$_2$
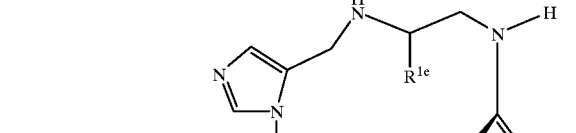
NaBH$_4$ (excess)
-continued
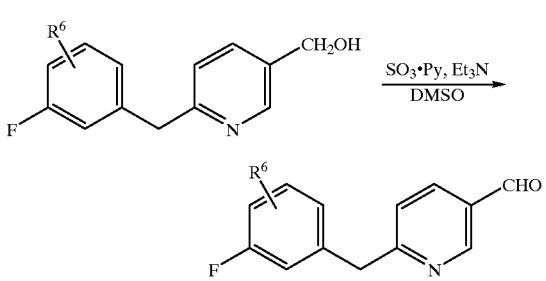
SO$_3$·Py, Et$_3$N
DMSO
SCHEME 7
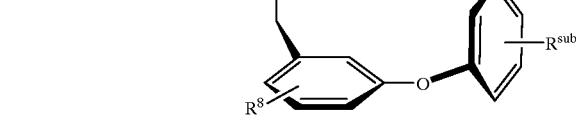
1. EtO(CO)Cl
2. 
Zn, CuCN
3. S, xylene, heat
NaBH$_4$
(excess)
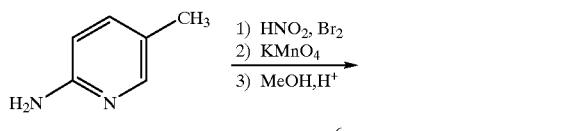
SO$_3$·Py, Et$_3$N
DMSO
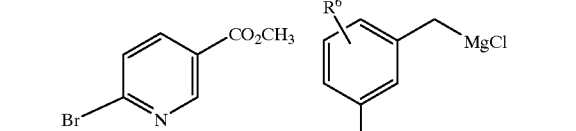
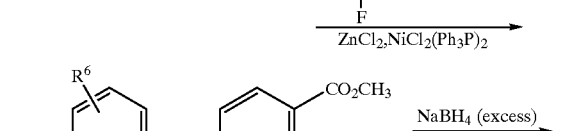
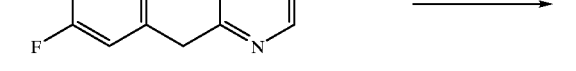
ZnCl$_2$, NiCl$_2$(Ph$_3$P)$_2$

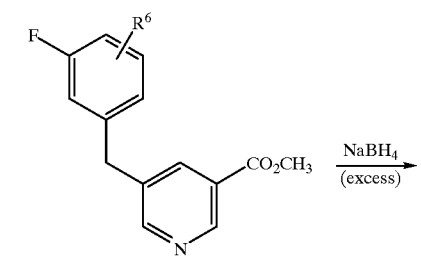
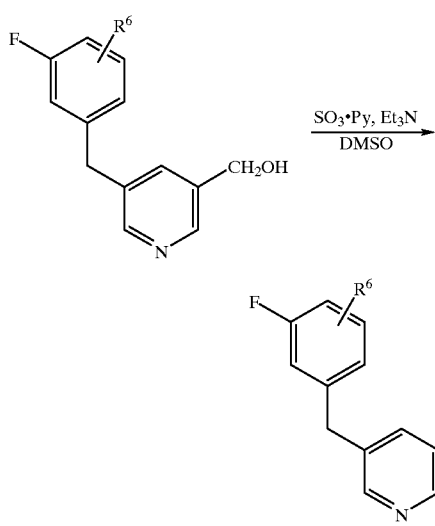
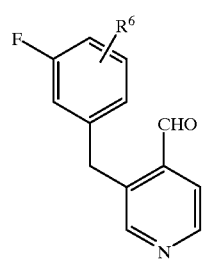
SCHEME 9
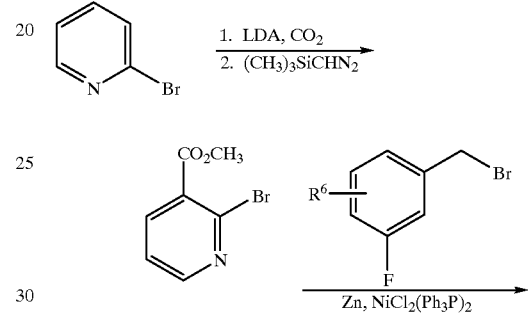
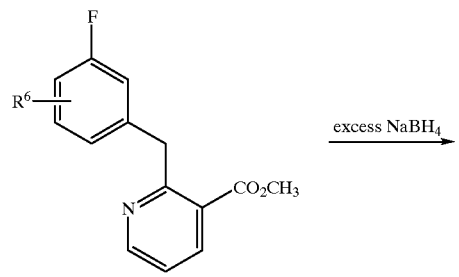
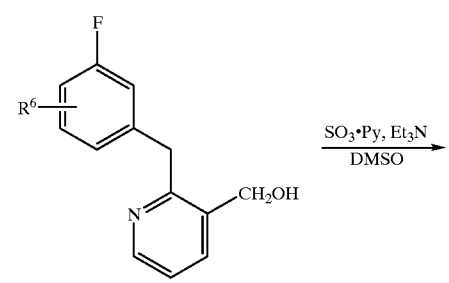
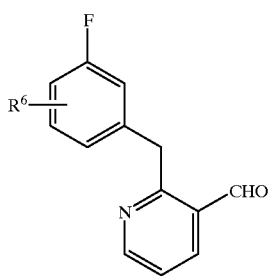
SCHEME 8
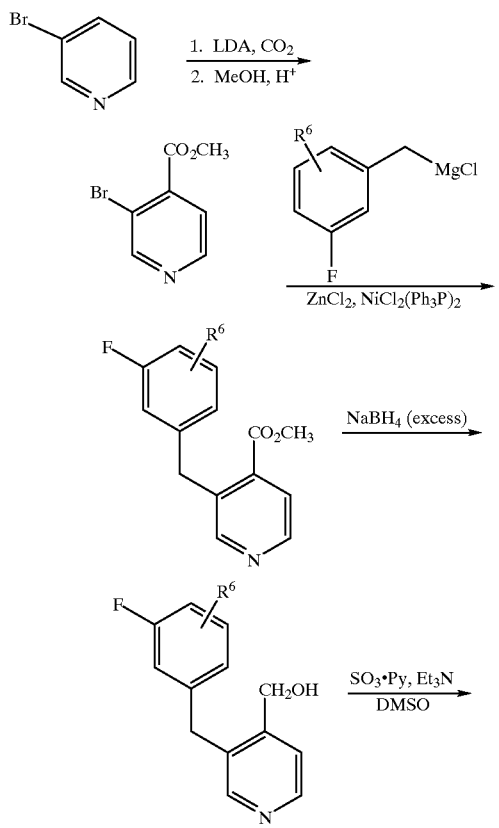

SCHEME 10
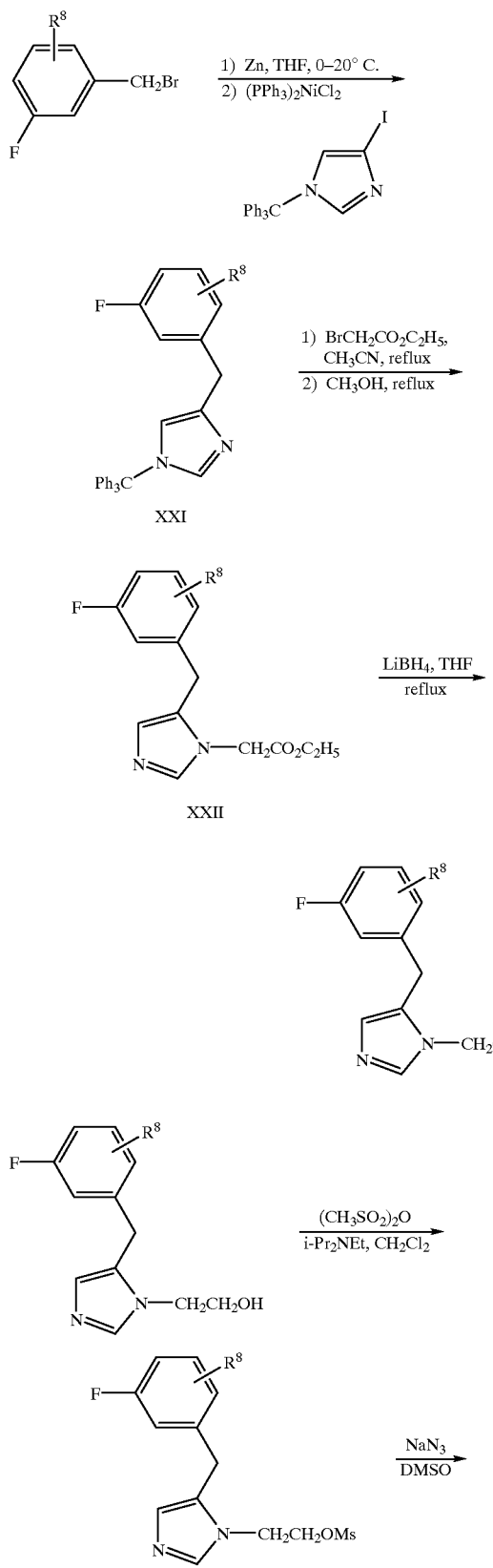
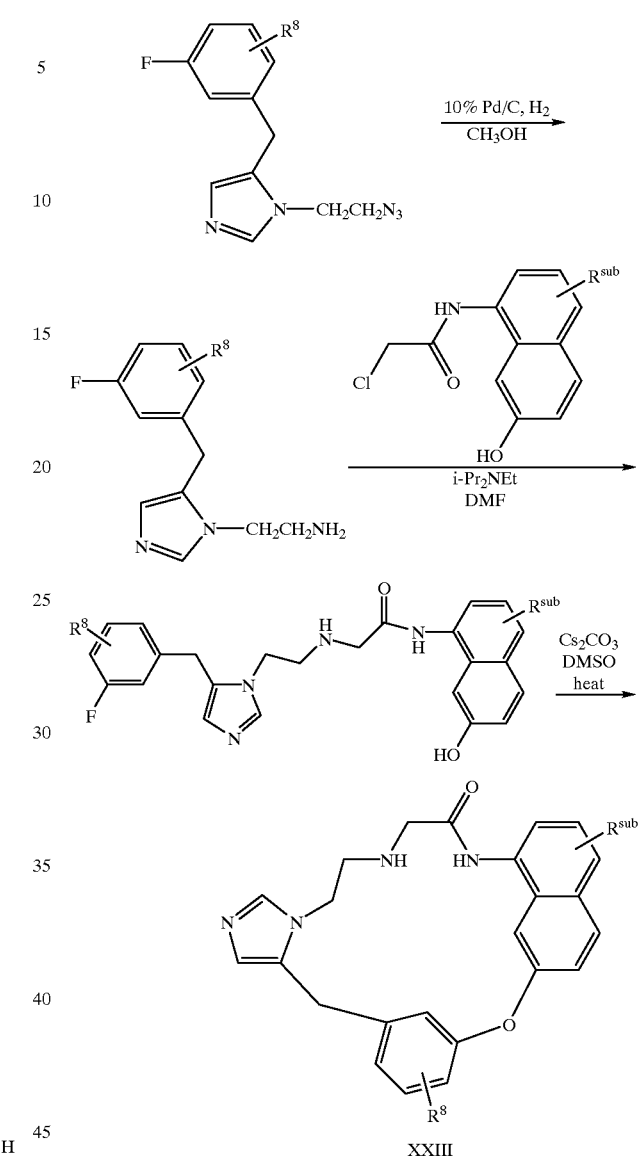
SCHEME 11
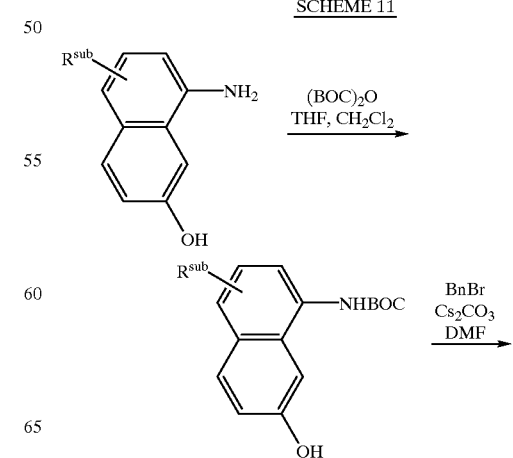

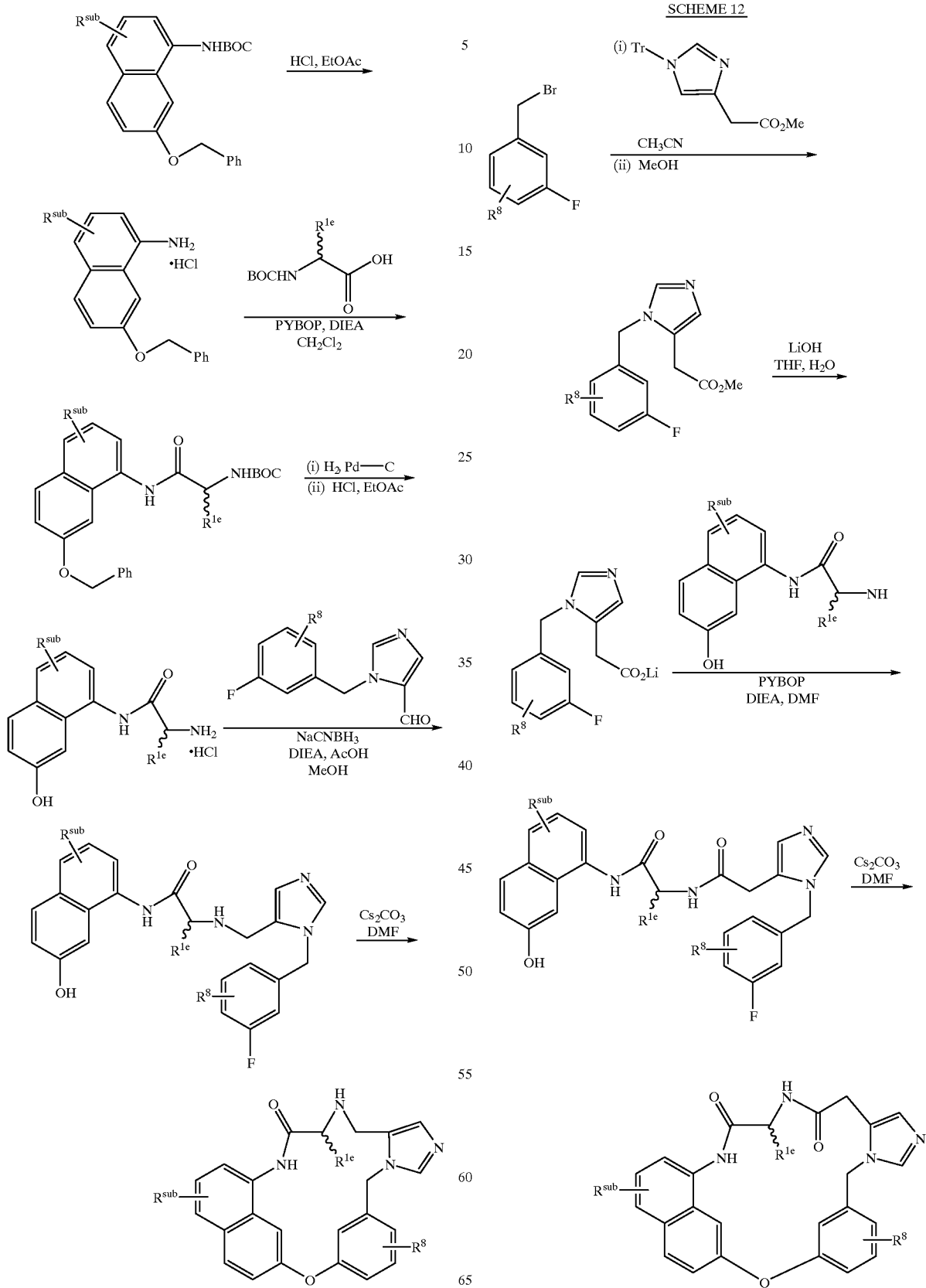

SCHEME 13
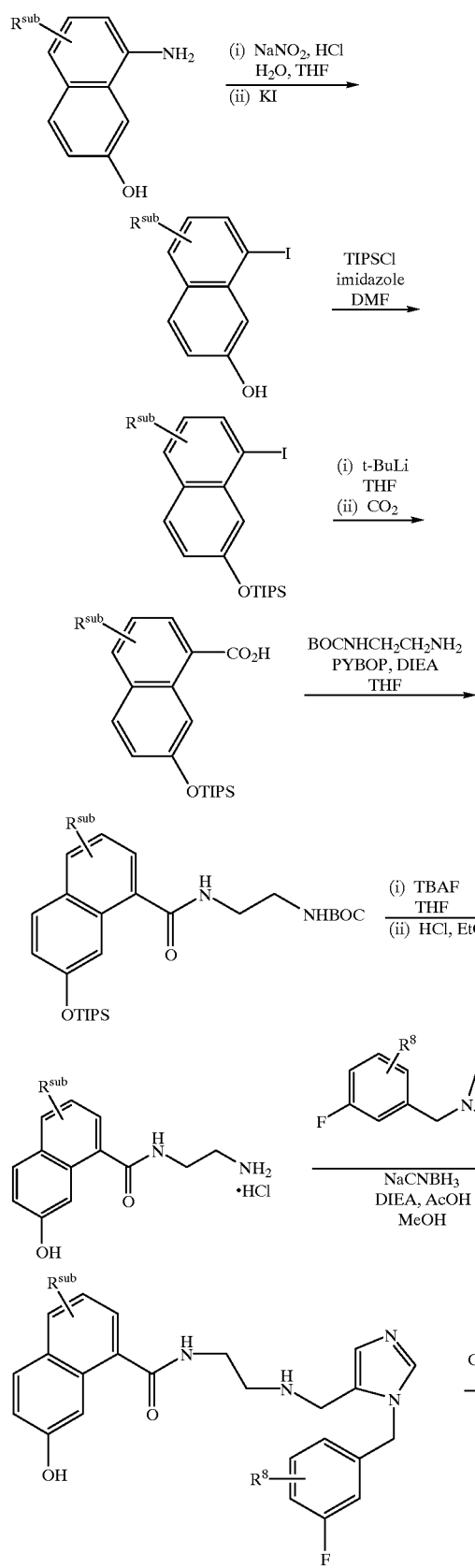
-continued
SCHEME 14
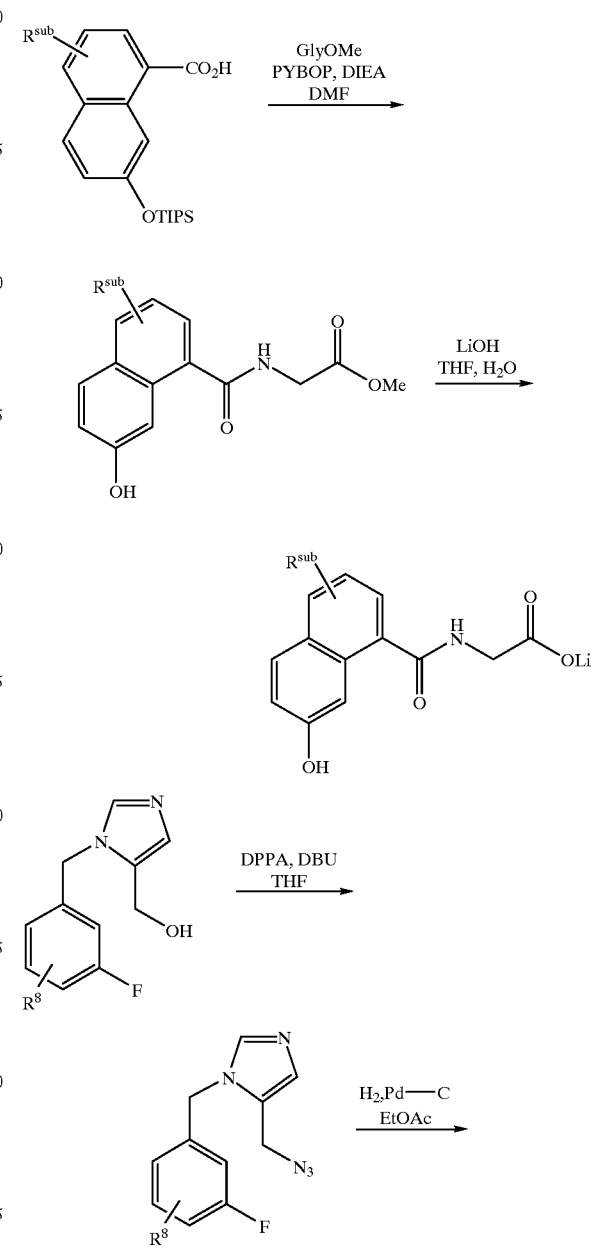

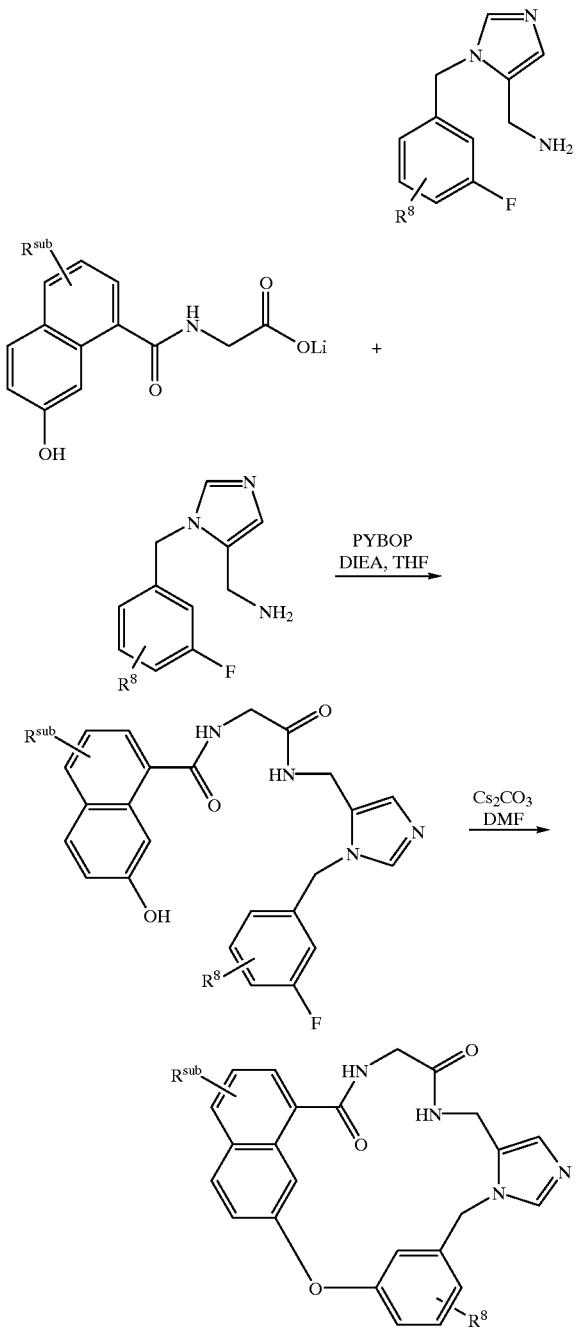

In a preferred embodiment of the instant invention the compounds of the invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 33, is at least 100 times greater than the in vitro activity of the same compound against geranylgeranyl-protein transferase-type I in the assay described in Example 34. Preferably, a selective compound exhibits at least 1000 times greater activity against one of the enzymatic activities when comparing geranylgeranyl-protein transferase-type I inhibition and farnesyl-protein transferase inhibition.

It is also preferred that the selective inhibitor of farnesyl-protein transferase is further characterized by:

a) an $IC_{50}$ (a measure of in vitro inhibitory activity) for inhibition of the prenylation of newly synthesized K-Ras protein more than about 100-fold higher than the $EC_{50}$ for the inhibition of the farnesylation of hDJ protein.

When measuring such $IC_{50}$s and $EC_{50}$s the assays described in Example 38 may be utilized.

It is also preferred that the selective inhibitor of farnesyl-protein transferase is further characterized by:

b) an $IC_{50}$ (a measurement of in vitro inhibitory activity) for inhibition of K4B-Ras dependent activation of MAP kinases in cells at least 100-fold greater than the $IC_{50}$ for inhibition of the farnesylation of the protein hDJ in cells.

It is also preferred that the selective inhibitor of farnesyl-protein transferase is further characterized by:

c) an $IC_{50}$ (a measurement of in vitro inhibitory activity) against H-Ras dependent activation of MAP kinases in cells at least 1000 fold lower than the inhibitory activity ($IC_{50}$) against H-ras-CVLL (SEQ.ID.NO.: 1) dependent activation of MAP kinases in cells.

When measuring Ras dependent activation of MAP kinases in cells the assays described in Example 37 may be utilized.

In another preferred embodiment of the instant invention the compounds of the invention are dual inhibitors of farnesyl-protein transferase and geranylgeranyl-protein transferase type I. Such a dual inhibitor may be termed a Class II prenyl-protein transferase inhibitor and will exhibit certain characteristics when assessed in in vitro assays, which are dependent on the type of assay employed.

In a SEAP assay, such as described in Examples 37, it is preferred that the dual inhibitor compound has an in vitro inhibitory activity ($IC_{50}$) that is less than about 12 $\mu$M against K4B-Ras dependent activation of MAP kinases in cells.

The Class II prenyl-protein transferase inhibitor may also be characterized by:

a) an $IC_{50}$ (a measurement of in vitro inhibitory activity) for inhibiting K4B-Ras dependent activation of MAP kinases in cells between 0.1 and 100 times the $IC_{50}$ for inhibiting the farnesylation of the protein hDJ in cells; and b) an $IC_{50}$ (a measurement of in vitro inhibitory activity) for inhibiting K4B-Ras dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 2 fold lower but less than 20,000 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 10-fold lower but less than 2,500 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5 fold lower than the inhibitory activity ($IC_{50}$) against expression of the SEAP protein in cells transfected with the pCMV-SEAP plasmid that constitutively expresses the SEAP protein.

A method for measuring the activity of the inhibitors of prenyl-protein transferase, as well as the instant combination compositions, utilized in the instant methods against Ras dependent activation of MAP kinases in cells is described in Example 37.

In yet another embodiment, a compound of the instant invention may be a more potent inhibitor of geranylgeranyl-protein transferase-type I than it is an inhibitor of farnesyl-protein transferase.

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, src, abl, lck, fyn) or by other mechanisms.

The compounds of the instant invention inhibit prenyl-protein transferase and the prenylation of the oncogene protein Ras. The instant compounds may also inhibit tumor angiogenesis, thereby affecting the growth of tumors (J. Rak et al. *Cancer Research,* 55:4575–4580 (1995)). Such anti-angiogenesis properties of the instant compounds may also be useful in the treatment of certain forms of vision deficit related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science,* 256:1331–1333 (1992).

The compounds of the instant invention are also useful in the prevention of restenosis after percutaneous transluminal coronary angioplasty by inhibiting neointimal formation (C. Indolfi et al. *Nature medicine,* 1:541–545(1995)).

The instant compounds may also be useful in the treatment and prevention of polycystic kidney disease (D. L. Schaffner et al. *American Journal of Pathology,* 142:1051–1060 (1993) and B. Cowley, Jr. et al. *FASEB Journal,* 2:A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic vascular pathologies.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethylcellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, ahard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the instant prenyl-protein transferase inhibitors and an antineoplastic agent. It is also understood that such a combination of antineoplastic agent and sinhibitor of prenyl-protein transferase may be used in conjunction in with other methods of treating cancer and/or tumors, including radiation therapy and surgery.

Examples of an antineoplastic agent include, in general, microtubule-stabilizing agents (such as paclitaxel, also known as Taxol®), docetaxel (also known as Taxotere®), epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors;

hormonal/anti-hormonal therapeutic agents, haematopoietic growth factors and antibodies (such as trastuzumab (Herceptin™)).

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel, trastuzumab (Herceptin™) and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

The preferred class of antineoplastic agents is the taxanes and the preferred antineoplastic agent is paclitaxel.

Radiation therapy, including x-rays or gamma rays which are delivered from either an externally applied beam or by implantation of tiny radioactive sources, may also be used in combination with the instant inhibitor of prenyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity. The instant compounds may also be co-administered with compounds that are selective inhibitors of geranylgeranyl protein transferase.

In particular, if the compound of the instant invention is a selective inhibitor of farnesyl-protein transferase, co-administration with a compound(s) that is a selective inhibitor of geranylgeranyl protein transferase may provide an improved therapeutic effect.

In particular, the compounds disclosed in the following patents and publications may be useful as farnesyl pyrophosphate-competitive inhibitor component of the instant composition: U.S. Ser. Nos. 08/254,228 and 08/435,047. Those patents and publications are incorporated herein by reference.

In practicing methods of this invention, which comprise administering, simultaneously or sequentially or in any order, two or more of a protein substrate-competitive inhibitor and a farnesyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and farnesyl pyrophosphate-competitive inhibitor are administered sequentially, the administration of each can be by the same method or by different methods.

The instant compounds may also be useful in combination with an integrin antagonist for the treatment of cancer, as described in U.S. Ser. No. 09/055,487, filed Apr. 6, 1998, which is incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the $\alpha v \beta 3$ integrin, which selectively antagonize, inhibit or counteract binding of a physiological ligand to the $\alpha v \beta 5$ integrin, which antagonize, inhibit or counteract binding of a physiological ligand to both the $\alpha v \beta 3$ integrin and the $\alpha v \beta 5$ integrin, or which antagonize, inhibit or counteract the activity of the particular integrin(s) expressed on capillary endothelial cells. The term also refers to antagonists of the $\alpha 1 \beta 1$, $\alpha 2 \beta 1$, $\alpha 5 \beta 1$, $\alpha 6 \beta 1$ and $\alpha 6 \beta 4$ integrins. The term also refers to antagonists of any combination of $\alpha v \beta 3$ integrin, $\alpha v \beta 5$ integrin, $\alpha 1 \beta 1$, $\alpha 2 \beta 1$, $\alpha 5 \beta 1$, $\alpha 6 \beta 1$ and $\alpha 6 \beta 4$ integrins. The instant compounds may also be useful with other agents that inhibit angiogenisis and thereby inhibit the growth and invasiveness of tumor cells, including, but not limited to angiostatin and endostatin.

Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the combinations of this invention within the dosage range described below and the other pharmaceutically active agent(s) within its approved dosage range. Combinations of the instant invention may alternatively be used sequentially with known pharmaceutically acceptable agent(s) when a multiple combination formulation is inappropriate.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

20-n-Butyl-17,18,19,20-tetrahydro-17-[2,4-dimethoxybenzyl]-18-oxo-5H-6,10:12,16-dimetheno-21H-imidazo[4,3-l][1,7,10,13]oxatriaza-cyclononadecine-9-carbonitrile (Compound 1), dihydrochloride salt

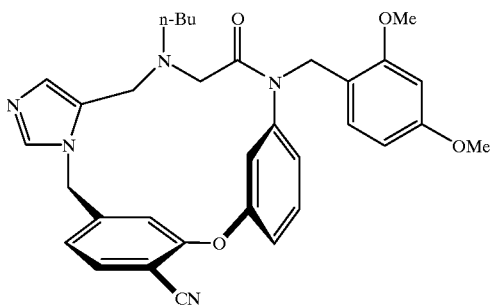

Step A: Preparation of 1-triphenylmethyl-4-(hydroxymethyl)-imidazole

To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: Preparation of 1-triphenylmethyl-4-(acetoxymethyl)-imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a white powder which was sufficiently pure for use in the next reaction.

Step C: Preparation of 4-cyano-3-fluorotoluene

To a degassed solution of 4-bromo-3-fluorotoluene (50.0 g, 264 mmol) in 500 mL of DMF was added Zn(CN)$_2$ (18.6 g, 159 mmol) and Pd(PPh$_3$)$_4$ (6.1 g, 5.3 mmol). The reaction was stirred at 80° C. for 6 hours, then cooled to room temperature. The solution was poured into EtOAc, washed with water, sat. aq. NaHCO$_3$, and brine, then dried (Na$_2$SO$_4$), filtered, and concentrated in vacuo to provide the crude product. Purification by silica gel chromatography (0–5% EtOAc/hexane) provided the titled product.

Step D: Preparation of 4-cyano-3-fluorobenzylbromide

To a solution of the product from Step C (22.2 g, 165 mmol) in 220 mL of carbontetrachloride was added N-bromosuccinimide (29.2 g, 164 mmol) and benzoylperoxide (1.1 g). The reaction was heated to reflux for 30 minutes, then cooled to room temperature. The solution was concentrated in vacuo to one-third the original volume, poured into EtOAc, washed with water, sat. aq. NaHCO$_3$, and brine, then dried (Na$_2$SO$_4$), filtered, and concentrated in vacuo to provide the crude product. Analysis by 1H NMR indicated only partial conversion, so the crude material was resubjected to the same reaction conditions for 2.5 hours, using 18 g (102 mmol) of N-bromosuccinimide. After workup, the crude material was purified by silica gel chromatography (0–10% EtOAc/hexane) to provide the desired product.

Step E: Preparation of 1-(4-cyano-3-fluorobenzyl)-5-(acetoxymethyl)-imidazole hydrobromide A solution of the product from Step B (36.72 g, 96.14 mmol) and the product from Step D (20.67 g, 96.14 mmol) in 250 mL of EtOAc was stirred at 60° C. for 20 hours, during which a white precipitate formed. The reaction was cooled to room temperature and filtered to provide the solid imidazolium bromide salt. The filtrate was concentrated in vacuo to a volume of 100 mL, reheated at 60° C. for two hours, cooled to room temperature, and filtered again. The filtrate was concentrated in vacuo to a volume 40 mL, reheated at 60° C. for another two hours, cooled to room temperature, and concentrated in vacuo to provide a pale yellow solid. All of the solid material was combined, dissolved in 300 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step F: Preparation of 1-(4-cyano-3-fluorobenzyl)-5-(hydroxymethyl)imidazole

To a solution of the product from Step E (31.87 g, 89.77 mmol) in 300 mL of 2:1 THF/water at 0° C. was added lithium hydroxide monohydrate (7.53 g, 179 mmol). After two hours, the reaction was concentrated in vacuo to a 100 mL volume, stored at 0° C. for 30 minutes, then filtered and washed with 700 mL of cold water to provide a brown solid. This material was dried in vacuo next to P$_2$O$_5$ to provide the titled product as a pale brown powder which was sufficiently pure for use in the next step without further purification.

Step G: Preparation of 1-(4-cyano-3-fluorobenzyl)-5-imidazolecarboxaldehyde

To a solution of the alcohol from Step F (2.31 g, 10.0 mmol) in 20 mL of DMSO at 0° C. was added triethylamine (5.6 mL, 40 mmol), then SO$_3$-pyridine complex (3.89 g, 25 mmol). After 30 minutes, the reaction was poured into EtOAc, washed with water and brine, dried (Na$_2$SO$_4$), filtered, and concentrated in vacuo to provide the aldehyde as a pale yellow powder which was sufficiently pure for use in the next step without further purification.

Step H: Preparation of 1-(4-cyano-3-fluorobenzyl)-5-[(N-(n-butyl)amino)methyl]imidazole To a solution of the product from Step G (114 mg, 0.498 mmol) in 1 mL of methanol was added n-butylamine (0.059 mL, 0.60 mmol). After 18 hours, sodium borohydride was added (25 mg, 0.66 mmol) and the reaction was stirred for one hour. The solution was poured into EtOAc, washed with water and brine, dried ($Na_2SO_4$), filtered, and concentrated in vacuo to provide the titled product as a yellow oil.

Step I: Preparation of N-(2,4-dimethoxybenzyl)-3-hydroxyaniline

To a solution of 3-hydroxyaniline (1 equiv) in 1,2-dichloroethane is added 4Å powdered molecular sieves, followed by sodium triacetoxyborohydride (1.5 equiv). 2,4-dimethoxybenzaldehyde (1.1 equiv) is added, and the reaction is stirred at room temperature. After completion, the reaction is poured into EtOAc, washed with sat. aq. $NaHCO_3$ and brine, dried ($Na_2SO_4$), filtered, and concentrated in vacuo to provide the titled product.

Step J: Preparation of N-chloroacetyl-N-(2,4-dimethoxybenzyl)-3-hydroxyaniline

To a solution of the product from Step I (1 equiv) in 1:1 EtOAc-saturated $NaHCO_3$ solution at 0° C. is added chloroacetyl chloride (3 equiv) dropwise. After completion, the layers a separated, and the organic solution is washed with water and brine, dried ($Na_2SO_4$), filtered, and concentrated in vacuo to provide the titled product.

Step K: Preparation of N-[N'-(n-butyl)-N'-[1-(4-cyano-3-fluorobenzyl)-5-imidazolylmethyl]aminoacetyl]-N-(2,4-dimethoxybenzyl)-3-hydroxyaniline hydrochloride To a solution of the product from Step J (1 equiv) in ethanol is added the product from Step H (1 equiv). The solution is warmed to 60° C. After completion, the solution is cooled to room temperature and concentrated in vacuo to provide the titled product.

Step M: Preparation of Compound 1, dihydrochloride salt

To a solution of the product from Step K (1 equiv) in DMSO is added cesium carbonate (3 equiv). The reaction is warmed to 60° C. under argon, then cooled to room temperature after completion of the reaction. The solution is poured into EtOAc and washed with water and brine, dried ($Na_2SO_4$), filtered, and concentrated in vacuo to provide the titled product. After purification by silica gel chromatography, the product is taken up in $CH_2Cl_2$ and treated with excess 1 M HCl/ether solution, then concentrated in vacuo to provide the titled product hydrochloride.

Example 2

20-n-Butyl-17,18,19,20-tetrahydro-1 8-oxo-5H-6, 10:12,16-dimetheno-21H-imidazo[4,3-l][1,7,10,13] oxatriazacyclononadecine-9-carbonitrile Compound 2, dihydrochloride salt

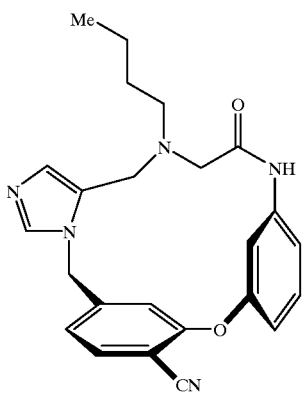

2

To Compound 1, from Example 1 (1 equiv) at 0° C. is added excess trifluoroacetic acid. The reaction is warmed to room temperature and stirred until completion of the reaction. The solution is concentrated in vacuo, then partitioned between aq. $NaHCO_3$ solution and $CH_2Cl_2$, and the aqueous layer is extracted with $CH_2Cl_2$. The combined organic layers are dried ($Na_2SO_4$), filtered, and concentrated in vacuo. After purification by silica gel chromatography, the product is taken up in $CH_2Cl_2$ and treated with excess 1 M HCl/ether solution, then concentrated in vacuo to provide the titled product hydrochloride.

Example 3

20-n-Butyl-17,18,19,20-tetrahydro-18-oxo-17-[3-(trifluoromethyl)phenyl]-5H-6,10,12,16-dimetheno-21H-imidazo[4,3-l][1,7,10,13] oxatriazacyclononadecine-9-carbonitrile Compound 3, dihydrochloride

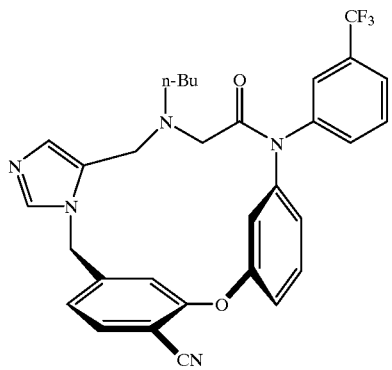

3

To Compound 2, from Example 2 (1 equiv, as the free base) in $CH_2Cl_2$ at room temperature is added 3-(trifluoromethyl) phenylboronic acid (2 equiv), Cu(OAc)2 (1 equiv), and 4Å molecular sieves. Triethylamine (5 equiv)

is added, and the solution is stirred at room temperature. After completion, the solution is filtered and concentrated in vacuo, and the resulting material is purified by silica gel chromatography. The product is taken up in CH$_2$Cl$_2$ and treated with excess 1 M HCl/ether solution, then concentrated in vacuo to provide the titled product hydrochloride.

Example 4

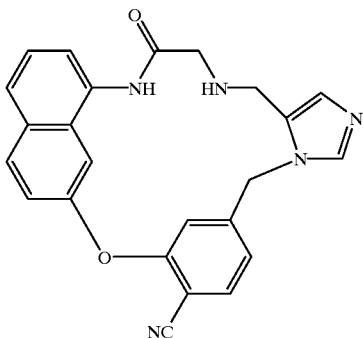

19,20,21,22-Tetrahydro-19-oxo-5H-12,14-etheno-6, 10-metheno-18H-benz[d]imidazo[4,3-k][1,6,9,12] oxatriazacyclooctadecine-9-carbonitrile hydrochloride Step A: 4-(Hydroxymethyl)-1-(triphenylmethyl)imidazole To a solution of 4-(hydroxymethyl)imidazole hydrochloride (35.0 g, 260 mmol) in dry DMF (250 mL) at room temperature was added triethylamine (90.6 mL, 650 mmol). A white solid precipitated from the solution. Chlorotriphenylmethane (76.1 g, 273 mmol) in DMF (500 mL) was added dropwise. The reaction mixture was stirred for 20 hrs, poured over ice, filtered, and washed with ice water. The resulting product was slurried with cold dioxane, filtered, and dried in vacuo to provide the titled product as a white solid.

Step B: 4-(Acetoxymethyl)-1-(triphenylmethyl)imidazole 4-(Hydroxymethyl)-1-(triphenylmethyl)imidazole, as described above in Step A, (88.5 g, 260 mmol) was suspended in pyridine (500 mL). Acetic anhydride (74 mL, 780 mmol) was added dropwise, and the reaction was stirred for 48 hrs during which it became homogeneous. The solution was poured into EtOAc, and washed sequentially with water, 5% aqueous HCl solution, saturated aqueous NaHCO$_3$ solution, and brine. The organic extracts were dried (Na$_2$SO$_4$), and concentrated in vacuo to provide the ester as a white powder.

Step C: 4-Cyano-3-fluorotoluene

To a deoxygenated solution of 4-bromo-3-fluorotoluene (25.0 g, 132 mmol) in DMF (500 mL) was added Zn(CN)$_2$ (10.1 g, 86 mmol) and Pd(PPh$_3$)$_4$ (15 g, 13 mmol). The reaction was stirred at 100° C. for 18 hrs, then cooled to room temperature. The solution was poured into toluene (1 L), washed with 30% aqueous NH$_4$OH (2×1 L), then brine (800 mL), then dried (Na$_2$SO$_4$), filtered, and concentrated in vacuo to provide the crude product. Purification by silica gel chromatography, eluting with a gradient of hexane −0% to 7% EtOAc, yielded the titled product.

Step D: 4-Cyano-3-fluorobenzyl bromide

To a solution of 4-cyano-3-fluorotoluene, as described above in Step C, (5.0 g, 37.0 mmol) in carbon tetrachloride (300 mL) was added N-bromosuccinimide (7.57 g, 42.6 mmol) and 2,2'-azobisisobutyronitrile (610 mg, 3.7 mmol). The reaction mixture was heated to reflux under argon for 24 hrs, then cooled to room temperature, filtered, and concentrated under reduced pressure. The residue was purified by silica gel chromatography, eluting with a gradient of hexane −4% to 7% EtOAc, to yield the titled product as a yellow solid.

Step E: 5-(Acetoxymethyl)-1-(4-cyano-3-fluorobenzyl) imidazole hydrobromide

A mixture of 4-(acetoxymethyl)-1-(triphenylmethyl) imidazole, as described above in Step B, (19.7 g, 51.4 mmol) and 4-cyano-3-fluorobenzyl bromide, as described above in Step D, (11.0 g, 51.4 mmol) in dry CH$_3$CN (140 mL) was stirred at 50° C. for 3 hrs, during which a white precipitate formed. The reaction was cooled to room temperature and filtered to provide the solid imidazolium bromide salt. The filtrate was concentrated in vacuo to a volume of 70 mL, reheated at 50° C. for 2 hrs, cooled to room temperature, and filtered again. The solid material was combined and dissolved in MeOH (500 mL), and the solution was heated to reflux for 2 hrs. The solution was concentrated in vacuo to a volume of 20 mL, then cold hexane—EtOAc (1:1, 500 mL) was added and the white precipitate was collected and dried in vacuo.

Step F: 1-(4-Cyano-3-fluorobenzyl)-5-(hydroxymethyl) imidazole

To a solution of 5-(acetoxymethyl)-1-(4-cyano-3-fluorobenzyl)imidazole, as described above in Step E, (19.8 g, 72.5 mmol) in 5:1 THF/water (430 mL) at ambient temperature was added lithium hydroxide monohydrate (3.33 g, 79.4 mmol). After 4 hrs, the solution was adjusted to pH 7 with 1.0 N hydrochloric acid and concentrated in vacuo. The residue was concentrated from toluene in vacuo (3×100 mL) to give the titled product as a pale solid.

Step G: 1-(4-Cyano-3-fluorobenzyl)-5-imidazolecarboxaldehyde

To a solution of 1-(4-cyano-3-fluorobenzyl)-5-(hydroxymethyl)imidazole, as described above in Step F, (2.31 g, 10.0 mmol) in 20 mL of DMSO at 0° C. was added triethylamine (5.6 mL, 40 mmol), then SO$_3$-pyridine complex (3.89 g, 25 mmol). After 30 minutes, the reaction was poured into EtOAc, washed with water and brine, dried (Na$_2$SO$_4$), filtered, and concentrated in vacuo to provide the aldehyde as a pale yellow powder.

Step H: 8-(tert-Butoxycarbonylamino)-2-naphthol

A mixture of 8-amino-2-naphthol (500 mg, 3.14 mmol) and di-tert-butyl dicarbonate (685 mg, 3.14 mmol) in CH$_2$Cl$_2$ (10 mL) and THF (5 mL) was stirred at 70° C. for 18 hrs, then poured into saturated aqueous Na$_2$CO$_3$ (25 mL) and CH$_2$Cl$_2$ (75 mL). The aqueous layer was extracted further with CH$_2$Cl$_2$ (2×50 mL). The combined organic extracts were dried over Na$_2$SO$_4$, filtered, and concentrated in vacuo. The crude product was purified by flash column chromatography on silica, eluting with a gradient of CH$_2$Cl$_2$-0 to 7% ethyl acetate to yield the desired product as a light brown solid.

Step I: 7-Benzyloxy-1-(tert-butoxycarbonylamino) naphthalene

A mixture of 8-(tert-butoxycarbonylamino)-2-naphthol, as described above in Step H, (93 mg, 0.36 mmol), benzyl bromide (64 mg, 0.37 mmol), and Cs$_2$CO$_3$ (146 mg, 0.45 mmol) in dry DMF (3 mL) was stirred, under argon, at ambient temperature for 18 hrs. The reaction mixture was poured into saturated aqueous NaHCO$_3$ (15 mL) and EtOAc (20 mL). The organic layer was dried over Na$_2$SO$_4$, filtered, and concentrated in vacuo. The crude product was purified by flash column chromatography on silica, eluting with a gradient of hexane −5 to 15% diethyl ether to yield the desired product as a pale solid.

63

Step J: 1-Amino-7-benzyloxynaphthalene

A solution of 7-benzyloxy-1-(tert-butoxycarbonylamino) naphthalene, as described above in Step I, (100 mg, 0.29 mmol) in EtOAc (10 mL) at 0° C. was saturated with HCl (g). After 15 min, the mixture was concentrated in vacuo. The residue was partitioned between saturated aqueous $Na_2CO_3$ (5 mL) and $CH_2Cl_2$ (10 mL). The aqueous layer was extracted further with $CH_2Cl_2$ (2×10 mL). The combined organic extracts were dried over $Na_2SO_4$, filtered, and concentrated in vacuo to yield the desired amine as a pale solid.

Step K: N-(7-Benzyloxynaphthalen-1-yl)(tert-butoxycarbonylamino)acetamide

To N-(tert-butoxycarbonyl)glycine (527 mg, 3.01 mmol) in dry $CH_2Cl_2$ (5 mL) under argon were added PYBOP (1.65 g, 3.16 mmol), 1-amino-7-benzyloxynaphthalene, as described above in Step J, (750 mg, 3.01 mmol), and N,N-diisopropylethylamine (0.55 mL, 3.16 mmol). The reaction mixture was stirred for 18 hrs, then partitioned between $CH_2Cl_2$ (200 mL) and 10% aqueous citric acid (50 mL). The organic layer was dried over $Na_2SO_4$, filtered, and concentrated in vacuo. The crude product was sufficiently pure for use in the next reaction.

Step L: (tert-Butoxycarbonylamino)-N-(7-hydroxynaphthalen-1yl)acetamide

To a solution of N-(7-benzyloxynaphthalen-1-yl)(tert-butoxycarbonylamino)acetamide, as described above in Step K, (1.22 g, 3.01 mmol) in EtOH (30 mL) was added 10% Pd-C on carbon (220 mg) and the reaction mixture was stirred under an atmosphere of hydrogen (ca. 1 atm) at ambient temperature for 18 hrs. The mixture was filtered through a pad of celite, washing with EtOH, and the filtrate was concentrated in vacuo to give a crude product. This was purified by flash column chromatography on silica, eluting with EtOAc, to yield the titled product as a pale solid.

Step M: Amino-N-(7-hydroxynaphthalen-1yl)acetamide hydrochloride

A solution of (tert-butoxycarbonylamino)-N-(7-hydroxynaphthalen-1-yl)acetamide, as described above in Step L, (950 mg, 3.0 mmol) in EtOAc (20 mL) at 0° C. was saturated with HCl (g). After 15 min, the mixture was concentrated in vacuo to yield the amine hydrochloride as a white solid.

Step N: 2-{[3-(4-Cyano-3-fluorobenzyl)-3H-imidazol-4-ylmethyl]amino}-N-(7-hydroxynaphthalen-1-yl)acetamide Amino-N-(7-hydroxynaphthalen-1yl)acetamide hydrochloride, as described above in Step M, (90 mg, 0.36 mmol) and 1-(4-cyano-3-fluorobenzyl)-5-imidazolecarboxaldehyde, as described above in Step G, (82 mg, 0.36 mmol), were stirred in MeOH (2 mL) and was neutralized with N,N-diisopropylethylamine. Acetic acid was then added dropwise to adjust the mixture to ca. pH 5, as judged by wetted pH paper. The mixture was stirred for 1 hr at ambient temperature, then $NaCNBH_3$ (25 mg, 0.40 mmol) was added, the solution was readjusted to ca. pH 5 by addition of AcOH, and stirring was continued for 18 hrs. The reaction was quenched with saturated aqueous $Na_2CO_3$ (2 mL) and most of the MeOH was removed under reduced pressure. The residual solution was partitioned between saturated aqueous $Na_2CO_3$ (10 mL) and $CH_2Cl_2$ (20 mL). The aqueous layer was extracted further with $CH_2Cl_2$ (3×20 mL). The combined organic extracts were dried over $Na_2SO_4$, filtered, and concentrated in vacuo. The crude product was purified by flash column chromatography on silica, eluting with a gradient of 1% to 6% MeOH-0.1% to 0.6% $NH_4OH$—$CH_2Cl_2$ to yield the titled product.

64

Step O: 19,20,21,22-Tetrahydro-19-oxo-5H-12,14-etheno-6,10-metheno-18H-benz[d]imidazo[4,3-k][1,6,9,12] oxatriazacyclooctadecine-9-carbonitrile hydrochloride A mixture of 2-{[3-(4-cyano-3-fluorobenzyl)-3H-imidazol-4-ylmethyl]amino}-N-(7-hydroxynaphthalen-1-yl)acetamide, as described above in Step N, (170 mg, 0.40 mmol) and $Cs_2CO_3$ (322 mg, 0.99 mmol) in dry, degassed DMF (40 mL) was stirred at 60° C. under argon for 18 hrs, then the solvent was removed under reduced pressure. The residue was partitioned between saturated aqueous $Na_2CO_3$ (50 mL) and $CH_2Cl_2$ (100 mL). The aqueous layer was extracted further with $CH_2Cl_2$ (2×100 mL), then with EtOAc (3×100 mL). The combined organic extracts were dried over $Na_2SO_4$, filtered, and concentrated in vacuo. The crude product was purified by flash column chromatography on silica, eluting with a gradient of 1% to 5% MeOH-0.1% to 0.5% $NH_4OH$—$CH_2Cl_2$ to yield the desired product which was converted to the hydrochloride salt by treatment with HCl in EtOAc.

Elemental analysis calculated for $C_{24}H_{19}N_5O_2 \cdot 2$ HCl·1.55 $CH_3OH$: C: 57.68; H: 5.15; N: 13.16 Found: C: 57.69; H: 5.02; N: 13.07

FAB MS: 410 ($MH^+$).

Example 5

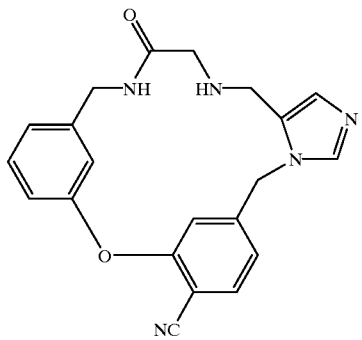

19,20,21,22-Tetrahydro-19-oxo-17H-6,10:12,16-dimetheno-16H-imidazo[3,4-h][1,8,11,14] oxatriazacycloeicosine-9-carbonitrile Step A: 3-Benzyloxybenzyl azide To a stirred solution of 3-benzyloxybenzyl alcohol (5.0 g, 23.3 mmol) and diphenylphosphoryl azide (7.7 g, 28.0 mmol) in dry toluene (40 mL) at 0° C., was added 1,8-diazabicyclo[5.4.0]undec-7-ene (3.9 g, 25.6 mmol). The resulting mixture was allowed to warm to ambient temperature, and stirred under argon for 18 hrs, then washed with water (2×15 mL), then 5% hydrochloric acid (15 mL). The organic layer was dried over $MgSO_4$, filtered, and concentrated in vacuo. The crude product was purified by flash column chromatography on silica, eluting with hexane –4% ethyl acetate to yield the product as a colorless oil.

Step B: 3-Benzyloxybenzylamine

3-Benzyloxybenzyl azide, as described above in Step A, (5.0 g, 20.9 mmol) was dissolved in dry THF (100 mL) and the solution was cooled to –70° C. Lithium aluminum hydride (31.4 mL of a 1.0 M solution in THF, 31.4 mmol) was added dropwise, then the reaction mixture was warmed to 0° C. and stirred for 30 min. The reaction was quenched with EtOAc (1.2 mL), then water (1.2 mL), then 15% NaOH (1.2 mL), and finally water (3.6 mL). The resulting mixture was filtered, concentrated under reduced pressure and purified by flash column chromatography on silica, eluting with $CH_2Cl_2$-3% MeOH –0.3% $NH_4OH$, to yield the titled product as a colorless oil.

19,20,21,22-Tetrahydro-19-oxo-17H-6,10:12,16-dimetheno-16H-imidazo[3,4-h][1,8,11,14]oxatriazacycloeicosine-9-carbonitrile Following the procedure described in Example 4, but using 3-benzyloxybenzylamine (as described in Example 5, Step B) in place of 1-amino-7-benzyloxynaphthalene in Step K, the above compound was prepared.

Elemental analysis calculated for $C_{21}H_{19}N_5O_2 \cdot 0.6$ MeOH·0.4 $H_2O$: C: 64.88; H: 5.60; N: 17.52 Found: C: 64.91; H: 5.23; N: 17.52

FAB MS: 374 (MH$^+$).

Example 6

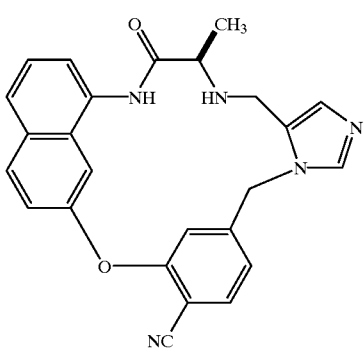

(20R)-19,20,21,22-Tetrahydro-20-methyl-19-oxo-5H-12,14-etheno-6,10-metheno-18H-benz[d]imidazo[4,3-k][1,6,9,12]oxatriazacyclo-octadecine-9-carbonitrile trifluoroacetate Step A: 8-(tert-Butoxycarbonylamino)-2-naphthol A mixture of 8-amino-2-naphthol (50.6 g, 0.318 mol) and di-tert-butyl dicarbonate (72.8 g, 0.334 mol) in $CH_2Cl_2$ (1.4 L) and THF (1 L) was heated to reflux for 36 hrs. The mixture was allowed to cool to ambient temperature, then filtered and concentrated in vacuo. The residue was purified by flash column chromatography on silica, eluting with a gradient of $CH_2Cl_2$-0 to 10% ethyl acetate to yield the desired product as a light brown solid.

Step B: 1-(tert-Butoxycarbonylamino)-7-(tert-butyldiphenylsilyloxy)naphthalene

A mixture of 8-(tert-butoxycarbonylamino)-2-naphthol, as described above in Step A, (35 g, 0.135 mol), tert-butyldiphenylsilyl chloride (40.9 g, 0.149 mmol), and imidazole (18.4 g, 0.270 mmol) in dry, degassed DMF (300 mL) was stirred, under argon, at 50° C. for 18 hrs. The solvent was removed under reduced pressure and the residue was partitioned between saturated aqueous $NaHCO_3$ (500 mL) and EtOAc (1 L). The aqueous layer was extracted further with EtOAc (300 mL) and the combined organic extracts were dried over $Na_2SO_4$, filtered, and concentrated in vacuo. The crude product was purified by flash column chromatography on silica, eluting with a gradient of hexane −25% to 45% $CH_2Cl_2$ to yield the desired product as a pale solid.

Step C: 1-Amino-7-(tert-butyldiphenylsilyloxy)naphthalene hydrochloride

A solution of 1-(tert-butoxycarbonylamino)-7-(tert-butyldiphenylsilyloxy)naphthalene, as described above in Step B, (1.54 g, 3.09 mmol) in EtOAc (80 mL) and $Et_2O$ (20 mL) at ambient temperature was saturated with HCl (g). After 1 hr, the mixture was concentrated in vacuo to yield the desired product as a pale solid.

Step D: (R)-2-(tert-Butoxycarbonylamino)-N-[7-(tert-butyldiphenylsilyloxy)naphthalen-1-yl]propionamide To (R)-N-(tert-butoxycarbonyl)alanine (220 mg, 1.16 mmol) in dry $CH_2Cl_2$ (2 mL) under argon were added PYBOP (604 mg, 1.16 mmol), 1-amino-7-(tert-butyldiphenylsilyloxy)naphthalene hydrochloride, as described above in Step C, (250 mg, 0.58 mmol), and N,N-diisopropylethylamine (0.40 mL, 2.3 mmol). The reaction mixture was stirred for 3 hrs, then partitioned between $CH_2Cl_2$ (250 mL) and 10% aqueous citric acid (75 mL). The organic layer was dried over $Na_2SO_4$, filtered, and concentrated in vacuo. The residue was purified by flash column chromatography on silica, eluting with $CH_2Cl_2$-20% ethyl acetate to yield the desired product as a white foam.

Step E: (R)-2-(tert-Butoxycarbonylamino)-N-(7-hydroxynaphthalen-1-yl)propionamide To a solution of (R)-2-(tert-butoxycarbonylamino)-N-[7-(tert-butyldiphenylsilyloxy)naphthalen-1-yl]propionamide (290 mg, 0.51 mmol) in dry THF (2 mL), under argon, was added TBAF (0.56 mL of a 1.0 M solution in THF, 0.56 mmol) dropwise. The resulting mixture was stirred at ambient temperature for 30 min, then saturated aqueous $NaHCO_3$ (1 mL) was added and the THF was removed under reduced pressure. The residue was partitioned between saturated aqueous $NaHCO_3$ (10 mL) and $CH_2Cl_2$ (30 mL). The aqueous layer was extracted further with $CH_2Cl_2$ (30 mL) and the combined organic extracts were dried over $Na_2SO_4$, filtered, and concentrated in vacuo. The crude product was purified by flash column chromatography on silica, eluting with a gradient of $CH_2Cl_2$-10% to 30% EtOAc to yield the titled product as a pale solid.

Step F: (20R)-19,20,21,22-Tetrahydro-20-methyl-19-oxo-5H-12,14-etheno-6,1 0-metheno-1 8H-benz[d]imidazo[4,3-k][1,6,9,12]oxatriazacyclo-octadecine-9-carbonitrile trifluoroacetate Following the procedure described in Example 4, but using (R)-2-(tert-butoxycarbonylamino)-N-(7-hydroxynaphthalen-1-yl)propionamide (as described in Example 6, Step E) in place of (tert-butoxycarbonylamino)-N-(7-hydroxynaphthalen-1-yl)acetamide in Step M, and purifying the final product by HPLC on a reversed phase C18 column, eluting with a gradient of 0.1% aqueous TFA −5% to 95 % 0.1% TFA/$CH_3CN$, the above compound was prepared.

Elemental analysis calculated for $C_{25}H_{21}N_5O_2 \cdot 2 CF_3CO_2H \cdot 0.9 CH_2Cl_2 \cdot 0.9 H_2O$: C: 52.79; H: 3.94; N: 10.30 Found: C: 52.81; H: 3.95; N: 10.63

FAB MS: 424 (MH$^+$).

Example 7

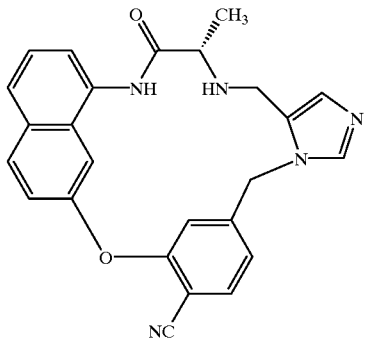

(20S)-19,20,21,22-Tetrahydro-20-methyl-19-oxo-5H-12,14-etheno-6,10-metheno-18H-benz[d]imidazo[4,3-k][1,6,9,12]oxatriazacyclo-octadecine-9-carbonitrile hydrochloride Following the procedure described in Example 6, but using (S)-N-(tert-butoxycarbonyl)alanine in place of (R)-N-

(tert-butoxycarbonyl)alanine in Step D, and converting the final product to the hydrochloride salt, the above compound was prepared.

Elemental analysis calculated for $C_{25}H_{21}N_5O_2 \cdot 2$ HCl·0.75 $CH_2Cl_2$·1.95 $H_2O$: C: 51.96; H: 4.81; N: 11.77 Found: C: 51.95; H: 4.81; N: 12.11
FAB MS: 424 (MH⁺).

Example 8

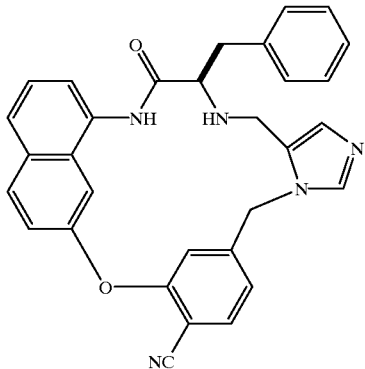

(20R)-20-Benzyl-19,20,21,22-tetrahydro-19-oxo-5H-12,14-etheno-6,10-metheno-18H-benz[d]imidazo[4,3-k][1,6,9,12]oxatriazacyclo-octadecine-9-carbonitrile trifluoroacetate Following the procedure described in Example 6, but using (R)-N-(tert-butoxycarbonyl)phenylalanine in place of (R)-N-(tert-butoxycarbonyl)alanine in Step D, the above compound was prepared.

Elemental analysis calculated for $C_{31}H_{25}N_5O_2 \cdot 2$ $CF_3CO_2H \cdot 0.15$ $H_2O$: C: 57.56; H: 3.77; N: 9.59 Found: C: 57.59; H: 4.13; N: 9.77
FAB MS: 500 (MH⁺).

Example 9

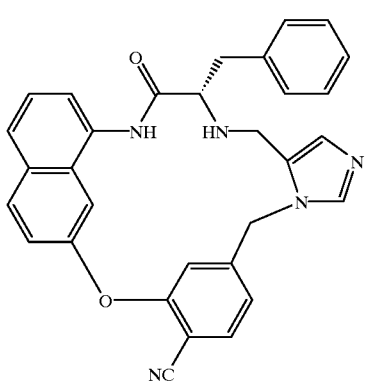

(20S)-20-Benzyl-19,20,21,22-tetrahydro-19-oxo-5H-12,14-etheno-6,10-metheno-18H-benz[d]imidazo[4,3-k][1,6,9,12]oxatriazacyclo-octadecine-9-carbonitrile trifluoroacetate Following the procedure described in Example 6, but using (S)-N-(tert-butoxycarbonyl)phenylalanine in place of (R)-N-(tert-butoxycarbonyl)alanine in Step D, the above compound was prepared. Elemental analysis calculated for $C_{31}H_{25}N_5O_2 \cdot 2$ $CF_3CO_2H \cdot 1.4$ $H_2O$: C: 55.83; H: 3.99; N: 9.30 Found: C: 55.82; H: 4.08; N: 9.03
FAB MS: 500 (MH⁺).

Example 10

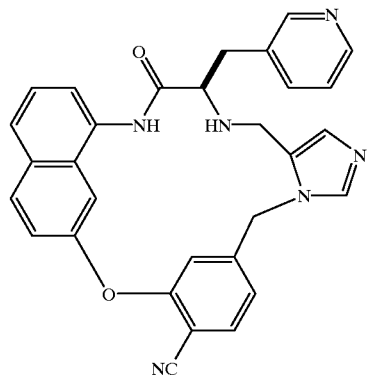

(20R)-19,20,21,22-Tetrahydro-19-oxo-20-(3-pyridylmethyl)-5H-12,14-etheno-6,10-metheno-18H-benz[d]imidazo[4,3-k][1,6,9,12]oxatriaza-cyclooctadecine-9-carbonitrile hydrochloride Following the procedure described in Example 6, but using (R)-N-(tert-butoxycarbonyl)-3-(3-pyridyl)alanine in place of (R)-N-(tert-butoxycarbonyl)alanine in Step D, and converting the final product to the hydrochloride salt, the above compound was prepared.

Elemental analysis calculated for $C_{30}H_{24}N_6O_2 \cdot 3$ HCl·0.75 $H_2O$·0.5 $CH_2Cl_2$: C: 55.01; H: 4.47; N: 12.62 Found: C: 55.02; H: 4.49; N: 12.48
FAB MS: 501 (MH⁺).

Example 11

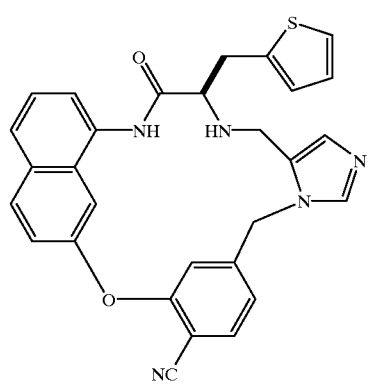

(20R)-19,20,21,22-Tetrahydro-19-oxo-20-(thiophen-2-ylmethyl)-5H-12,14-etheno-6,10-metheno-18H-benz[d]imidazo[4,3-k][1,6,9,12]oxatriazacyclooctadecine-9-carbonitrile hydrochloride Following the procedure described in Example 6, but using (R)-N-(tert-butoxycarbonyl)-3-(thiophen-2-yl)alanine in place of (R)-N-(tert-butoxycarbonyl)alanine in Step D, and converting the final product to the hydrochloride salt, the above compound was prepared.

Elemental analysis calculated for $C_{29}H_{23}N_5O_2S \cdot 2$ $HCl \cdot 0.1\ H_2O \cdot 0.95\ CH_2Cl_2$: C: 54.42; H: 4.13; N: 10.60 Found: C: 54.38; H: 4.11; N: 10.69

FAB MS: 506 (MH$^+$).

Example 12

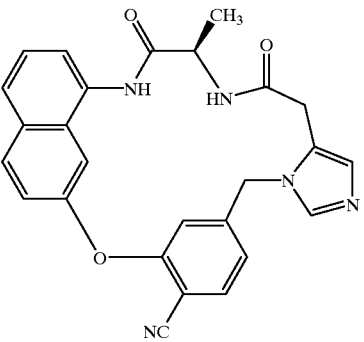

(20R)-19,20,22,23-Tetrahydro-20-methyl-19,22-dioxo-5H,21H-12,14-etheno-6,10-methenobenz[d]imidazo[4,3-l][1,6,9,13]oxatriazacyclononadecine-9-carbonitrile trifluoroacetate Step A: Methyl (imidazol-4-yl)acetate hydrochloride A solution of 4-imidazoleacetic acid hydrochloride (4.00 g, 24.6 mmol) in MeOH (100 mL) was saturated with HCl (g). Trimethyl orthoformate (10 mL, 91 mmol) was added and the mixture was stood at ambient temperature for 18 hrs, then concentrated to dryness in vacuo to afford the titled ester as a white solid.

Step B: Methyl [1-(triphenylmethyl)-1H-imidazol-4-yl]acetate

To a solution of methyl 4-imidazoleacetate hydrochloride, as described above in Step A, (4.30 g, 24.3 mmol) in dry DMF (50 mL) were added triethylamine (7.45 mL, 53.5 mmol), then triphenylmethyl bromide (8.64 g, 26.7 mmol). The mixture was stirred at ambient temperature for 18 hrs, then partitioned between $H_2O$ (250 mL) and EtOAc (250 mL). The organic layer was dried over $Na_2SO_4$, filtered and concentrated under reduced pressure. The residue was purified by flash column chromatography on silica, eluting with ethyl acetate, to yield the product as a pale solid.

Step, C: Methyl [1-(4-cyano-3-fluorobenzyl)-1H-imidazol-5-yl]acetate hydrobromide A mixture of methyl [1-(triphenylmethyl)-1H-imidazol-4-yl]acetate, as described above in Step B, (536 mg, 1.40 mmol) and 4-cyano-3-fluorobenzyl bromide, as described in Example 1, Step D, (300 mg, 1.40 mmol) in acetonitrile (3 mL) was heated to 50° C. for 2 hrs. The mixture was allowed to cool, and the solid collected by filtration. The acetonitrile filtrate was concentrated in vacuo to a volume of approximately 1 mL and then reheated to 50° C. for 2 hrs, cooled, and the solid removed by filtration. The two crops of precipitated imidazolium salts were combined in MeOH (30 mL) and the solution was heated to reflux for 2 hrs, then concentrated in vacuo. The residue was partitioned between saturated aqueous $NaHCO_3$ (20 mL) and $CHCl_3$ (30 mL). The aqueous layer was extracted further with $CHCl_3$ (2×15 mL). The combined organic extracts were dried over $Na_2SO_4$, filtered, and concentrated in vacuo. The crude product was purified by flash column chromatography on silica, eluting with $CHCl_3$-3% MeOH –0.3% $NH_4OH$ to $CHCl_3$-5% MeOH –0.5% $NH_4OH$ to yield the titled product as a white solid.

Step D: Lithium [1-(4-cyano-3-fluorobenzyl)-1H-imidazol-5-yl]acetate

Methyl [1-(4-cyanobenzyl)-1H-imidazol-5-yl]acetate, as described above in Step C, (free base) (260 mg, 0.95 mmol) was dissolved in THF (5 mL) and $H_2O$ (1 mL). Lithium hydroxide (40 mg, 0.95 mmol) was added and the resulting mixture was stirred at ambient temperature for 1 hr, then adjusted to pH 7 with 1.0 N aqueous HCl and concentrated to dryness in vacuo to give the titled lithium salt.

Step E: (R)-2-{2-[3 -(4-Cyano-3-fluorobenzyl)-3H-imidazol-4-yl]acetylamino}-N-(7-hydroxynaphthalen-1-yl) propionamide trifluoroacetate A mixture of lithium [1-(4-cyano-3-fluorobenzyl)-1H-imidazol-5-yl]acetate, as described above in Step D, (53 mg, 0.20 mmol), (R)-2-amino-N-( 7- hydroxynaphthalen-1-yl) propionamide hydrochloride, as described in Example 6 (55 mg, 0.21 mmol), and PYBOP (107 mg, 0.21 mmol), was stirred in DMF (0.5 mL) at ambient temperature and N,N-diisopropylethylamine (0.090 mL, 0.52 mmol) was added. The reaction mixture was stirred for 3 hrs. The solvent was removed under reduced pressure and the residue was purified by HPLC on a reversed phase C18 column, eluting with a gradient of 0.1% aqueous TFA-5% to 95% 0.1% TFA/$CH_3CN$, to provide the titled compound.

Step F: (20R)-19,20,22,23-Tetrahydro-20-methyl-19,22-dioxo-5H,21H-12,14-etheno-6,10-methenobenz[d]imidazo[4,3-l][1,6,9,13]-oxatriazacyclononadecine-9-carbonitrile trifluoroacetate A mixture of (R)-2-{2-[3-(4-cyano-3-fluorobenzyl)-3H-imidazol-4-yl]acetylamino}-N-(7-hydroxynaphthalen-1-yl) propionamide trifluoroacetate, as described above in Step E, (59 mg, 0.10 mmol) and $Cs_2CO_3$ (115 mg, 0.35 mmol) in dry DMF (15 mL) was stirred at 65° C. under argon for 6 hrs. The solvent was removed under reduced pressure and the residue was purified by HPLC on a reversed phase C18 column, eluting with a gradient of 0.1 % aqueous TFA-5% to 95% 0.1% TFA/$CH_3\ CN$, to provide the titled compound.

Elemental analysis calculated for $C_{26}H_{21}N_5O_3 \cdot CF_3CO_2H \cdot 1.85\ H_2O \cdot 0.85\ CH_2Cl_2$: C: 54.22; H: 4.32; N: 10.96 Found: C: 54.24; H: 4.32; N: 10.71

FAB MS: 452 (MH$^+$).

Example 13

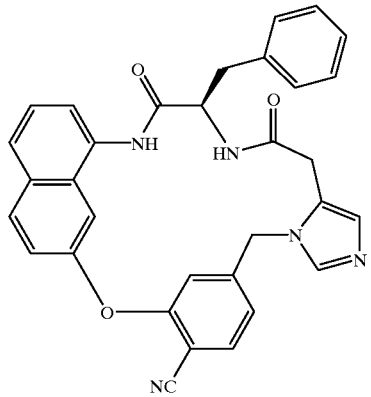

(20R)-20-Benzyl-19,20,22,23-tetrahydro-19,22-dioxo-5H,21H-12,14-etheno-6,10-methenobenz[d]imidazo[4,3-l][1,6,9,13]oxatriazacyclononadecine-9-carbonitrile hydrochloride Following the procedure described in Example 12, but using (R)-2-amino-N-(7-hydroxynaphthalen-1-yl)-3- phenylpropionamide hydrochloride in place of (R)-2-amino-N-(7-hydroxynaphthalen-1-yl)propionamide hydrochloride in Step E, and converting the final product to the hydrochloride salt, the above compound was prepared.

Elemental analysis calculated for $C_{32}H_{25}N_5O_3 \cdot HCl \cdot 0.15$ $CH_2Cl_2$: C: 66.94; H: 4.60; N: 12.14 Found: C: 67.06; H: 4.53; N: 11.85

FAB MS: 528 (MH$^+$).

Example 14

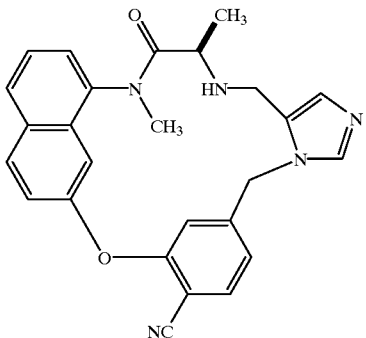

(20R)-19,20,21,22-Tetrahydro-18,20-dimethyl-19-oxo-5H-12,14-etheno-6,10-metheno-18H-benz[d]imidazo[4,3-k][1,6,9,12]oxatriaza-cyclooctadecine-9-carbonitrile hydrochloride Step A: 1-(tert-Butoxycarbonylamino)-7-[(2-methoxyethoxy)methoxy]naphthalene To a solution of 8-(tert-butoxycarbonylamino)-2-naphthol, as described in Example 6, Step A, (1.80 g, 6.94 mmol) in dry THF (50 mL), at 0° C., under argon, was added NaH (305 mg of a 60% oil dispersion, 7.64 mmol). The resulting mixture was stirred for 30 min, then 2-methoxyethoxymethyl chloride (0.95 mL, 8.33 mmol) was added. The mixture was allowed to warm slowly and then stirred at ambient temperature for 18 hrs. The reaction mixture was poured into saturated aqueous $NH_4Cl$ (100 mL) and $CH_2Cl_2$ (250 mL). The organic layer was dried over $Na_2SO_4$, filtered, and concentrated in vacuo. The crude product was purified by flash column chromatography on silica, eluting with a gradient of hexane −20% to 50% EtOAc to yield the desired product as a colorless oil.

Step B: 7-[(2-Methoxyethoxy)methoxy]-1-(methylamino)-naphthalene

A mixture of 1-(tert-butoxycarbonylamino)-7-[(2-methoxyethoxy)methoxy]naphthalene, as described above in Step A, (1.59 g, 4.58 mmol) and LAH (11.4 mL of a 1.0 M solution in THF, 11.4 mmol) in dry THF (100 mL) was heated to 65° C., under argon. After 70 min, the reaction mixture was cooled to ambient temperature and quenched with saturated aqueous $NH_4Cl$ (5 mL). Most of the THF was removed by concentration under reduced pressure, and the residual mixture was partitioned between water (500 mL) and $CH_2Cl_2$ (250 mL). The aqueous layer was extracted further with $CH_2Cl_2$ (250 mL). The combined organic extracts were dried over $Na_2SO_4$, filtered, and concentrated in vacuo. The crude product was purified by flash column chromatography on silica, eluting with hexane −25% EtOAc to yield the titled product.

Step C: (R)-2-(tert-Butoxycarbonylamino)-N-{7-[(2-methoxyethoxy)methoxy]naphthalen-1-yl}-N-methylpropionamide To (R)-N-(tert-butoxycarbonyl)alanine (1.09 g, 5.78 mmol) in dry $CH_2Cl_2$ (4 mL) under argon were added PYBOP (3.01 g, 5.78 mmol), 7-[(2-methoxyethoxy)methoxy]-1-(methylamino)naphthalene, as described above in Step B, (302 mg, 1.16 mmol), and N,N-diisopropylethylamine (1.00 mL, 5.75 mmol). The reaction mixture was stirred for 48 hrs, then partitioned between $CH_2Cl_2$ (500 mL) and 10% aqueous citric acid (150 mL). The organic layer was dried over $Na_2SO_4$, filtered, and concentrated in vacuo. The residue was purified by flash column chromatography on silica, eluting with a gradient of hexane −10% to 60% EtOAc to yield the desired product.

Step D: (R)-2-Amino-N-(7-hydroxynaphthalen-1-yl)-N-methylpropionamide hydrochloride A solution of (R)-2-(tert-butoxycarbonylamino)-N-{7-[(2-methoxyethoxy)methoxy]naphthalen-1-yl}-N-methylpropionamide, as described above in Step C, (255 mg, 0.59 mmol) in EtOAc (10 mL) at ambient temperature was saturated with HCl (g). After 1 hr, the mixture was concentrated in vacuo to yield the titled product as a pale solid.

Step E: (R)-2-{[3-(4-Cyano-3-fluorobenzyl)-3H-imidazol-4-ylmethyl]amino}-N-(7-hydroxynaphthalen-1-yl)-N-methylpropionamide (R)-2-Amino-N-(7-hydroxynaphthalen-1yl)-N-methylpropionamide hydrochloride, as described above in Step D, (109 mg, 0.39 mmol) and 1-(4-cyano-3-fluorobenzyl)-5-imidazolecarboxaldehyde, as described in Example 4, Step G, (89 mg, 0.39 mmol), were stirred in MeOH (2 mL) and was neutralized with N,N-diisopropylethylamine. Acetic acid was then added dropwise to adjust the mixture to ca. pH 5, as judged by wetted pH paper. The mixture was stirred for 1 hr at ambient temperature, then $NaCNBH_3$ (32 mg, 0.51 mmol) was added, the solution was readjusted to ca. pH 5 by addition of AcOH, and stirring was continued for 18 hrs. The reaction was quenched with saturated aqueous $NaHCO_3$ (2 mL) and most of the MeOH was removed under reduced pressure. The residual solution was partitioned between saturated aqueous $NaHCO_3$ (10 mL) and $CH_2Cl_2$ (20 mL). The aqueous layer was extracted further with $CH_2Cl_2$ (2×20 mL). The combined organic extracts were dried over $Na_2SO_4$, filtered, and concentrated in vacuo. The crude product was purified by flash column chromatography on silica, eluting with a gradient of 1% to 6% MeOH −0.1% to 0.6% $NH_4OH$ —$CH_2Cl_2$ to yield the titled product.

Step F: 19,20,21,22-Tetrahydro-19-oxo-5H-12,14-etheno-6,10-metheno-18H-benz[d]imidazo[4,3-k][1,6,9,12]oxatriaza-cyclooctadecine-9-carbonitrile hydrochloride A mixture of (R)-2-{[3-(4-cyano-3-fluorobenzyl)-3H-imidazol-4-ylmethyl]amino}-N-(7-hydroxynaphthalen-1-yl)-N-methylpropionamide, as described above in Step E, (130 mg, 0.28 mmol) and $Cs_2CO_3$ (231 mg, 0.71 mmol) in dry, degassed DMF (40 mL) was stirred at 60° C. under argon for 18 hrs, then the solvent was removed under reduced pressure. The residue was partitioned between saturated aqueous $NaHCO_3$ (50 mL) and $CH_2Cl_2$ (100 mL). The aqueous layer was extracted further with $CH_2Cl_2$ (2×100 mL), then with EtOAc (3×100 mL),. The combined organic extracts were dried over $Na_2SO_4$, filtered, and concentrated in vacuo. The crude product was purified by flash column chromatography on silica, eluting with a gradient of 1% to 6% MeOH −0.1% to 0.6% $NH_4OH$ —$CH_2Cl_2$ to yield the desired product which was converted to the hydrochloride salt by treatment with HCl in EtOAc.

Elemental analysis calculated for $C_{26}H_{23}N_5O_2 \cdot 2$ HCl$\cdot$1.3 $H_2O \cdot 0.5$ EtOAc: C: 58.19; H: 5.51; N: 12.12 Found: C: 58.16; H: 5.33; N: 12.14

FAB MS: 438 (MH$^+$).

Example 15

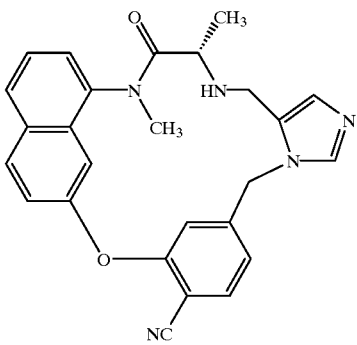

(20S)-19,20,21,22-Tetrahydro-18,20-dimethyl-19-oxo-5H-12,14-etheno-6,10-metheno-18H-benz[d]imidazo[4,3-k][1,6,9,12]oxatriazacyclooctadecine-9-carbonitrile hydrochloride Following the procedure described in Example 14, but using (S)-N-(tert-butoxycarbonyl)alanine in place of (R)-N-(tert-butoxycarbonyl)alanine in Step C, the above compound was prepared.

Elemental analysis calculated for $C_{26}H_{23}N_5O_2 \cdot 2$ HCl·0.65 EtOAc·1.1 H$_2$O: C: 58.46; H: 5.56; N: 11.92 Found: C: 58.48; H: 5.55; N: 11.88

FAB MS: 438 (MH$^+$).

Example 16

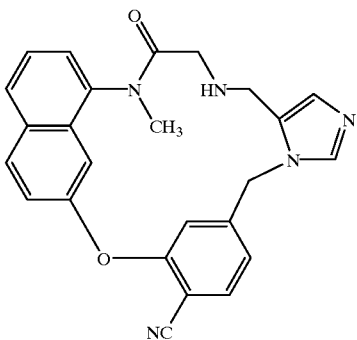

19,20,21,22-Tetrahydro-18-methyl-19-oxo-5H-12,14-etheno-6,10-metheno-18H-benz[d]imidazo[4,3-k][1,6,9,12]oxatriazacyclooctadecine-9-carbonitrile hydrochloride Following the procedure described in Example 14, but using N-(tert-butoxycarbonyl)glycine in place of (R)-N-(tert-butoxycarbonyl)alanine in Step C, the above compound was prepared.

Elemental analysis calculated for $C_{25}H_{21}N_5O_2 \cdot 2$ HCl·0.35 C$_6$H$_5$CH$_3$·1.55 H$_2$O:

C: 59.23; H: 5.23; N: 12.58 Found: C: 59.24; H: 4.94; N: 12.64

FAB MS: 424 (MH$^+$).

Example 17

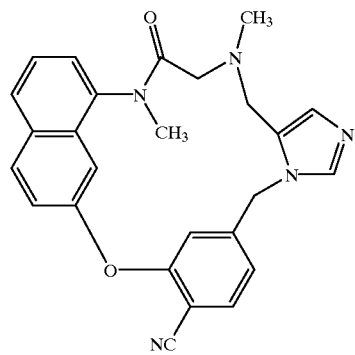

19,20,21,22-Tetrahydro-18,21-dimethyl-19-oxo-5H-12,14-etheno-6,10-metheno-18H-benz[d]imidazo[4,3-k][1,6,9,12]oxatriazacyclooctadecine-9-carbonitrile hydrochloride Step A: 19,20,21,22-Tetrahydro-18,21-dimethyl-19-oxo-5H-12,14-etheno-6,10-metheno-18H-benz[d]imidazo[4,3-k][1,6,9.12]oxatriazacyclooctadecine-9-carbonitrile hydrochloride A mixture of 19,20,21,22-tetrahydro-18-methyl-19-oxo-5H-12,14-etheno-6,10-metheno-18H-benz [d]imidazo [4,3-k][1,6,9,12]oxatriazacyclooctadecosine-9-carbonitrile hydrochloride, as described in Example 16, (50 mg, 0.10 mmol) and formaldehyde (0.024 mL of a 37 wt % aqueous solution, 0.30 mmol), were stirred in MeOH (1 mL) and was neutralized with N,N-diisopropylethylamine. Acetic acid was then added dropwise to adjust the mixture to ca. pH 5, as judged by wetted pH paper. The mixture was stirred for 30 min at ambient temperature, then NaCNBH$_3$ (19 mg, 0.30 mmol) was added, the solution was readjusted to ca. pH 5 by addition of AcOH, and stirring was continued for 18 hrs. The reaction was quenched with saturated aqueous NaHCO$_3$ (1 mL) and most of the MeOH was removed under reduced pressure. The residual solution was partitioned between saturated aqueous NaHCO3 (5 mL) and CH$_2$Cl$_2$ (10 mL). The aqueous layer was extracted further with CH$_2$Cl$_2$ (2×10 mL). The combined organic extracts were dried over Na$_2$SO$_4$, filtered, and concentrated in vacuo. The crude product was purified by flash column chromatography on silica, eluting with a gradient of 1% to 4% MeOH –0.1% to 0.4% NH$_4$OH —CH$_2$Cl$_2$ to yield the desired product which was converted to the hydrochloride salt by treatment with HCl in EtOAc.

Elemental analysis calculated for $C_{26}H_{23}N_5O_2 \cdot 2$ HCl·0.45 EtOAc·2.5 H$_2$O: C: 56.10; H: 5.69; N: 11.77 Found: C: 55.94; H: 5.64; N: 11.78

FAB MS: 438 (MH$^+$).

Example 18

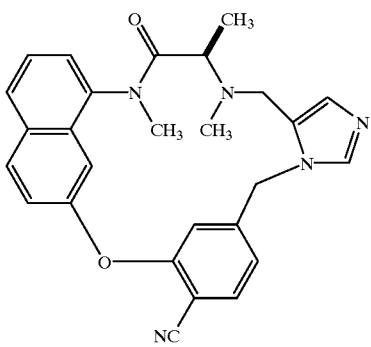

(20R)-19,20,21,22-Tetrahydro-18,20,21-trimethyl-19-oxo-5H-12,14-etheno-6,10-metheno-18H-benz[d]imidazo[4,3-k][1,6,9,12]oxatriazacyclooctadesine-9-carbonitrile hydrochloride Following the procedure described in Example 17, but using (20R)-19,20,21,22-tetrahydro-18,20-dimethyl-19-oxo-5H-12,14-etheno-6,10-metheno-18H-benz[d]imidazo[4,3-k][1,6,9,12]oxatriazacyclooctadecine-9-carbonitrile hydrochloride, as described in Example 14, in place of 19,20,21,22-tetrahydro-18-methyl-19-oxo-5H-12,14-etheno-6,10-metheno-18H-benz[d]imidazo[4,3-k][1,6,9,12]oxatriazacyclooctadecine-9-carbonitrile hydrochloride in Step A, the above compound was prepared.

Elemental analysis calculated for $C_{27}H_{25}N_5O_2 \cdot 2$ HCl$\cdot$0.65 EtOAc$\cdot$1.65 H$_2$O: C: 58.14; H: 5.85; N: 11.45 Found: C: 58.13; H: 5.90; N: 11.49

FAB MS: 452 (MH$^+$).

Example 19

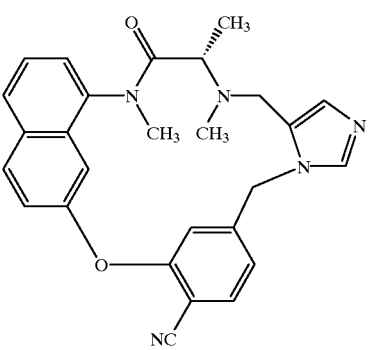

(20S)-19,20,21,22-Tetrahydro-18,20,21-trimethyl-19-oxo-5H-12,14-etheno-6,10-metheno-18H-benz[d]imidazo[4,3-k][1,6,9,12]oxatriazacyclooctadecine-9-carbonitrile hydrochloride Following the procedure described in Example 17, but using (20S)-19,20,21,22-tetrahydro-18,20-dimethyl-19-oxo-5H-12,14-etheno-6,10-metheno-18H-benz[d]imidazo[4,3-k][1,6,9,12]oxatriazacyclooctadecine-9-carbonitrile hydrochloride, as described in Example 15, in place of 19,20,21,22-tetrahydro-18-methyl-19-oxo-5H-12,14-etheno-6,10-metheno-18H-benz[d]imidazo[4,3-k][1,6,9,12]oxatriazacyclooctadecine-9-carbonitrile hydrochloride in Step A, the above compound was prepared.

Elemental analysis calculated for $C_{27}H_{25}N_5O_2 \cdot 2$ HCl$\cdot$0.2 EtOAc$\cdot$2.35 H$_2$O: C: 57.13; H: 5.74; N: 11.98 Found: C: 57.15; H: 5.36; N: 11.82

FAB MS: 452 (MH$^+$).

Example 20

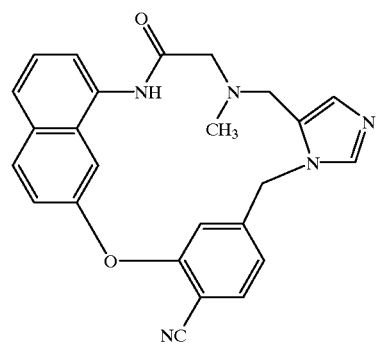

19,20,21,22-Tetrahydro-21-methyl-19-oxo-5H-12,14-etheno-6,10-metheno-18H-benz[d]imidazo[4,3-k][1,6,9,12]oxatriazacyclooctadecine-9-carbonitrile trifluoroacetate Following the procedure described in Example 17, but using 19,20,21,22-tetrahydro-19-oxo-5H-12,14-etheno-6,10-metheno-18H-benz[d]imidazo[4,3-k][1,6,9,12]oxatriazacyclooctadecine-9-carbonitrile hydrochloride, as described in Example 4, in place of 19,20,21,22-tetrahydro-18-methyl-19-oxo-5H-12,14-etheno-6,10-metheno-18H-benz[d]imidazo[4,3-k][1,6,9,12]oxatriazacyclo-octadecine-9-carbonitrile hydrochloride in Step A, and purifying the final product by HPLC on a reversed phase C18 column, eluting with a gradient of 0.1% aqueous TFA –5% to 95% 0.1% TFA/CH$_3$CN, the above compound was prepared.

Elemental analysis calculated for $C_{25}H_{21}N_5O_2 \cdot 2$ CF$_3$CO$_2$H$\cdot$1.15 H$_2$O: C: 51.81; H: 3.79; N: 10.42 Found: C: 51.82; H: 3.82; N: 10.27

FAB MS: 424 (MH$^+$).

Example 21

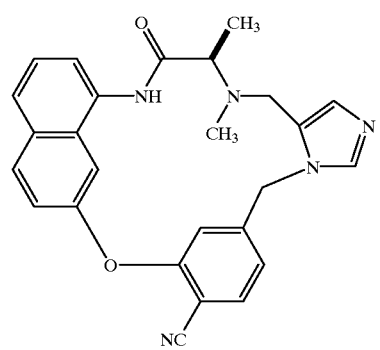

(20R)-19,20,21,22-Tetrahydro-20,21-dimethyl-19-oxo-5H-12,14-etheno-6,10-metheno-18H-benz[d]imidazo[4,3-k][1,6,9,12]oxatriazacyclooctadecine-9-carbonitrile trifluoroacetate Following the procedure described in Example 17, but using (20R)-19,20,21,22-tetrahydro-20-methyl-19-oxo-5H-

12,14-etheno-6,10-metheno-18H-benz[d]imidazo[4,3-k][1,6,9,12]oxatriazacyclooctadecine-9-carbonitrile trifluoroacetate, as described in Example 6, in place of 19,20,21,22-tetrahydro-18-methyl-19-oxo-5H-12,14-etheno-6,10-metheno-18H-benz[d]imidazo[4,3-k][1,6,9,12] oxatriazacyclooctadecine-9-carbonitrile hydrochloride in Step A, and purifying the final product by HPLC on a reversed phase C18 column, eluting with a gradient of 0.1 % aqueous TFA –5% to 95 % 0.1% TFA/CH₃CN, the above compound was prepared.

Elemental analysis calculated for $C_{26}H_{23}N_5O_2 \cdot 2 CF_3CO_2H \cdot 2.5 H_2O$: C: 50.70; H: 4.26; N: 9.86 Found: C: 50.73; H: 4.16; N: 9.52

FAB MS: 438 (MH⁺).

Example 22

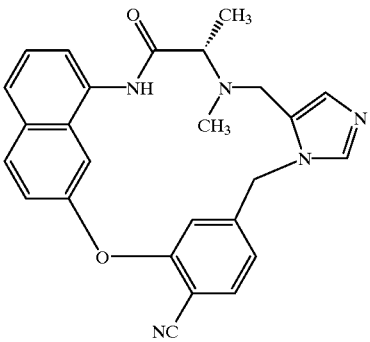

(20S)-19,20,21,22-Tetrahydro-20,21-dimethyl-19-oxo-5H-12,14-etheno-6,10-metheno-18H-benz[d]imidazo[4,3-k][1,6,9,12]oxatriazacyclooctadecine-9-carbonitrile trifluoroacetate Following the procedure described in Example 17, but using (20S)-19,20,21,22-Tetrahydro-20-methyl-19-oxo-5H-12,14-etheno-6,10-metheno-18H-benz[d]imidazo[4,3-k][1,6,9,12]oxatriazacyclooctadecine-9-carbonitrile hydrochloride, as described in Example 7, in place of 19,20,21,22-tetrahydro-18-methyl-19-oxo-5H-12,14-etheno-6,10-metheno-18H-benz[d]imidazo [4,3-k][1,6,9,12]oxatriazacyclooctadecine-9-carbonitrile hydrochloride in Step A, and purifying the final product by HPLC on a reversed phase C18 column, eluting with a gradient of 0.1% aqueous TFA –5% to 95% 0.1% TFA/CH₃CN, the above compound was prepared.

Elemental analysis calculated for $C_{26}H_{23}N_5O_2 \cdot 2 CF_3CO_2H \cdot 1.9 H_2O$: C: 51.81; H: 3.79; N: 10.42 Found: C: 51.82; H: 3.82; N: 10.27

FAB MS: 438 (MH⁺).

Example 23

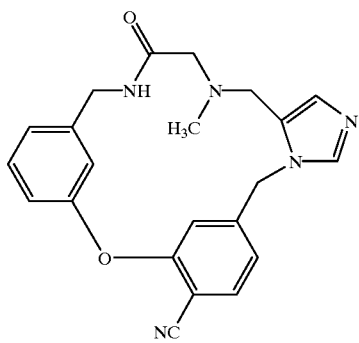

19,20,21,22-Tetrahydro-21-methyl-19-oxo-17H-6,10:12,16-dimetheno-16H-imidazo[3,4-h][1,8,11,14]oxatriazacycloeicosine-9-carbonitrile trifluoroacetate Following the procedure described in Example 17, but using 19,20,21,22-tetrahydro-19-oxo-17H-6,10:12,16-dimetheno-1 6H-imidazo [3,4-h][1,8,11,14] oxatriazacycloeicosine-9-carbonitrile, as described in Example 5, in place of 19,20,21,22-tetrahydro-18-methyl-19-oxo-5H-12,14-etheno-6,10-metheno-18H-benz[d]imidazo[4,3-k][1,6,9,12]oxatriazacyclooctadecosine-9-carbonitrile hydrochloride in Step A, and purifying the final product by HPLC on a reversed phase C18 column, eluting with a gradient of 0.1% aqueous TFA –5% to 95% 0.1% TFA/CH₃CN, the above compound was prepared.

Elemental analysis calculated for $C_{22}H_{21}N_5O_2 \cdot 2 CF_3CO_2H \cdot 0.9 CH_2Cl_2 \cdot 0.1 H_2O$: C: 46.57; H: 3.63; N: 10.10 Found: C: 46.57; H: 3.55; N: 9.81

FAB MS: 388 (MH⁺).

Example 24

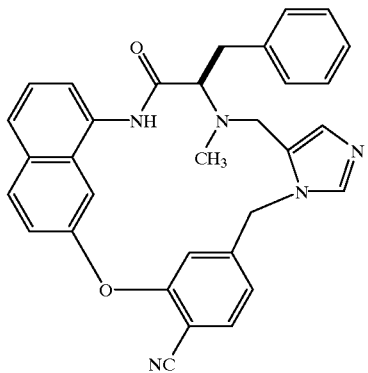

(20R)-20-Benzyl-19,20,21,22-tetrahydro-21-methyl-19-oxo-5H-12,14-etheno-6,10-metheno-18H-benz[d]imidazo[4,3-k][1,6,9,12]oxatriazacyclooctadecine-9-carbonitrile trifluoroacetate Following the procedure described in Example 17, but using (20R)-20-benzyl-19,20,21,22-tetrahydro-19-oxo-5H-12,14-etheno-6,10-metheno-18H-benz[d]imidazo[4,3k][1,6,9,12]oxatriazacyclooctadecine-9-carbonitrile trifluoroacetate, as described in Example 8, in place of 19,20,21,22-tetrahydro-18-methyl-19-oxo-5H-12,14-etheno-6,10-metheno-18H-benz[d]imidazo [4,3-k][1,6,9, 12]oxatriazacyclooctadecine-9-carbonitrile hydrochloride in Step A, and purifying the final product by HPLC on a reversed phase C18 column, eluting with a gradient of 0.1% aqueous TFA −5% to 95% 0.1% TFA/CH₃CN, the above compound was prepared.

Elemental analysis calculated for $C_{32}H_{27}N_5O_2 \cdot 1.45$ $CF_3CO_2H \cdot 1.5\ H_2O$: C: 59.37; H: 4.49; N: 9.92 Found: C: 59.39; H: 4.52; N: 9.59

FAB MS: 514 (MH⁺).

Example 25

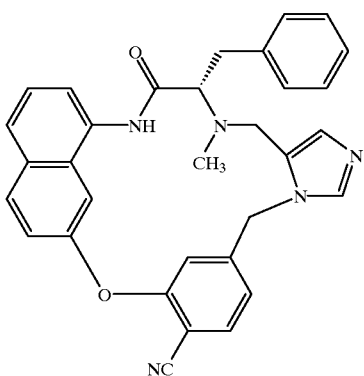

(20S)-20-Benzyl-19,20,21,22-tetrahydro-21-methyl-19-oxo-5H-12,14-etheno-6,10-metheno-18H-benz[d]imidazo[4,3-k][1,6,9,12]oxatriazacyclooctadecine-9-carbonitrile trifluoroacetate Following the procedure described in Example 17, but using (20S)-20-benzyl-19,20,21,22-tetrahydro-19-oxo-5H-12,14-etheno-6,10-metheno-18H-benz[d]imidazo[4,3k][1,6,9,12]oxatriazacyclo-octadecine-9-carbonitrile trifluoroacetate, as described in Example 9, in place of 19,20,21,22-tetrahydro-18-methyl-19-oxo-5H-12,14-etheno-6,10-metheno-18H-benz[d]imidazo[4,3-k][1,6,9,12]oxatriazacyclo-octadecine-9-carbonitrile hydrochloride in Step A, and purifying the final product by HPLC on a reversed phase C18 column, eluting with a gradient of 0.1% aqueous TFA −5% to 95% 0.1% TFA/CH₃CN, the above compound was prepared.

Elemental analysis calculated for $C_{32}H_{27}N_5O_2 \cdot 1.55$ $CF_3CO_2H \cdot 0.4\ H_2O$: C: 60.43; H: 4.24; N: 10.04 Found: C: 60.46; H: 4.49; N: 9.67

FAB MS: 514 (MH⁺).

Example 26

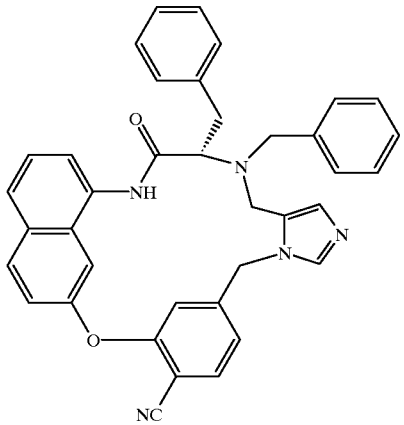

(20R)-20,21-Dibenzyl-19,20,21,22-tetrahydro-19-oxo-5H-12,14-etheno-6,10-metheno-18H-benz[d]imidazo[4,3-k][1,6,9,12]oxatriazacyclo-octadecine-9-carbonitrile trifluoroacetate Following the procedure described in Example 17, but using (20R)-20-benzyl-19,20,21,22-tetrahydro-19-oxo-5H-12,14-etheno-6,10-metheno-18H-benz[d]imidazo[4,3k][1,6,9,12]oxatriazacyclooctadecine-9-carbonitrile trifluoroacetate, as described in Example 9, in place of 19,20,21,22-tetrahydro-18-methyl-19-oxo-5H-12,14-etheno-6,10-metheno-18H-benz[d]imidazo[4,3-k][1,6,9,12]oxatriazacyclooctadecine-9-carbonitrile hydrochloride, and benzaldehyde in place of aqueous formaldehyde, in Step A, the above compound was prepared. The final product was purified by HPLC on a reversed phase C18 column, eluting with a gradient of 0.1% aqueous TFA −5% to 95% 0.1% TFA/CH₃CN.

Elemental analysis calculated for $C_{38}H_{31}N_5O_2 \cdot 1.2$ $CF_3CO_2H \cdot 0.65\ H_2O$: C: 65.72; H: 4.57; N: 9.49 Found: C: 65.71; H: 4.58; N: 9.40

FAB MS: 590 (MH⁺).

Example 27

(20S)-20,21-Dibenzyl-19,20,21,22-tetrahydro-19-oxo-5H-12,14-etheno-6,10-metheno-18H-benz[d]imidazo[4,3-k][1,6,9,12]oxatriazacyclo-octadecine-9-carbonitrile trifluoroacetate Following the procedure described in Example 17, but using (20S)-20-benzyl-19,20,21,22-tetrahydro-19-oxo-5H-

12,14-etheno-6,10-metheno-18H-benz[d]imidazo[4,3k][1, 6,9,12]oxatriazacyclooctadecine-9-carbonitrile trifluoroacetate, as described in Example 8, in place of 19,20,21,22-tetrahydro-18-methyl-19-oxo-5H-12,14-etheno-6,10-metheno-18H-benz[d]imidazo[4,3-k][1,6,9,12] oxatriazacyclooctadecine-9-carbonitrile hydrochloride, and benzaldehyde in place of aqueous formaldehyde, in Step A, the above compound was prepared. The final product was purified by HPLC on a reversed phase C1 8 column, eluting with a gradient of 0.1% aqueous TFA −5% to 95% 0.1% TFA/CH$_3$CN.

Elemental analysis calculated for C$_{38}$H$_{31}$N$_5$O$_2$•1.15 CF$_3$CO$_2$H•1.15 H$_2$O: C: 65.27; H: 4.68; N: 9.45 Found: C: 65.28; H: 4.72; N: 9.31

FAB MS: 590 (MH$^+$).

Example 28

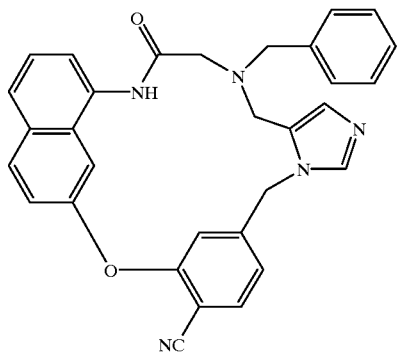

21-Benzyl-19,20,21,22-tetrahydro-19-oxo-5H-12, 14-etheno-6,10-metheno-18H-benz[d]imidazo[4,3-k] [1,6,9,12]oxatriazacyclo-octadecine-9-carbonitrile trifluoroacetate Following the procedure described in Example 17, but using 19,20,21,22-tetrahydro-19-oxo-5H-12,14-etheno-6, 10-metheno-18H-benz[d]imidazo[4,3-k][1,6,9,12] oxatriazacyclooctadecine-9-carbonitrile hydrochloride, as described in Example 4, in place of 19,20,21,22-tetrahydro-18-methyl-19-oxo-5H-12,14-etheno-6,10-metheno-18H-benz[d]imidazo[4,3-k][1,6,9,12]oxatriazacyclooctadecine-9-carbonitrile hydrochloride, and benzaldehyde in place of aqueous formaldehyde, in Step A, the above compound was prepared. The final product was purified by HPLC on a reversed phase C1 8 column, eluting with a gradient of 0.1 % aqueous TFA −5% to 95% 0.1% TFA/CH$_3$CN.

Elemental analysis calculated for C$_{31}$H$_{25}$N$_5$O$_2$•1.35 CF$_3$CO$_2$H•0.1 H$_2$O: C: 61.76; H: 4.08; N: 10.69 Found: C: 61.72; H: 4.04; N: 10.70

FAB MS: 500 (MH$^+$).

Example 29

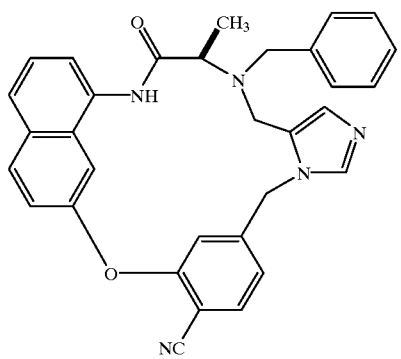

(20R)-21-Benzyl-19,20,21,22-tetrahydro-20-methyl-19-oxo-5H-12,14-etheno-6,10-metheno-18H-benz[d] imidazo [4,3-k][1,6,9,12]oxatriaza-cyclooctadecine-9-carbonitrile trifluoroacetate Following the procedure described in Example 17, but using (20R)-19,20,21,22-tetrahydro-20-methyl-19-oxo-5H-12,14-etheno-6,10-metheno-18H-benz[d]imidazo[4,3-k][1, 6,9,12]oxatriazacyclooctadecine-9-carbonitrile trifluoroacetate, as described in Example 6, in place of 19,20,21,22-tetrahydro-18-methyl-19-oxo-5H-12,14-etheno-6,10-metheno-18H-benz[d]imidazo [4,3-k][1,6,9, 12]oxatriazacyclooctadecine-9-carbonitrile hydrochloride, and benzaldehyde in place of aqueous formaldehyde, in Step A, the above compound was prepared. The final product was purified by HPLC on a reversed phase Cl$_{18}$ column, eluting with a gradient of 0. 1% aqueous TFA −5% to 95% 0.1% TFA/CH$_3$CN.

Elemental analysis calculated for C$_{32}$H$_{27}$N$_5$O$_2$•2 CF$_3$CO$_2$H•0.1 H$_2$O: C: 58.30; H: 3.94; N: 9.44 Found: C: 58.15; H: 4.09; N: 9.82

FAB MS: 514 (MH$^+$).

Example 30

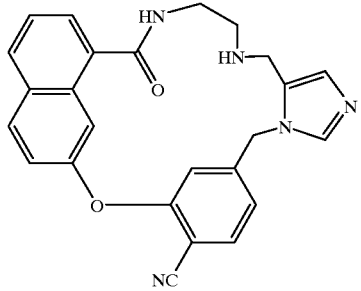

18,19,20,21,22,23-Hexahydro-18-oxo-5H-12,14-etheno-6,10-methenobenz[d]imidazo[4,3-i][1,7,10, 13]oxatriazacyclononadecine-9-carbonitrile hydrochloride Step A: 8-Iodo-2-naphthol 8-Amino-2-naphthol (5.0 g, 31.4 mmol) was dissolved in THF (25 mL) and 3 N aqueous HCl (50 mL) was added. The mixture was cooled to 0° C. then a solution of NaNO$_2$ (2.38 g, 34.5 mmol) in H$_2$O (10 mL) was added. The resulting mixture was stirred at 0° C. for 40 min, then a solution of KI (20.9 g, 126 mmol) in H$_2$O (15 mL) was added, and stirring

83 was continued for 30 min. The reaction mixture was extracted with EtOAc (2×200 mL). The combined organic extracts were washed with water (100 mL), then brine (100 mL), then dried over Na$_2$SO$_4$, filtered, and concentrated in vacuo. The residue was purified by flash column chromatography on silica, eluting with hexane –10% EtOAc to yield the desired product.

Step B: 7-(Triisopropylsilyloxy)-1-iodonaphthalene

To a solution of 8-iodo-2-naphthol, as described in Step A, (2.75 g, 10.2 mmol) in dry DMF (25 mL), under argon, were added imidazole (1.39 g, 20.4 mmol) and triisopropylsilyl chloride (2.55 g, 13.2 mmol). The resulting mixture was stirred at ambient temperature for 4 hrs, then quenched with 10% aqueous citric acid (100 mL) and extracted with EtOAc (2×100 mL). The combined organic extracts were washed with water (50 mL), then brine (50 mL), then dried over Na$_2$SO$_4$, filtered, and concentrated in vacuo. The residue was purified by flash column chromatography on silica, eluting with CH$_2$Cl$_2$-50% hexane to yield the desired product as a white solid.

Step C: 7-(Triisopropylsilyloxy)-1-naphthoic acid

To a solution of 7-(triisopropylsilyloxy)-1-iodonaphthalene, as described in Step B, (3.95 g, 9.26 mmol) in dry THF (60 mL) at –78° C., under argon, was added tert-butyllithium (10.9 mL of a 1.7 M solution in pentane, 18.53 mmol), dropwise. The resulting mixture was stirred at –78° C. for 1 hr, then an excess of CO$_2$ (g) was bubbled in over 5 min. The mixture was allowed to warm to ambient temperature and stirred for 18 hrs. The reaction mixture was poured into H$_2$O (100 mL) and EtOAc (200 mL). The aqueous layer was adjusted to pH=2–3 by addition of 1.0 N aqueous HCl, and the EtOAc layer was extracted, then dried over Na$_2$SO$_4$, filtered, and concentrated in vacuo to provide the titled compound, which was of sufficient purity to use in the next step.

Step D: N-[2-(tert-Butoxycarbonylamino)ethyl]-7-(triisopropylsilyloxy)naphthalene-1-carboxamide To 2-(tert-butoxycarbonylamino)ethylamine (70 mg, 0.44 mmol) in dry THF (1 mL) under argon were added PYBOP (226 g, 0.43 mmol), 7-(triisopropylsilyloxy)-1-naphthoic acid, as described in Step D, (148 mg, 0.43 mmol), and N,N-diisopropylethylamine (0.115 mL, 0.66 mmol). The reaction mixture was stirred for 4 hrs, then partitioned between CH$_2$Cl$_2$ (50 mL) and saturated aqueous NaHCO$_3$ (20 mL). The organic layer was dried over Na$_2$SO$_4$, filtered, and concentrated in vacuo. The residue was purified by flash column chromatography on silica, eluting with a gradient of CH$_2$Cl$_2$ –10% to 15% EtOAc to yield the desired product as a white solid.

Step E: 18,19,20,21,22,23-Hexahydro-1 8-oxo-5H-12,14-etheno-6,10-methenobenz[d]imidazo[4,3-i][1,7,10,13]oxatriaza-cyclononadecine-9-carbonitrile hydrochloride Following the procedure described in Example 6, but using N-[2-(tert-butoxycarbonylamino)ethyl]-7-(triisopropylsilyloxy)naphthalene-1-carboxamide (as described in Example 30, Step D) in place of (R)-2-(tert-butoxycarbonylamino)-N-[7-(tert-butyldiphenylsilyloxy) naphthalen-1-yl]propionamide in Step E, and converting the final product to the hydrochloride salt, the above compound was prepared.

Elemental analysis calculated for C$_{25}$H$_{21}$N$_5$O$_2$•2 HCl•0.35 EtOAc•1.6 H$_2$O: C: 57.02; H: 5.26; N: 12.60 Found: C: 56.97; H: 5.14; N: 12.60

FAB MS: 424 (MH$^+$).

84

Example 31

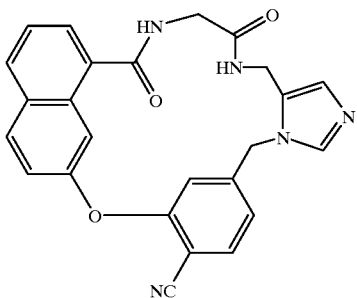

18,19,20,21,22,23-Hexahydro-18,21-dioxo-5H-12,14-etheno-6,10-methenobenz[d]imidazo[4,3-i][1,7,10,13]oxatriazacyclononadecine-9-carbonitrile hydrochloride Step A: 5-(Azidomethyl)-1-(4-cyano-3-fluorobenzyl) imidazole To a stirred solution of 1-(4-cyano-3-fluorobenzyl)-5-(hydroxymethyl)imidazole, as described above in Example 4, Step F, (103 mg, 0.45 mmol) in dry THF (1 mL), at 0° C., under argon, were added DPPA (147 mg, 0.53 mmol) then DBU (75 mg, 0.49 mmol). The mixture was allowed to warm to ambient temperature and then stirred for 3 hrs. The mixture was then partitioned between H$_2$O (10 mL) and CH$_2$Cl$_2$ (20 mL). The aqueous layer was extracted further with CH$_2$Cl$_2$ (2×15 mL). The combined organic extracts were dried over Na$_2$SO$_4$, filtered, and concentrated in vacuo. The crude product was purified by flash column chromatography on silica, eluting with a gradient of CHCl$_3$-1% MeOH –0.1% NH$_4$OH to CHCl$_3$-5% MeOH –0.5% NH$_4$OH, to yield the titled product.

Step B: 5-(Aminomethyl)-1-(4-cyano-3-fluorobenzyl) imidazole hydrochloride

To a solution of 5-(azidomethyl)-1-(4-cyano-3-fluorobenzyl)imidazole, as described above in Step A, (102 mg, 0.40 mmol) in EtOAc (4 mL) was added 10% Pd-C on carbon (10 mg) and the reaction mixture was stirred under an atmosphere of hydrogen (ca. 1 atm) at ambient temperature for 1 hr. The mixture was filtered through a pad of celite, washing with EtOAc, and the filtrate was concentrated in vacuo to give a crude product. This was purified by flash column chromatography on silica, eluting with a gradient of CH$_2$Cl$_2$-1% MeOH –0.1% NH$_4$OH to CH$_2$Cl$_2$ –10% MeOH –1% NH$_4$OH, to yield the titled product, which was converted into the hydrochloride salt by treatment with HCl in EtOAc.

Step C: N-[7-(Triisopropylsilyloxy)naphthalene-1-carbonyl]glycine methyl ester

To glycine methyl ester hydrochloride (140 mg, 1.12 mmol) in dry DMF (1 mL) under argon were added PYBOP (233 g, 0.45 mmol), 7-(triisopropylsilyloxy)-1-naphthoic acid, as described in Example 30, Step D, (155 mg, 0.45 mmol), and N,N-diisopropylethylamine (0.31 mL, 1.78 mmol). The reaction mixture was stirred for 3 hrs, then partitioned between CH$_2$Cl$_2$ (50 mL) and H$_2$O (20 mL). The organic layer was dried over Na$_2$SO$_4$, filtered, and concentrated in vacuo. The residue was purified by flash column chromatography on silica, eluting with CH$_2$Cl$_2$-5% EtOAc to yield the desired product as a colorless oil.

85

Step D: N-[7-(Triisopropylsilyloxy)naphthalene-1-carbonyl]glycine lithium salt

To a solution of N-[7-(triisopropylsilyloxy)naphthalene-1-carbonyl]glycine methyl ester, as described above in Step C, (175 mg, 0.42 mmol) in 4:1 THF/water (5 mL) at ambient temperature was added lithium hydroxide monohydrate (18 mg, 0.44 mmol). After 30 min, the solution was adjusted to pH 7 with 1.0 N hydrochloric acid and concentrated in vacuo. The residue was concentrated from toluene in vacuo (3×10 mL) to give the titled product.

Step E: 7-(Triisopropylsilyloxy)naphthalene-1-carboxylic acid ({[3-(4-cyano-3-fluoro-benzyl)-3H-imidazol-4-ylmethyl]carbamoyl}methyl)amide

To 5-(aminomethyl)-1-(4-cyano-3-fluorobenzyl) imidazole hydrochloride, as described above in Step B, (54 mg, 0.18 mmol) in dry THF (2 mL) under argon were added PYBOP (219 g, 0.42 mmol), N-[7-(triisopropylsilyloxy)naphthalene-1-carbonyl]glycine lithium salt, as described above in Step D, (171 mg, 0.42 mmol), and N,N-diisopropylethylamine (0.124 mL, 0.71 mmol). The reaction mixture was stirred for 3 hrs, then partitioned between $CH_2Cl_2$ (30 mL) and saturated aqueous $NaHCO_3$ (10 mL). The aqueous layer was extracted further with $CH_2Cl_2$ (2×15 mL). The combined organic extracts were dried over $Na_2SO_4$, filtered, and concentrated in vacuo. The residue was purified by flash column chromatography on silica, eluting with a gradient of $CH_2Cl_2$-1% MeOH –0.1% $NH_4OH$ to $CH_2Cl_2$-5% MeOH –0.5% $NH_4OH$, to yield the desired product as a pale foam.

Step F: 18,19,20,21,22,23-Hexahydro-18,21-dioxo-5H-12,14-etheno-6,10-methenobenz[d]imidazo[4,3-l][1,7,10,13]oxatriazacyclononadecine-9-carbonitrile hydrochloride

A mixture of 7-(triisopropylsilyloxy)naphthalene-1-carboxylic acid ({[3-(4-cyano-3-fluoro-benzyl)-3H-imidazol-4-ylmethyl]carbamoyl}methyl)amide, as described above in Step E, (63 mg, 0.14 mmol) and $Cs_2CO_3$ (112 mg, 0.34 mmol) in dry, degassed DMF (15 mL) was stirred at 65° C. under argon for 18 hrs, then the solvent was removed under reduced pressure. The residue was partitioned between saturated aqueous $NaHCO_3$ (10 mL) and $CH_2Cl_2$ (20 mL). The aqueous layer was extracted further with $CH_2Cl_2$ (2×20 mL), then with EtOAc (3×20 mL). The combined organic extracts were dried over $Na_2SO_4$, filtered, and concentrated in vacuo. The crude product was purified by flash column chromatography on silica, eluting with a gradient of $CH_2Cl_2$-1% MeOH –0.1% $NH_4OH$ to $CH_2Cl_2$-7% MeOH –0.7% $NH_4OH$, to yield the desired product which was converted to the hydrochloride salt by treatment with HCl in EtOAc.

Elemental analysis calculated for $C_{25}H_{19}N_5O_3HCl \cdot 0.85$ EtOAc: C: 62.15; H: 4.92; N: 12.76 Found: C: 62.21; H: 4.81; N: 12.71

FAB MS: 438 (MH$^+$).

86

Example 32

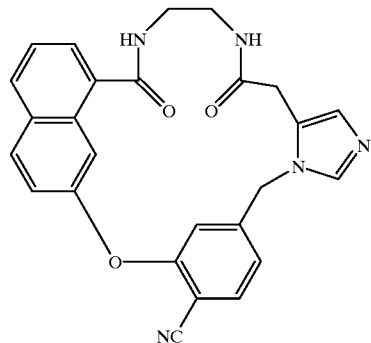

19,20,21,22,23,24-Hexahydro-18,23-dioxo-5H-12,14-etheno-6,10-18H-methenobenz[d]imidazo[4,3-m][1,7,10,14]oxatriazacycloeicosine-9-carbonitrile hydrochloride

Following the procedure described in Example 12, but using N-(2-aminoethyl)-7-hydroxynaphthalene-1-carboxamide (as described in Example 30) in place of (R)-2-amino-N-(7-hydroxynaphthalen-1-yl)propionamide hydrochloride in Step E, and converting the final product to the hydrochloride salt, the above compound was prepared.

Elemental analysis calculated for $C_{26}H_{21}N_5O_3 \cdot HCl \cdot 0.9$ EtOAc·0.3 $H_2O$: C: 62.08; H: 5.25; N: 12.23 Found: C: 62.08; H: 5.14; N: 12.17

FAB MS: 452 (MH$^+$).

Example 33

In vitro inhibition of ras farnesyl transferase

Transferase Assays. Isoprenyl-protein transferase activity assays are carried out at 30° C. unless noted otherwise. A typical reaction contains (in a final volume of 50 μL): [$^3$H]farnesyl diphosphate, Ras protein, 50 mM HEPES, pH 7.5, 5 mM $MgCl_2$, 5 mM dithiothreitol, 10 μM $ZnCl_2$, 0.1% polyethyleneglycol (PEG) (15,000–20,000 mw) and isoprenyl-protein transferase. The FPTase employed in the assay is prepared by recombinant expression as described in Omer, C. A., Kral, A. M., Diehl, R. E., Prendergast, G. C., Powers, S., Allen, C. M., Gibbs, J. B. and Kohl, N. E. (1993) Biochemistry 32:5167–5176. After thermally pre-equilibrating the assay mixture in the absence of enzyme, reactions are initiated by the addition of isoprenyl-protein transferase and stopped at timed intervals (typically 15 min) by the addition of 1M HCl in ethanol (1 mL). The quenched reactions are allowed to stand for 15 m (to complete the precipitation process). After adding 2 mL of 100% ethanol, the reactions are vacuum-filtered through Whatman GFIC filters. Filters are washed four times with 2 mL aliquots of 100% ethanol, mixed with scintillation fluid (10 mL) and then counted in a Beckman LS3801 scintillation counter.

For inhibition studies, assays are run as described above, except inhibitors are prepared as concentrated solutions in 100% dimethyl sulfoxide and then diluted 20-fold into the enzyme assay mixture. Substrate concentrations for inhibitor $IC_{50}$ determinations are as follows: FTase, 650 nM Ras-CVLS (SEQ.ID.NO.: 1), 100 nM farnesyl diphosphate.

The compounds of the instant invention are tested for inhibitory activity against human FPTase by the assay described above.

The compounds of the instant invention described in the above Examples 4–32 were tested for inhibitory activity against human FPTase by the assay described above and were found to have an $IC_{50}$ of $\leq 5$ $\mu M$.

Example 34
Modified In vitro GGTase inhibition assay

The modified geranylgeranyl-protein transferase inhibition assay is carried out at room temperature. A typical reaction contains (in a final volume of 50 $\mu L$): [$^3$H] geranylgeranyl diphosphate, biotinylated Ras peptide, 50 mM HEPES, pH 7.5, a modulating anion (for example 10 mM glycerophosphate or 5 mM ATP), 5 mM $MgCl_2$, 10 $\mu M$ $ZnCl_2$, 0.1% PEG (15,000–20,000 mw), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 2). Reactions are initiated by the addition of GGTase and stopped at timed intervals (typically 15 min) by the addition of 200 $\mu L$ of a 3 mg/mL suspension of streptavidin SPA beads (Scintillation Proximity Assay beads, Amersham) in 0.2M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. $IC_{50}$ values are determined with Ras peptide near $K_M$ concentrations. Enzyme and substrate concentrations for inhibitor $IC_{50}$ determinations are as follows: 75 $\mu M$ GGTase-I, 1.6 $\mu M$ Ras peptide, 100 nM geranylgeranyl diphosphate.

The compounds of the instant invention are tested for inhibitory activity against human GGTase-type I by the assay described above.

Example 35
Cell-based in vitro ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labeled in 3 ml methionine-free DMEM supplemented with 10% regular DMEM, 2% fetal bovine serum and 400 $\mu Ci$[$^{35}$S]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immuno-precipitated with the ras-specific monoclonal antibody Y13–259 (Furth, M. E. et al., *J. Virol.* 43:294–304, (1982)). Following a 2 hour antibody incubation at 4° C., 200 $\mu l$ of a 25% suspension of protein A-Sepharose coated with rabbit anti rat IgG is added for 45 min. The immuno-precipitates are washed four times with IP buffer (20 nM HEPES, pH 7.5/1 mM EDTA/1% Triton X-100.0.5% deoxycholate/ 0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 36
Cell-based in vitro growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1 \times 10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1 % methanol or the concentration of the instant compound. Photomicrographs are taken 16 days after the cultures are seeded and comparisons are made.

Example 37
Construction of SEAP reporter plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoRl and HpaI. The ends of the linear DNA fragments were filled in with the Klenow fragment of *E. coli* DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into $DH_5$-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Alternative Construction of SEAP reporter plasmid, pDSE101

The SEAP repotrer plasmid, pDSE101 is also constructed by ligating a restriction fragment containing the SEAP coding sequence into the plasmid pCMV-RE-AKI. The SEAP gene is derived from plasmid pGEM7zf(−)/SEAP.

The plasmid pDSE101 was constructed as follows: A restriction fragment containing part of the SEAP gene coding sequence was cut out of the plasmid pGEM7zf(−)/SEAP using the restriction enzymes Apa I and KpnI. The ends of the linear DNA fragments were chewed back with the Klenow fragment of E. coli DNA Polymerase I. The "blunt ended" DNA containing the truncated SEAP gene was isolated by electrophoresing the digest in an agarose gel and cutting out the 1910 base pair fragment. This 1910 base pair fragment was ligated into the plasmid pCMV-RE-AKI which had been cut with Bgl-II and filled in with E. coli Klenow fragment DNA polymerase. Recombinant plasmids were screened for insert orientation and sequenced through the ligated junctions. The plasmid pCMV-RE-AKI is derived from plasmid pCMVIE-AKI-DHFR (Whang, Y., Silberklang, M., Morgan, A., Munshi, S., Lenny, A. B., Ellis, R. W., and Kieff, E. (1987) J. Virol., 61, 1796–1807) by removing an EcoRI fragment containing the DHFR and Neomycin markers. Five copies of the fos promoter serum response element were inserted as described previously (Jones, R. E., Defeo-Jones, D., McAvoy, E. M., Vuocolo, G. A., Wegrzyn, R. J., Haskell, K. M. and Oliff, A. (1991) Oncogene, 6, 745–751) to create plasmid pCMV-RE-AKI.

The plasmid pGEM7zf(−)/SEAP was constructed as follows. The SEAP gene was PCRed, in two segments from a human placenta cDNA library (Clontech) using the following oligos.

Sense strand N-terminal SEAP: 5' GAGAGGGAAT-TCGGGCCCTTCCTGCAT GCTGCTGCTGCTGCT-GCTGCTGGGC 3' (SEQ.ID.NO.:4)
Antisense strand N-terminal SEAP: 5' GAGAGAGCTC-GAGGTTAACCCGGGT GCGCGGCGTCGGTGGT 3' (SEQ.ID.NO.:5)
Sense strand C-terminal SEAP: 5' GAGAGAGTCTA-GAGTTAACCCGTGGTCC CCGCGTTGCTTCCT 3' (SEQ.ID.NO.:6)
Antisense strand C-terminal SEAP: 5' GAAGAGGAAGCT-TGGTACCGCCACTG GGCTGTAGGTGGTGGCT 3' (SEQ.ID.NO.:7)

The N-terminal oligos (SEQ.ID.NO.: 4 and SEQ.ID.NO.: 5) were used to generate a 1560 bp N-terminal PCR product that contained EcoRI and HpaI restriction sites at the ends. The Antisense N-terminal oligo (SEQ.ID.NO.: 5) introduces an internal translation STOP codon within the SEAP gene along with the HpaI site. The C-terminal oligos (SEQ.ID.NO.: 6 and SEQ.ID.NO.: 7) were used to amplify a 412 bp C-terminal PCR product containing HpaI and HindIII restriction sites. The sense strand C-terminal oligo (SEQ.ID.NO.: 6) introduces the internal STOP codon as well as the HpaI site. Next, the N-terminal amplicon was digested with EcoRI and HpaI while the C-terminal amplicon was digested with HpaI and HindIII. The two fragments comprising each end of the SEAP gene were isolated by electrophoresing the digest in an agarose gel and isolating the 1560 and 412 base pair fragments. These two fragments were then co-ligated into the vector pGEM7zf(−) (Promega) which had been restriction digested with EcoRI and HindIII and isolated on an agarose gel. The resulting clone, pGEM7zf(−)/SEAP contains the coding sequence for the SEAP gene from amino acids.

Construction of a constitutively expressing SEAP plasmid pCMV-SEAP-A

An expression plasmid constitutively expressing the SEAP protein was created by placing the sequence encoding a truncated SEAP gene downstream of the cytomegalovirus (CMV) IE-1 promoter. The expression plasmid also includes the CMV intron A region 5' to the SEAP gene as well as the 3' untranslated region of the bovine growth hormone gene 3' to the SEAP gene.

The plasmid pCMVIE-AKI-DHFR (Whang, Y., Silberklang, M., Morgan, A., Munshi, S., Lenny, A. B., Ellis, R. W., and Kieff, E. (1987) J. Virol., 61:1796–1807) containing the CMV immediate early promoter was cut with EcoRI generating two fragments. The vector fragment was isolated by agarose electrophoresis and religated. The resulting plasmid is named pCMV-AKI. Next, the cytomegalovirus intron A nucleotide sequence was inserted downstream of the CMV IE1 promter in pCMV-AKI. The intron A sequence was isolated from a genomic clone bank and subcloned into pBR322 to generate plasmid p16T-286. The intron A sequence was mutated at nucleotide 1856 (nucleotide numbering as in Chapman, B. S., Thayer, R. M., Vincent, K. A. and Haigwood, N. L., Nuc.Acids Res. 19, 3979–3986) to remove a SacI restriction site using site directed mutagenesis. The mutated intron A sequence was PCRed from the plasmid p16T-287 using the following oligos.

Sense strand: 5' GGCAGAGCTCGTTTAGTGAACCGT-CAG 3' (SEQ.ID.NO.: 8)
Antisense strand: 5' GAGAGATCTCAAGGACGGT-GACTGCAG 3' (SEQ.ID.NO.: 9)

These two oligos generate a 991 base pair fragment with a Sacd site incorporated by the sense oligo and a Bgl-II fragment incorporated by the antisense oligo. The PCR fragment is trimmed with SacI and Bgl-II and isolated on an agarose gel. The vector pCMV-AKI is cut with SacI and Bgl-II and the larger vector fragment isolated by agarose gel electrophoresis. The two gel isolated fragments are ligated at their respective SacI and Bgl-II sites to create plasmid pCMV-AKI-InA.

The DNA sequence encoding the truncated SEAP gene is inserted into the pCMV-AKI-InA plasmid at the Bgl-II site of the vector. The SEAP gene is cut out of plasmid pGEM7zf (−)/SEAP (described above) using EcoRI and HindIII. The fragment is filled in with Klenow DNA polymerase and the 1970 base pair fragment isolated from the vector fragment by agarose gel electrophoresis. The pCMV-AKI-InA vector is prepared by digesting with Bgl-II and filling in the ends with Klenow DNA polymerase. The final construct is generated by blunt end ligating the SEAP fragment into the pCMV-AKI-InA vector. Transformants were screened for the proper insert and then mapped for restriction fragment orientation. Properly oriented recombinant constructs were sequenced across the cloning junctions to verify the correct sequence. The resulting plasmid, named pCMV-SEAP-A (deposited in the ATCC under Budapest Treaty on Aug. 27, 1998, and designated ATCC), contains a modified SEAP sequence downstream of the cytomegalovirus immediately early promoter IE-1 and intron A sequence and upstream of the bovine growth hormone poly-A sequence. The plasmid expresses SEAP in a constitutive manner when transfected into mammalian cells.

Alternative construction of a constitutively expressing SEAP plasmid pCMV-SEAP-B An expression plasmid constitutively expressing the SEAP protein can be created by placing the sequence encoding a truncated SEAP gene downstream of the cytomegalovirus (CMV) IE-1 promoter and upstream of the 3' unstranslated region of the bovine growth hormone gene.

The plasmid pCMVIE-AKI-DHFR (Whang, Y., Silberklang, M., Morgan, A., Munshi, S., Lenny, A. B., Ellis, R. W., and Kieff, E. (1987) J. Virol., 61:1796–1807) containing the CMV immediate early promoter and bovine growth hormone poly-A sequence can be cut with EcoRI generating two fragments. The vector fragment can be isolated by agarose electrophoresis and religated. The resulting plasmid is named pCMV-AKI. The DNA sequence encoding the truncated SEAP gene can be inserted into the pCMV-AKI plasmid at a unique Bgl-II in the vector. The SEAP gene is cut out of plasmid pGEMzf(−)/SEAP (described above) using EcoRI and HindIII. The fragments are filled in with Klenow DNA polymerase and the 1970 base pair fragment is isolated from the vector fragment by agarose gel electrophoresis. The pCMV-AKI vector is prepared by digesting with Bgl-II and filling in the ends with Klenow DNA polymerase. The final construct is generated by blunt end ligating the SEAP fragment into the vector and transforming the ligation reaction into $E.\ coli$ $DH_5\alpha$ cells. Transformants can then be screened for the proper insert and mapped for restriction fragment orientation. Properly oriented recombinant constructs would be sequenced across the cloning junctions to verify the correct sequence. The resulting plasmid, named pCMV-SEAP-B contains a modified SEAP sequence downstream of the cytomegalovirus immediate early promoter, IE1, and upstream of a bovine growth hormone poly-A sequence. The plasmid would express SEAP in a constitutive nammer when transfected into mammalian cells.

Cloning of a Myristylated viral-H-ras expression plasmid pSMS600

A DNA fragment containing viral-H-ras can be PCRed from plasmid "HB-11 (deposited in the ATCC under Budapest Treaty on Aug. 27, 1997, and designated ATCC 209,218) using the following oligos.

Sense strand: 5'TCTCCTCGAGGCCACCATGGGGAG-TAGCAAGAGCAAGCCTAA GGACCCCAGC-CAGCGCCGGATGACAGAATACAAGCTTGTGGTG G 3'. (SEQ.ID.NO.: 10)

Antisense: 5'CACATCTAGATCAGGACAGCACAGACT-TGCAGC 3'. (SEQ.ID.NO.: 11)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site. To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3' end. The XhoI-XbaI fragment can be ligated into the mammalian expression plasmid pCI (Promega) cut with XhoI and XbaI. This results in a plasmid, pSMS600, in which the recombinant myr-viral-H-ras gene is constitutively transcribed from the CMV promoter of the pCI vector.

Cloning of a viral-H-ras-CVLL expression plasmid pSMS601

A viral-H-ras clone with a C-terminal sequence encoding the amino acids CVLL can be cloned from the plasmid "HB-11" by PCR using the following oligos.

Sense strand:
5'TCTCCTCGAGGCCACCATGACAGAATACAAGC-TTGTGGTGG-3' (SEQ.ID.NO.: 12)

Antisense strand: 5' CACTCTAGACTGGTGTCAGAGCAGCACACACTT-GCAGC-3' (SEQ.ID.NO.: 13)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid, pSMS601, in which the mutated viral-H-ras-CVLL gene is constitutively transcribed from the CMV promoter of the pCI vector.

Cloning of cellular-H-ras-Leu61 expression plasmid pSMS620

The human cellular-H-ras gene can be PCRed from a human cerebral cortex cDNA library (Clontech) using the following oligonucleotide primers.

Sense strand:
5'-GAGAGAATTCGCCACCATGACGGAATATAAGC-TGGTGG-3' (SEQ.ID.NO.: 14)

Antisense strand:
5'-GAGAGTCGACGCGTCAGGAGAGCACACACTT-GC-3' (SEQ.ID.NO.: 15)

The primers will amplify a c-H-Ras encoding DNA fragment with the primers contributing an optimized 'Kozak' translation start sequence, an EcoRI site at the N-terminus and a Sal I site at the C-terminal end. After trimming the ends of the PCR product with EcoRI and Sal I, the c-H-ras fragment can be ligated ligated into an EcoRI-Sal I cut mutagenesis vector pAlter- I (Promega). Mutation of glutamine-61 to a leucine can be accomplished using the manufacturer's protocols and the following oligonucleotide:

5'-CCGCCGGCCTGGAGGAGTACAG-3' (SEQ.ID.NO.: 16)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid, pSMS620, will constitutively transcribe c-H-ras-Leu61 from the CMV promoter of the pCI vector.

Cloning of a c-N-ras-Val-12 expression plasmid pSMS630

The human c-N-ras gene can be PCRed from a human cerebral cortex cDNA library (Clontech) using the following oligonucleotide primers.

Sense strand:
5'-GAGAGAATTCGCCACCATGACTGAGTACAAA-CTGGTGG-3' (SEQ.ID.NO.: 17)

Antisense strand:
5'-GAGAGTCGACTTGTTACATCACCACACATGGC-3' (SEQ.ID.NO.: 18)

The primers will amplify a c-N-Ras encoding DNA fragment with the primers contributing an optimized 'Kozak' translation start sequence, an EcoRI site at the N-terminus and a Sal I site at the C-terminal end. After trimming the ends of the PCR product with EcoRi and Sal I, the c-N-ras fragment can be ligated into an EcoRI -Sal I cut mutagenesis vector pAlter-1 (Promega). Mutation of glycine-12 to a valine can be accomplished using the manufacturer's protocols and the following oligonucleotide:
5'-GTTGGAGCAGTTGGTGTTGGG-3' (SEQ.ID.NO.: 19)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid, pSMS630, will constitutively transcribe c-N-ras-Val-12 from the CMV promoter of the pCI vector.

Cloning of a c-K4B-ras-Val-12 expression plasmid pSMS640

The human c-K4B-ras gene can be PCRed from a human cerebral cortex cDNA library (Clontech) using the following oligo-nucleotide primers.

Sense strand:
5'-GAGAGGTACCGCCACCATGACTGAATATAAAC-TTGTGG-3' (SEQ.ID.NO.: 20)

Antisense strand:
5'-CTCTGTCGACGTATTTACATAATTACACACTTT-GTC-3' (SEQ.ID.NO.: 21)

The primers will amplify a c-K4B-Ras encoding DNA fragment with the primers contributing an optimized 'Kozak' translation start sequence, a KpnI site at the N-terminus and a Sal I site at the C-terminal end. After trimming the ends of the PCR product with Kpn I and Sal I, the c-K4B-ras fragment can be ligated into a KpnI -Sal I cut mutagenesis vector pAlter-1 (Promega). Mutation of cysteine-12 to a valine can be accomplished using the manufacturer's protocols and the following oligonucleotide:
5,'-GTAGTTGGAGCTGTTGGCGTAGGC-3' (SEQ.ID.NO.: 22)

After selection and sequencing for the correct nucleotide substitution, the mutated c-K4B-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K4B-ras-Val-12 from the CMV promoter of the pCI vector.

Cloning of c-K-ras4A-Val-12 expression plasmid pSMS650

The human c-K4A-ras gene can be PCRed from a human cerebral cortex cDNA library (Clontech) using the following oligo-nucleotide primers.
Sense strand:
5'-GAGAGGTACCGCCACCATGACTGAATATAAAC-TTGTGG-3' (SEQ.ID.NO.: 23)
Antisense strand:
5'-CTCTGTCGACAGATTACATTATAATGCATTTTTT-AATTTTCACA C-3' (SEQ.ID.NO.: 24)

The primers will amplify a c-K4A-Ras encoding DNA fragment with the primers contributing an optimized 'Kozak' translation start sequence, a KpnI site at the N-terminus and a Sal I stite at the C-terminal end. After trimming the ends of the PCR product with Kpn I and Sal I, the c-K-ras4A fragment can be ligated into a KpnI -Sal I cut mutagenesis vector pAlter-1 (Promega). Mutation of cysteine-12 to a valine can be accomplished using the manufacturer's protocols and the following oligonucleotide:
5'-GTAGTTGGAGCTGTTGGCGTAGGC-3' (SEQ.ID.NO.: 25)

After selection and sequencing for the correct nucleotide substitution, the mutated c-K4A-ras-Val-12 can be excised from the pAlter-1 vector, using KpnI and Sal I, and be directly ligated into the vector pCI (Promega) which has been digested with KpnI and Sal I. The new recombinant plasmid, pSMS650, will constitutively transcribe c-K4A-ras-Val-12 from the CMV promoter of the pCI vector.

SEAP assay

Human $C_{33}A$ cells (human epitheial carcenoma—ATTC collection) are seeded in 10 cm tissue culture plates in DMEM+10% fetal calf serum+1X Pen/Strep+1X glutamine+1X NEAA. Cells are grown at 37° C. in a 5% $CO_2$ atmosphere until they reach 50 –80% of confluency.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. (A ras expression plasmid is not included when the cell is transfected with the pCMV-SEAP plasmid.) For 10 cm plates 600 µl of $CaCl_2$-DNA solution is added dropwise while vortexing to 600 µl of 2X HBS buffer to give 1.2 ml of precipitate solution (see recipes below). This is allowed to sit at room temperature for 20 to 30 minutes. While the precipitate is forming, the media on the $C_{33}A$ cells is replaced with DMEM (minus phenol red; Gibco cat. No. 31053–028)+0.5% charcoal stripped calf serum+1X (Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+ 1X (Pen/Strep, Glutamine and NEAA ). Transfected cells are plated in a 96 well microtiter plate (100 µl/well) to which drug, diluted in media, has already been added in a volume of 100 µl. The final volume per well is 200 µl with each drug concentration repeated in triplicate over a range of half-log steps.

Incubation of cells and drugs is for 36 hrs at 37° under $CO_2$. At the end of the incubation period, cells are examined micro-scopically for evidence of cell distress. Next, 100 µl of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 µl media is combined with 200 µl of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

$DNA-CAPO_4$ precipitate for 10 cm. plate of cells

| | |
|---|---|
| Ras expression plasmid (1 µg/µl) | 10 µl |
| DSE-SEAP Plasmid (1 µg/µl) | 2 µl |
| Sheared Calf Thymus DNA (1 µg/µl) | 8 µl |
| 2M $CaCl_2$ | 74 µl |
| $dH_2O$ | 506 µl |

2X HBS Buffer 280 mM NaCl 10 mM KCl 1.5 mM $Na_2HPO_4$ $2H_2O$ 12 mM dextrose 50 mM HEPES Final pH=7.05

Luminesence Buffer (26 ml)

| | |
|---|---|
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |

Assay Buffer

Add 0.05M $Na_2CO_3$ to 0.05M $NaHCO_3$ to obtain pH 9.5. Make 1 mM in $MgCl_2$

Example 38

The processing assays employed are modifications of that described by DeClue et al [Cancer Research 51, 712–717, 1991].

K4B-Ras processing inhibition assay

PSN-1 (human pancreatic carcinoma) or viral-K4B-ras-transformed Rat1 cells are used for analysis of protein processing. Subconfluent cells in 100 mm dishes are fed with 3.5 ml of media (methionine-free RPMI supplemented with 2% fetal bovine serum or cysteine-free/methionine-free DMEM supplemented with 0.035 ml of 200 mM glutamine (Gibco), 2% fetal bovine serum, respectively) containing the desired concentration of test compound, lovastatin or solvent alone. Cells treated with lovastatin (5–10 $\mu$M), a compound that blocks Ras processing in cells by inhibiting a rate-limiting step in the isoprenoid biosynthetic pathway, serve as a positive control. Test compounds are prepared as 1000× concentrated solutions in DMSO to yield a final solvent concentration of 0.1%. Following incubation at 37° C. for two hours 204 $\mu$Ci/ml [$^{35}$S]Pro-Mix (Amersham, cell labeling grade) is added.

After introducing the label amino acid mixture, the cells are incubated at 37° C. for an additional period of time (typically 6 to 24 hours). The media is then removed and the cells are washed once with cold PBS. The cells are scraped into 1 ml of cold PBS, collected by centrifugation (10,000×g for 10 sec at room temperature), and lysed by vortexing in 1 ml of lysis buffer (1% Nonidet P-40, 20 mM HEPES, pH 7.5, 150 mM NaCl, 1 mM EDTA, 0.5% deoxycholate, 0.1% SDS, 1 mM DTT, 10 $\mu$g/ml AEBSF, 10 $\mu$g/ml aprotinin, 2 $\mu$g/ml leupeptin and 2 $\mu$g/ml antipain). The lysate is then centrifuged at 15,000×g for 10 min at 4° C. and the supernatant saved.

For immunoprecipitation of Ki4B-Ras, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 8 $\mu$g of the pan Ras monoclonal antibody, Y13–259, added. The protein/antibody mixture is incubated on ice at 4° C. for 24 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in 100 $\mu$l elution buffer (10 mM Tris pH 7.4, 1% SDS). The Ras is eluted from the beads by heating at 95° C. for 5 minutes, after which the beads are pelleted by brief centrifugation (15,000×g for 30 sec. at room temperature).

The supernatant is added to 1 ml of Dilution Buffer 0.1% Triton X-100, 5 mM EDTA, 50 mM NaCl, 10 mM Tris pH 7.4) with 2 $\mu$g Kirsten-ras specific monoclonal antibody, c-K-ras Ab-1 (Calbiochem). The second protein/antibody mixture is incubated on ice at 4° C. for 1–2 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in Laemmli sample buffer. The Ras is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Ras visualized by fluorography.

hDJ processing inhibition assay

PSN-1 cells are seeded in 24-well assay plates. For each compound to be tested, the cells are treated with a minimum of seven concentrations in half-log steps. The final solvent (DMSO) concentration is 0.1%. A vehicle-only control is included on each assay plate. The cells are treated for 24 hours at 37° C./5% $CO_2$.

The growth media is then aspirated and the samples are washed with PBS. The cells are lysed with SDS-PAGE sample buffer containing 5% 2-mercaptoethanol and heated to 95° C. for 5 minutes. After cooling on ice for 10 minutes, a mixture of nucleases is added to reduce viscosity of the samples.

The plates are incubated on ice for another 10 minutes. The samples are loaded onto pre-cast 8% acrylamide gels and electrophoresed at 15 mA/gel for 3–4 hours. The samples are then transferred from the gels to PVDF membranes by Western blotting.

The membranes are blocked for at least 1 hour in buffer containing 2% nonfat dry milk. The membranes are then treated with a monoclonal antibody to hDJ-2 (Neomarkers Cat. # MS-225), washed, and treated with an alkaline phosphatase-conjugated secondary antibody. The membranes are then treated with a fluorescent detection reagent and scanned on a phosphorimager.

For each sample, the percent of total signal corresponding to the unprenylated species of hDJ (the slower-migrating species) is calculated by densitometry. Dose-response curves and $EC_{50}$ values are generated using 4-parameter curve fits in SigmaPlot software.

Example 39

Rap I processing inhibition assay

Protocol A:

Cells are labeled, incubated and lysed as described in Example 38.

For immunoprecipitation of Rap1, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 2 $\mu$g of the Rap I antibody, Rap1/Krev1 (121) (Santa Cruz Biotech), is added. The protein/antibody mixture is incubated on ice at 4° C. for 1 hour. The immune complex is collected on pansorbin (Calbiochem) by tumbling at 4° C. for 45 minutes. The pellet is washed 3 times with 1 ml of lysis buffer lacking DTT and protease inhibitors and resuspended in 100 $\mu$l elution buffer (10 mM Tris pH 7.4, 1% SDS). The Rap1 is eluted from the beads by heating at 95° C. for 5 minutes, after which the beads are pelleted by brief centrifugation (15,000×g for 30 sec. at room temperature).

The supernatant is added to 1 ml of Dilution Buffer (0.1% Triton X-100, 5 mM EDTA, 50 mM NaCl, 10 mM Tris pH 7.4) with 2 $\mu$g Rap1 antibody, Rap1/Krev1 (121) (Santa Cruz Biotech). The second protein/antibody mixture is incubated on ice at 4° C. for 1–2 hours. The immune complex is collected on pansorbin (Calbiochem) by tumbling at 4° C. for 45 minutes. The pellet is washed 3 times with 1 ml of lysis buffer lacking DTT and protease inhibitors and resuspended in Laemmli sample buffer. The Rap1 is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Rap1 visualized by fluorography.

Protocol B:

PSN-1 cells are passaged every 3–4 days in 10 cm plates, splitting near-confluent plates 1:20 and 1:40. The day before the assay is set up, 5×10$^6$ cells are plated on 15 cm plates to ensure the same stage of confluency in each assay. The media for these cells is RPM1 1640 (Gibco), with 15% fetal bovine serum and 1× Pen/Strep antibiotic mix.

The day of the assay, cells are collected from the 15 cm plates by trypsinization and diluted to 400,000 cells/ml in media. 0.5 ml of these diluted cells are added to each well of 24-well plates, for a final cell number of 200,000 per well. The cells are then grown at 37° C. overnight.

The compounds to be assayed are diluted in DMSO in ½-log dilutions. The range of final concentrations to be assayed is generally 0.1 –100 μM. Four concentrations per compound is typical. The compounds are diluted so that each concentration is 1000× of the final concentration (i.e., for a 10 μM data point, a 10 mM stock of the compound is needed).

2 μL of each 1000× compound stock is diluted into 1 ml media to produce a 2X stock of compound. A vehicle control solution (2 μL DMSO to 1 ml media), is utilized. 0.5 ml of the 2X stocks of compound are added to the cells.

After 24 hours, the media is aspirated from the assay plates. Each well is rinsed with 1 ml PBS, and the PBS is aspirated. 180 μL SDS-PAGE sample buffer (Novex) containing 5% 2-mercapto-ethanol is added to each well. The plates are heated to 100° C. for 5 minutes using a heat block containing an adapter for assay plates. The plates are placed on ice. After 10 minutes, 20 μL of an RNAse/DNase mix is added per well. This mix is 1 mg/ml DNaseI (Worthington Enzymes), 0.25 mg/ml Rnase A (Worthington Enzymes), 0.5M Tris-HCl pH 8.0 and 50 mM $MgCl_2$. The plate is left on ice for 10 minutes. Samples are then either loaded on the gel, or stored at –70° C. until use.

Each assay plate (usually 3 compounds, each in 4-point titrations, plus controls) requires one 15-well 14% Novex gel. 25 μl of each sample is loaded onto the gel. The gel is run at 15 mA for about 3.5 hours. It is important to run the gel far enough so that there will be adequate separation between 21 kd (Rap1) and 29 kd (Rab6).

The gels are then transferred to Novex pre-cut PVDF membranes for 1.5 hours at 30V (constant voltage). Immediately after transferring, the membranes are blocked overnight in 20 ml Western blocking buffer (2% nonfat dry milk in Western wash buffer (PBS+0.1% Tween-20). If blocked over the weekend, 0.02% sodium azide is added. The membranes are blocked at 4° C. with slow rocking.

The blocking solution is discarded and 20ml fresh blocking solution containing the anti Rap1a antibody (Santa Cruz Biochemical SC1482) at 1:1000 (diluted in Western blocking buffer) and the anti Rab6 antibody (Santa Cruz Biochemical SC310) at 1:5000 (diluted in Western blocking buffer) are added. The membranes are incubated at room temperature for 1 hour with mild rocking. The blocking solution is then discarded and the membrane is washed 3 times with Western wash buffer for 15 minutes per wash. 20 ml blocking solution containing 1:1000 (diluted in Western blocking buffer) each of two alkaline phosphatase conjugated antibodies (Alkaline phosphatase conjugated Anti-goat IgG and Alkaline phosphatase conjugated anti-rabbit IgG [Santa Cruz Biochemical]) is then added. The membrane is incubated for one hour and washed 3× as above.

About 2 ml per gel of the Amersham ECF detection reagent is placed on an overhead transparency (ECF) and the PVDF membranes are placed face-down onto the detection reagent. This is incubated for one minute, then the membrane is placed onto a fresh transparency sheet.

The developed transparency sheet is scanned on a phosphorimager and the Rap1a Minimum Inhibitory Concentration is determined from the lowest concentration of compound that produces a detectable Rap1a Western signal. The Rap1a antibody used recognizes only unprenylated/unprocessed Rap1a, so that the precence of a detectable Rap1a Western signal is indicative of inhibition of Rap1a prenylation.

Protocol C:

This protocol allows the determination of an $EC_{50}$ for inhibition of processing of Rap1a. The assay is run as described in Protocol B with the following modifications. 20 μl of sample is run on pre-cast 10–20% gradient acrylamide mini gels (Novex Inc.) at 15 mA/gel for 2.5–3 hours. Prenylated and unprenylated forms of Rap1a are detected by blotting with a polyclonal antibody (Rap1/Krev-1 Ab#121;Santa Cruz Research Products #sc-65), followed by an alkaline phosphatase-conjugated anti-rabbit IgG antibody. The percentage of unprenylated Rap1a relative to the total amount of Rap1a is determined by peak integration using Imagequant® software (Molecular Dynamics). Unprenylated Rap1a is distinguished from prenylated protein by virtue of the greater apparent molecular weight of the prenylated protein. Dose-response curves and $EC_{50}$ values are generated using 4-parameter curve fits in SigmaPlot software.

Example 40

In vivo tumor growth inhibition assay (nude mouse)

In vivo efficacy as an inhibitor of the growth of cancer cells may be confirmed by several protocols well known in the art. Examples of such in vivo efficacy studies are described by N. E. Kohl et al. (Nature Medicine, 1:792–797 (1995)) and N. E. Kohl et al. (Proc. Nat. Acad. Sci. U.S.A., 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5 –1.0 cm in diameter, typically 11–15 days after the cells were injected. The average weight of the tumors in each treatment group for each cell line is calculated.

What is claimed is:

1. A compound of the formula A:

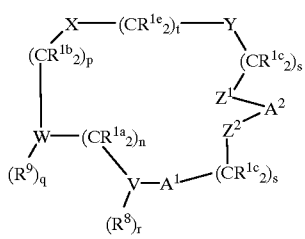

wherein:

$R^{1a}$, $R^{1b}$, $R^{1c}$, $R^{1d}$ and $R^{1e}$ are independently selected from:

a) hydrogen, b) unsubstituted or substituted aryl, unsubstituted or substituted heterocycle, cycloalkyl, alkenyl, alkynyl, $R^{10}O—$, $R^{11}S(O)_m—$, $R^{10}C(O)NR^{10}—$, $(R^{10})_2N—C(O)—$, CN, NO$_2$, $(R^{10})_2N—C(NR^{10})—$, $R^{10}C(O)—$, $R^{10}OC(O)—$, N$_3$, $—N(R^{10})_2$, or $R^{11}OC(O)NR^{10}—$, c) unsubstituted or substituted $C_1$–$C_6$ alkyl wherein the substitutent on the substituted $C_1$–$C_6$ alkyl is selected from unsubstituted or substituted aryl, heterocyclic, cycloalkyl, alkenyl, alkynyl, perfluoroalkyl, halogen, $R^{10}O-$, $R^4S(O)_m-$, $R^4S(O)_2NR^{10}-$, $R^{10}C(O)NR^{10}-$, $(R^{10})_2N-C(O)-$, CN, $(R^{10})_2N-C(NR^{10})-$, $R^{10}C(O)-$, $R^{10}OC(O)-$, $N_3$, $-N(R^{10})_2$, and $R^{11}OC(O)-NR^{10}-$;

or two $R^{1a}$s, two $R^{1b}$s, two $R^{1c}$s, two $R^{1d}$s or two $R^{1e}$s, on the same carbon atom may be combined to form $-(CH_2)_v-$;

$R^4$ is selected from $C_{1-4}$ alkyl, $C_{3-6}$ cycloalkyl, heterocycle, aryl, unsubstituted or substituted with:
 a) $C_{1-4}$ alkoxy,
 b) aryl or heterocycle,
 c) halogen,
 d) HO, e) 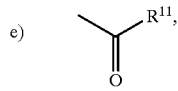

f) $-SO_2R^{11}$,
 g) $N(R^{10})_2$, or
 h) $C_{1-4}$ perfluoroalkyl;

$R^6$ and $R^7$ are independently selected from:
 1) hydrogen,
 2) $R^{10}C(O)-$, or $R^{10}OC(O)-$, and
 3) $C_1-C_6$ alkyl, $C_2-C_6$ alkenyl, $C_2-C_6$ alkynyl, $C_{3-6}$ cycloalkyl, heterocycle, aryl, aroyl, heteroaroyl, arylsulfonyl, heteroarylsulfonyl, $C_6-C_{10}$ multicyclic ring, unsubstituted or substituted with one or more substituents selected from:
  a) $R^{10}O-$,
  b) aryl or heterocycle,
  c) halogen,
  d) $R^{10}C(O)NR^{10}-$, e) 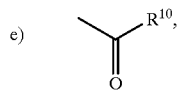

f) $-SO_2R^{11}$,
  g) $N(R^{10})_2$,
  h) $C_{3-6}$ cycloalkyl,
  i) $C_6-C_{10}$ multicyclic ring,
  j) $C_1-C_6$ perfluoroalkyl,
  k) $(R^{10})_2N-C(NR^{10})-$,
  l) $R^{10}OC(O)-$,
  m) $R^{11}OC(O)NR^{10}-$,
  n) CN, and
  o) $NO_2$; or $R^6$ and $R^7$ may be joined in a ring;

$R^8$ is independently selected from:
 a) hydrogen,
 b) unsubstituted or substituted aryl, unsubstituted or substituted heterocycle, $C_3-C_{10}$ cycloalkyl, $C_2-C_6$ alkenyl, $C_2-C_6$ alkynyl, perfluoroalkyl, F, Cl, Br, $R^{12}O-$, $R^{11}S(O)_m-$, $R^{10}C(O)NR^{10}-$, $(R^{10})_2NC(O)-$, $R^{10}_2N-C(NR^{10})-$, CN, $NO_2$, $R^{10}C(O)-$, $R^{10}OC(O)-$, $N_3$, $-N(R^{10})_2$, or $R^{11}OC(O)NR^{10}-$, and
 c) $C_1-C_6$ alkyl unsubstituted or substituted by unsubstituted or substituted aryl, unsubstituted or substituted heterocycle, $C_3-C_{10}$ cycloalkyl, $C_2-C_6$ alkenyl, $C_2-C_6$ alkynyl, perfluoroalkyl, F, Cl, Br, $R^{10}O-$, $R^{11}S(O)_m-$, $R^{10}C(O)NH-$, $(R^{10})_2NC(O)-$, $R^{10}_2N-C(NR^{10})-$, CN, $R^{10}C(O)-$, $R^{10}OC(O)-$, $N_3$, $-N(R^{10})_2$, or $R^{10}OC(O)NH-$;

$R^9$ is selected from:
 a) hydrogen,
 b) $C_2-C_6$ alkenyl, $C_2-C_6$ alkynyl, perfluoroalkyl, F, Cl, Br, $R^{10}O-$, $R^{11}S(O)_m-$, $R^{10}C(O)NR^{10}-$, $(R^{10})_2NC(O)-$, $R^{10}_2N-C(NR^{10})-$, CN, $NO_2$, $R^{10}C(O)-$, $R^{10}OC(O)-$, $N_3$, $-N(R^{10})_2$, or $R^{11}OC(O)NR^{10}-$, and
 c) $C_1-C_6$ alkyl unsubstituted or substituted by perfluoroalkyl, F, Cl, Br, $R^{10}O-$, $R^{11}S(O)_m-$, $R^{10}C(O)NR^{10}-$, $(R^{10})_2NC(O)-$, $R^{10}_2N-C(NR^{10})-$, CN, $R^{10}C(O)-$, $R^{10}OC(O)-$, $N_3$, $-N(R^{10})_2$, or $R^{11}C(O)NR^{10}-$;

$R^{10}$ is independently selected from hydrogen, $C_1-C_6$ alkyl, unsubstituted or substituted benzyl, unsubstituted or substituted aryl and unsubstituted or substituted heterocycle;

$R^{11}$ is independently selected from $C_1-C_6$ alkyl unsubstituted or substituted aryl and unsubstituted or substituted heterocycle;

$R^{12}$ is independently selected from hydrogen, $C_1-C_6$ alkyl, $C_1-C_3$ perfluoroalkyl, unsubstituted or substituted benzyl, unsubstituted or substituted aryl, unsubstituted or substituted heterocycle, and $C_1-C_6$ alkyl substituted with unsubstituted or substituted aryl or unsubstituted or substituted heterocycle;

$A^1$ is selected from a bond and O;

$A^2$ is selected from a bond and O;

W is imidazolyl;

V is phenyl;

X and Y are independently selected from $-C(O)-$, $-C(O)NR^{10}-$, $-NR^{10}C(O)-$, $-NR^{10}C(O)-O-$, $-O-C(O)NR^{10}-$, $-NR^{10}C(O)NR^{10}-$, $-C(O)NR^{10}C(O)-$, O, $-N(R^{10})-$, $-S(O)_2N(R^{10})-$, $-N(R^{10})S(O)_2-$ and $S(O)_m$;

$Z^1$ is selected from unsubstituted or substituted phenyl and unsubstituted or substituted naphthyl, wherein the substituted phenyl or substituted naphthyl is substituted with one or more of:
 1) $C_{1-8}$ alkyl, $C_{2-8}$ alkenyl or $C_{2-8}$ alkynyl, unsubstituted or substituted with:
  a) $C_{1-4}$ alkoxy,
  b) $NR^6R^7$,
  c) $C_{3-6}$ cycloalkyl,
  d) aryl or heterocycle,
  e) HO,
  f) $-S(O)_mR^4$,
  g) $-C(O)NR^6R^7$,
  h) $-Si(C_{1-4} alkyl)_3$, or
  i) $C_{1-4}$ perfluoroalkyl;
 2) substituted or unsubstituted aryl or substituted or unsubstituted heterocycle,
 3) halogen,
 4) $OR^6$,
 5) $NR^6R^7$,
 6) CN,
 7) $NO_2$,
 8) $CF_3$,
 9) $-S(O)_mR^4$,
 10) $-OS(O)_2R^4$,
 11) $-C(O)NR^6R^7$,
 12) $-C(O)OR^6$, or
 13) $C_3-C_6$ cycloalkyl;

$Z^2$ is selected from a bond and unsubstituted or substituted phenyl wherein the substituted phenyl is substituted with one or more of:

1) $C_{1-8}$ alkyl, $C_{2-8}$ alkenyl or $C_{2-8}$ alkynyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) —$S(O)_mR^4$,
   g) —$C(O)NR^6R^7$,
   h) —$Si(C_{1-4}\ allyl)_3$, or
   i) $C_{1-4}$ perfluoroalkyl;
2) substituted or unsubstituted aryl or substituted or unsubstituted heterocycle,
3) halogen,
4) $OR^6$,
5) $NR^6R^7$,
6) CN,
7) $NO_2$,
8) $CF_3$,
9) —$S(O)_mR^4$,
10) —$OS(O)_2R^4$,
11) —$C(O)NR^6R^7$,
12) —$C(O)OR^6$, or
13) $C_3$–$C_6$ cycloalkyl;

m is 0, 1 or 2;
n is 0, 1, 2, 3 or 4;
p is 0, 1, 2, 3 or 4;
q is 1 or 2;
r is 0 to 5;
s is independently 0, 1, 2 or 3;
t is 1, 2, 3 or 4; and
v is 2 to 6;
$C_6$–$C_{10}$ multicyclic ring is selected from:

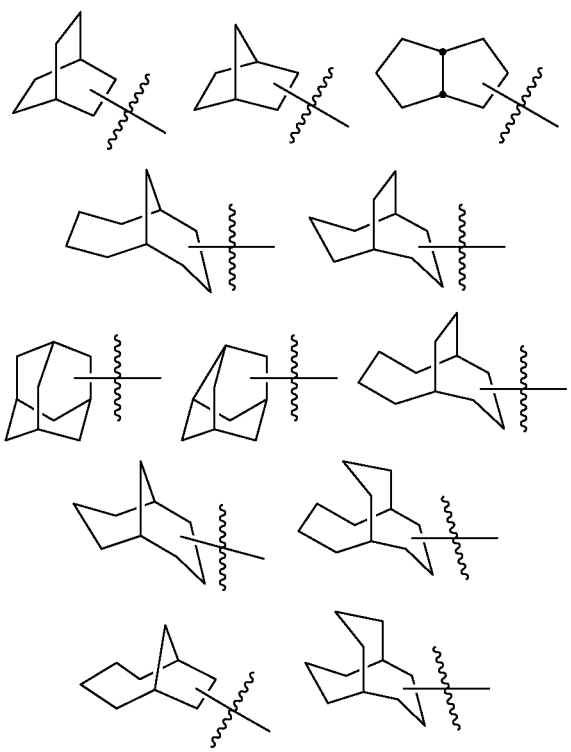
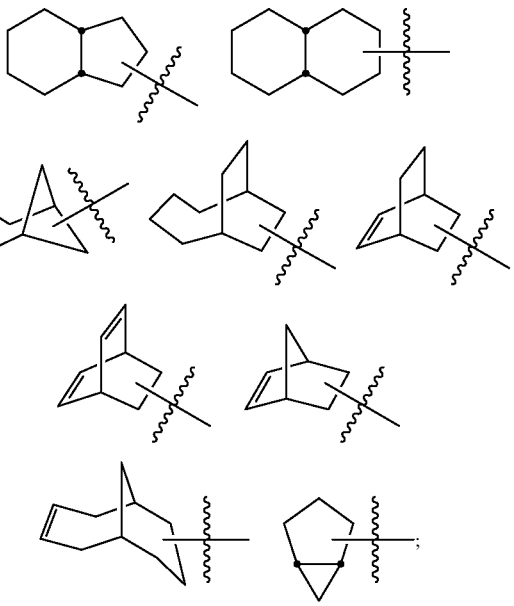

or a pharmaceutically acceptable salt or stereoisomer thereof.

2. The compound according to claim 1 which is:

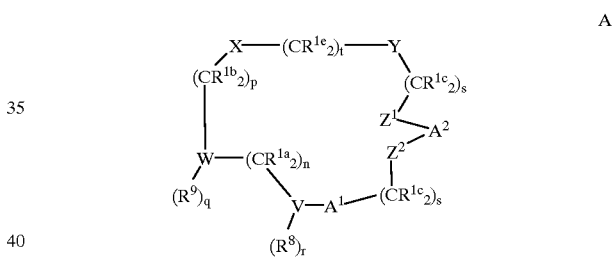

A wherein:

$R^{1a}$, $R^{1b}$, $R^{1c}$, $R^{1d}$ and $R^{1e}$ are independently selected from:
  a) hydrogen,
  b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
  c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^4$ is selected from $C_{1-4}$ alkyl, $C_{3-6}$ cycloalkyl, heterocycle, aryl, unsubstituted or substituted with:
  a) $C_{1-4}$ alkoxy,
  b) aryl or heterocycle,
  c) halogen, d) HO, e) 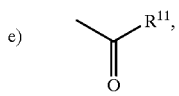

f) —SO$_2$R$^{11}$, or
g) N(R$^{10}$)$_2$;

R$^6$ and R$^7$ are independently selected from H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
  a) C$_{1-4}$ alkoxy,
  b) aryl or heterocycle,
  c) halogen,
  d) HO, e) 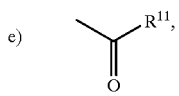

f) —SO$_2$R$^{11}$, or
  g) N(R$^{10}$)$_2$; or

R$^6$ and R$^7$ may be joined in a ring;

R$^8$ is independently selected from:
  a) hydrogen,
  b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, N$_3$, —N(R$^{10}$)$_2$, or R$^{11}$OC(O)NR$^{10}$—, and
  c) C$_1$–C$_6$ alkyl unsubstituted or substituted by unsubstituted or substituted aryl, unsubstituted or substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, R$^{10}$OC(O)—, N$_3$, —N(R$^{10}$)$_2$, or R$^{10}$OC(O)NH—;

R$^9$ is selected from:
  a) hydrogen,
  b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, N$_3$, —N(R$^{10}$)$_2$, or R$^{11}$OC(O)NR$^{10}$—, and
  c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, R$^{10}$OC(O)—, N$_3$, —N(R$^{10}$)$_2$, or R$^{11}$OC(O)NR$^{10}$—;

R$^{10}$ is independently selected from hydrogen, C$_1$–C$_6$ alkyl, benzyl, unsubstituted or substituted aryl and unsubstituted or substituted heterocycle;

R$^{11}$ is independently selected from C$_1$–C$_6$ alkyl unsubstituted or substituted aryl and unsubstituted or substituted heterocycle;

A$^1$ is selected from a bond and O;
A$^2$ is selected from a bond and O;
W is imidazolyl;
V is phenyl;
X and Y are independently selected from —C(O)—, —C(O)NR$^{10}$—, —NR$^{10}$C(O)—, —NR$^{10}$C(O)—O—, —O—C(O)NR$^{10}$—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$— and S(O)$_m$;

Z$^1$ is selected from unsubstituted (or substituted phenyl and unsubstituted or substituted naphthyl, wherein the substituted phenyl or substituted naphthyl is substituted with one or more of:
  1) C$_{1-4}$ alkyl, unsubstituted or substituted with:
    a) C$_{1-4}$alkoxy,
    b) NR$^6$R$^7$,
    c) C$_{3-6}$ cycloalkyl,
    d) aryl or heterocycle,
    e) HO,
    f) —S(O)$_m$R$^4$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$,
  9) —S(O)$_m$R$^4$,
  10) —C(O)NR$^6$R$^7$, or
  11) C$_3$–C$_6$ cycloalkyl;

Z$^2$ is selected from a bond and unsubstituted or substituted phenyl, wherein the substituted phenyl is substituted with one or more of:
  1) C$_{1-4}$ alkyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^4$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$,
  9) —S(O)$_m$R$^4$,
  10) —C(O)NR$^6$R$^7$, or
  11) C$_3$–C$_6$ cycloalkyl;

m is 0, 1 or 2;
n is 0, 1, 2, 3 or 4;
p is 0, 1, 2, 3 or 4;
q is 1 or 2;
r is 0 to 5;
s is independently 0, 1, 2 or 3; and
t is 1, 2, 3 or 4;

or a pharmaceutically acceptable salt or stereoisomer thereof.

3. The compound according to claim 1 of the formula B:

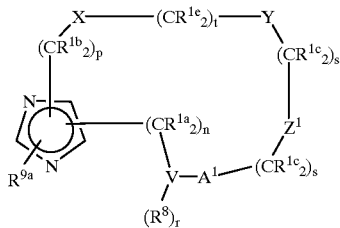

wherein:
R$^{1a}$, R$^{1b}$ and R$^{1c}$ are independently selected from:
  a) hydrogen,
  b) aryl, heterocycle, cycloalkyl, R$^{10}$O—, —N(R$^{10}$)$_2$ or C$_2$–C$_6$ alkenyl, and
  c) C$_1$–C$_6$ alkyl unsubstituted or substituted by aryl heterocycle, cycloalkyl, alkenyl, R$^{10}$O—, or —N(R$^{10}$)$_2$;
R$^{1e}$ is independently selected from:
  a) hydrogen,
  b) unsubstituted or substituted aryl, unsubstituted or substituted heterocycle, cycloalkyl, alkenyl, alkynyl, R$^{10}$O—, R$^{11}$S(O)$_m$—, R$^{10}$C(O)NR$^{10}$—, (R$^{10}$)$_2$N—C(O)—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—,
  c) unsubstituted or substituted C$_1$–C$_6$ alkyl wherein the substitutent on the substituted C$_1$–C$_6$ alkyl is selected from unsubstituted or substituted aryl, heterocyclic, cycloallyl, alkenyl, alkynyl, perfluoroalkyl, halogen, R$^{10}$O—, R$^4$S(O)$_m$—, R$^4$S(O)$_2$NR$^{10}$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—;
or two R$^{1e}$s, on the same carbon atom may be combined to form —(CH$_2$)$_v$—;
R$^4$ is selected from C$_{1-4}$ alkyl and C$_{3-6}$ cycloalkyl, unsubstituted or substituted with:
  a) C$_{1-4}$ alkoxy,
  b) halogen, or
  c) aryl or heterocycle;
R$^6$ and R$^7$ are independently selected from H; C$_{1-6}$ alkyl, C$_{3-6}$ cycloalkyl, C$_6$–C$_{10}$ multicyclic ring, heterocycle, aryl, aroyl, heteroaroyl, arylsulfonyl, heteroarylsulfonyl, unsubstituted or substituted with one or two:
  a) C$_{1-4}$ alkoxy,
  b) aryl or heterocycle,
  c) halogen,
  d) HO, e) 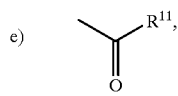

f) —SO$_2$R$^{11}$,
  g) N(R$^{10}$)$_2$,
  h) C$_{3-6}$ cycloalkyl,
  i) C$_6$–C$_{10}$ multicyclic ring; or
R$^8$ is independently selected from:
  a) hydrogen,
  b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^{12}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
  c) C$_1$–C$_6$ alkyl substituted by: unsubstituted or substituted aryl, C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$C(O)NR$^{10}$—;
R$^{9a}$ is hydrogen or methyl;
R$^{10}$ is independently selected from hydrogen, C$_1$–C$_6$ alkyl, benzyl and unsubstituted or substituted aryl;
R$^{11}$ is independently selected from C$_1$–C$_6$ alkyl and unsubstituted or substituted aryl;
R$^{12}$ is independently selected from hydrogen, C$_1$–C$_6$ alkyl, unsubstituted or substituted benzyl, unsubstituted or substituted amyl, unsubstituted or substituted heterocycle, and C$_1$–C$_6$ alkyl substituted with unsubstituted or substituted aryl or unsubstituted or substituted heterocycle;
A$^1$ is selected from a bond and O;
V is phenyl;
X and Y are independently selected from —C(O)—, —C(O)NR$^{10}$—, —NR$^{10}$C(O)—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$—, and S(O)$_m$;
Z$^1$ is selected from unsubstituted or substituted phenyl and unsubstituted or substituted naphthyl, wherein the substituted phenyl or substituted naphthyl is substituted with one or more of:
  1) C$_{1-8}$ alkyl, C$_{2-8}$ alkenyl or C$_{2-8}$ alkynyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^4$,
    g) —C(O)NR$^6$R$^7$,
    h) —Si(C$_{1-4}$ alkyl)$_3$, or
    i) C$_{1-4}$ perfluoroalkyl;
  2) substituted or unsubstituted aryl or substituted or unsubstituted heterocycle,
  3) halogen,
  4) OR$^6$,
  5) NR$^6$R$^7$,
  6) CN,
  7) NO$_2$,
  8) CF$_3$,
  9) —S(O)$_m$R$^4$,
  10) —OS(O)$_2$R$^4$,
  11) —C(O)NR$^6$R$^7$,
  12) —C(O)OR$^6$, or
  13) C$_3$–C$_6$ cycloalkyl;
m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;

$C_6$–$C_{10}$ multicyclic ring is selected from:

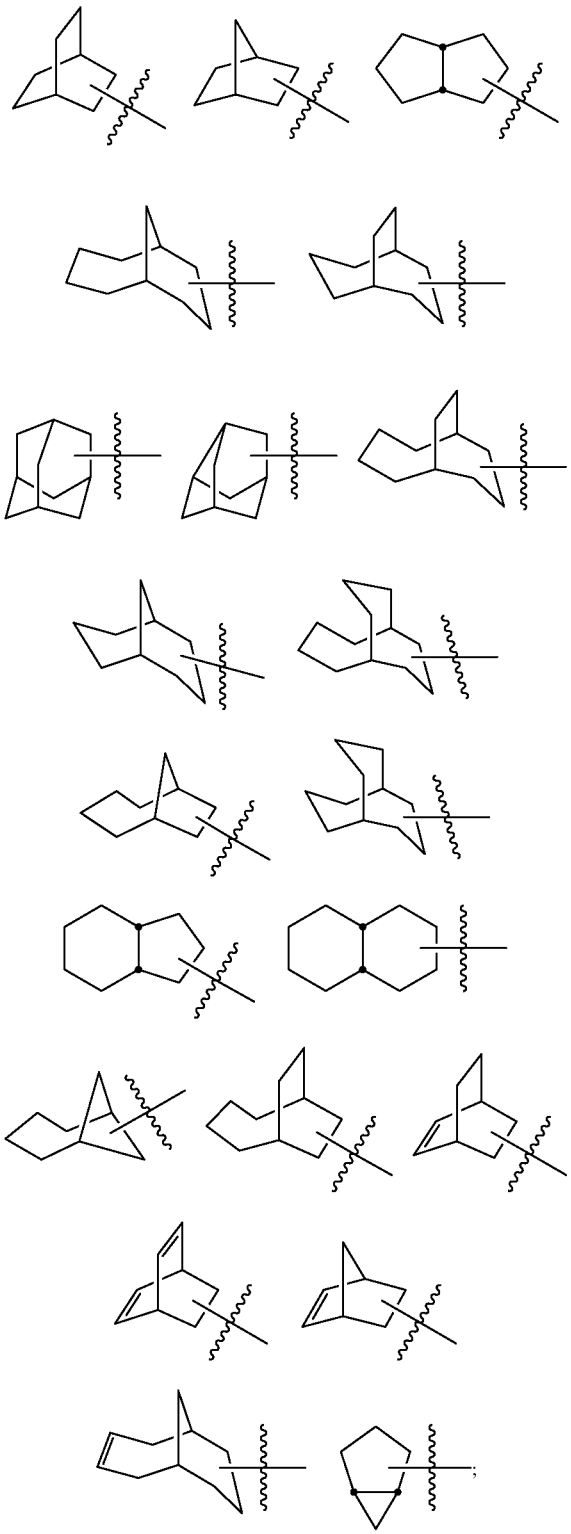

or a pharmaceutically acceptable salt or stereoisomer thereof.

4. The compound according to claim 3 of the formula C-1:

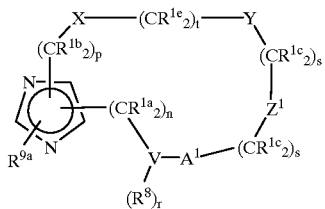

C-1 wherein:

$R^{1a}$, $R^{1b}$ and $R^{1c}$ are independently selected from:
  a) hydrogen,
  b) aryl, heterocycle, cycloalkyl, $R^{10}O$—, —$N(R^{10})_2$ or $C_2$–$C_6$ alkenyl, and
  c) $C_1$–$C_6$ alkyl unsubstituted or substituted by aryl, heterocycle, cycloalkyl, alkenyl, $R^{10}O$—, or —$N(R^{10})_2$;

$R^{1e}$ is independently selected from:
  a) hydrogen,
  b) unsubstituted or substituted aryl, unsubstituted or substituted heterocycle, cycloalkyl, alkenyl, alkynyl, $R^{10}O$—, $R^{11}S(O)_m$—, $R^{10}C(O)NR^{10}$—, $(R^{10})_2N$—C(O)—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
  c) unsubstituted or substituted $C_1$–$C_6$ alkyl wherein the substitutent on the substituted $C_1$–$C_6$ alkyl is selected from unsubstituted or substituted aryl, heterocyclic, cycloalkyl, alkenyl, alkynyl, perfluoroalkyl, halogen, $R^{10}O$—, $R^4S(O)_m$—, $R^4S(O)_2NR^{10}$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

or two $R^{1e}$s, on the same carbon atom may be combined to form —$(CH_2)_v$—;

$R^4$ is selected from $C_{1-4}$ alkyl and $C_{3-6}$ cycloalkyl, unsubstituted or substituted with:
  a) $C_{1-4}$ alkoxy,
  b) halogen, or
  c) aryl or heterocycle;

$R^6$ and $R^7$ are independently selected from H; $C_{1-6}$ alkyl, $C_{3-6}$ cycloalkyl, $C_6$–$C_{10}$ multicyclic ring, heterocycle, aryl, aroyl, heteroaroyl, arylsulfonyl, heteroarylsulfonyl, unsubstituted or substituted with one or two:
  a) $C_{1-4}$ alkoxy,
  b) aryl or heterocycle,
  c) halogen,
  d) HO,
  e) 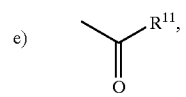
  f) —$SO_2R^{11}$,
  g) $N(R^{10})_2$, h) $C_{3-6}$ cycloalkyl,
i) $C_6$–$C_{10}$ multicyclic ring; or $R^8$ is independently selected from:
  a) hydrogen,
  b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by unsubstituted or substituted aryl, $C_1$–$C_6$ perfluoroalkyl, $R^{10}O$—, $R^{10}C(O)NR^{10}$—, $(R^{10})N$—$CN(R^{10})$—, $R^{10}C(O)$—, —$N(R^{10})_2$, or $R^{11}OC(O)NR^{10}$—;

$R^{9a}$ is hydrogen or methyl;

$R^{10}$ is independently selected from hydrogen, $C_1$–$C_6$ allyl, unsubstituted or substituted benzyl and unsubstituted or substituted aryl;

$R^{11}$ is independently selected from $C_1$–$C_6$ alkyl and unsubstituted or substituted aryl;

$R^{12}$ is independently selected from hydrogen, $C_1$–$C_6$ alkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is selected from a bond and O;

V is phenyl;

X and Y are independently selected from —C(O)—, —C(O)$NR^{10}$—, —$NR^{10}C(O)$—, —$NR^{10}C(O)NR^{10}$—, —C(O)$NR^{10}C(O)$—, O, —$N(R^{10})$—, —$S(O)_2N(R^{10})$—, —$N(R^{10})S(O)_2$—, and $S(O)_m$;

$Z^1$ is selected from unsubstituted or substituted phenyl and unsubstituted or substituted naphthyl, wherein the substituted phenyl or substituted naphthyl is substituted with one or more of:
  1) $C_{1-8}$ alkyl, $C_{2-8}$ alkenyl or $C_{2-8}$ alkynyl, unsubstituted or substituted with:
    a) $C_{1-4}$ alkoxy,
    b) $NR^6R^7$,
    c) $C_{3-6}$ cycloalkyl,
    d) aryl or heterocycle,
    e) HO,
    f) —$S(O)_mR^4$,
    g) —$C(O)NR^6R^7$,
    h) —$Si(C_{1-4}$ alkyl)3, or
    i) $C_{1-4}$ perfluoroalkyl;
  2) substituted or unsubstituted aryl or substituted or unsubstituted heterocycle,
  3) halogen,
  4) $OR^6$,
  5) $NR^6R^7$,
  6) CN,
  7) $NO_2$,
  8) $CF_3$,
  9) —$S(O)_mR^4$,
  10) —$OS(O)_2R^4$,
  11) —$C(O)NR^6R^7$,
  12) —$C(O)OR^6$, or
  13) $C_3$–$C_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;

$C_6$–$C_{10}$ multicyclic ring is selected from:

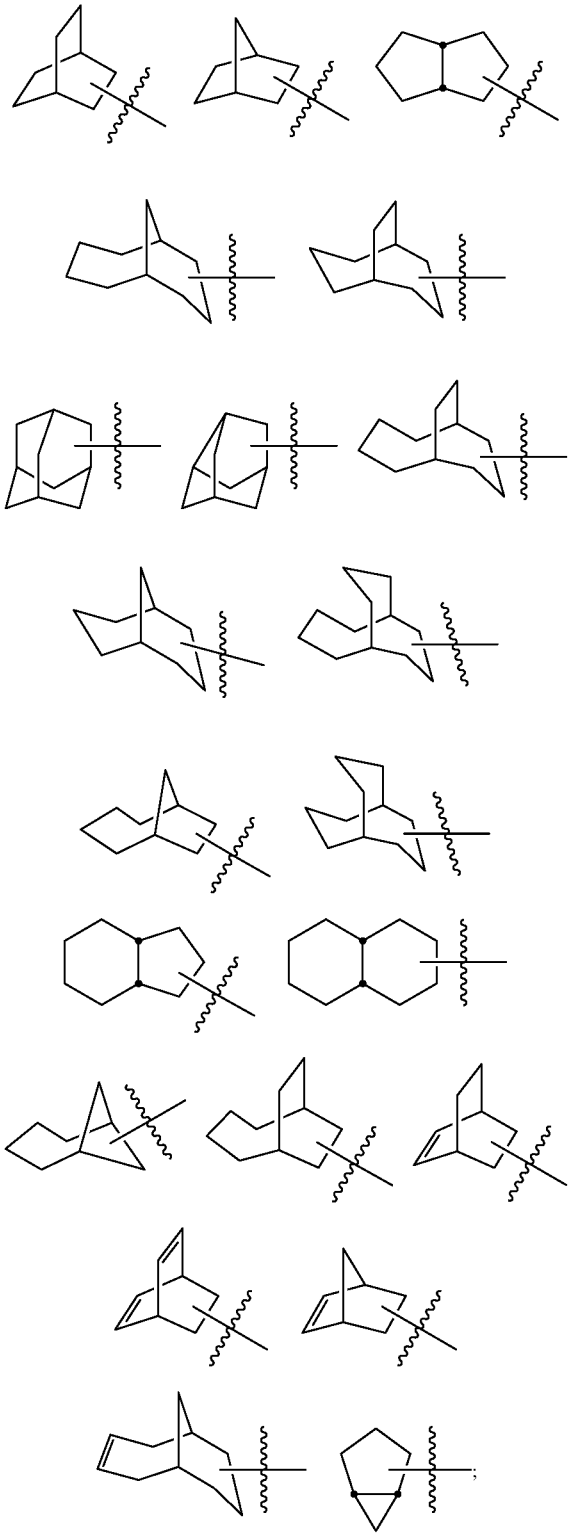

or a pharmaceutically acceptable salt or stereoisomer thereof.

5. The compound according to claim 4 of the formula D:

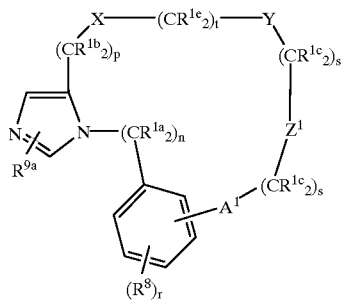

wherein:
R$^{1a}$, R$^{1b}$ and R$^{1c}$ are independently selected from:
a) hydrogen,
b) aryl, heterocycle, cycloalkyl, R$^{10}$O—, —N(R$^{10}$)$_2$ or C$_2$–C$_6$ alkenyl, and
c) C$_1$–C$_6$ alkyl unsubstituted or substituted by aryl, heterocycle, cycloalkyl, alkenyl, R$^{10}$O—, or —N(R$^{10}$)$_2$;

R$^{1e}$ is independently selected from:
a) hydrogen,
b) aryl, heterocycle, cycloalkyl, alkenyl, alkynyl, R$^{10}$O—, R$^{11}$S(O)$_m$—, R$^{10}$C(O)NR$^{10}$—, (R$^{10}$)$_2$N—C(O)—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—,
c) unsubstituted or substituted C$_1$–C$_6$ alkyl wherein the substitutent on the substituted C$_1$–C$_6$ alkyl is selected from unsubstituted or substituted aryl, heterocyclic, cycloalkyl, alkenyl, alkynyl, R$^{10}$O—, R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—;

R$^4$ is selected from C$_{1-4}$ alkyl and C$_{3-6}$ cycloalkyl, unsubstituted or substituted with:
a) C$_{1-4}$ alkoxy,
b) halogen, or
c) aryl or heterocycle;

R$^6$ and R$^7$ are independently selected from:
a) hydrogen,
b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—, and
c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

R$^8$ is independently selected from:
a) hydrogen,
b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^{12}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) C$_1$–C$_6$ alkyl substituted by unsubstituted or substituted aryl, C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^{9a}$ is hydrogen or methyl;

R$^{10}$ and R$^{12}$ are independently selected from hydrogen, C$_1$–C$_6$ alkyl, unsubstituted or substituted benzyl and unsubstituted or substituted aryl;

R$^{11}$ is independently selected from C$_1$–C$_6$ alkyl and unsubstituted or substituted aryl;

A$^1$ is selected from a bond and O;

X and Y are independently selected from —C(O)—, —C(O)NR$^{10}$—, —NR$^{10}$C(O)—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$—, and S(O)$_m$;

Z$^1$ is selected from unsubstituted or substituted phenyl or unsubstituted or substituted naphthyl, wherein the substituted phenyl or substituted naphthyl is substituted with one or two of:
1) C$_{1-4}$ alkyl, unsubstituted or substituted with:
   a) C$_{1-4}$ alkoxy,
   b) NR$^6$R$^7$,
   c) C$_{3-6}$ cycloalkyl,
   d) aryl or heterocycle,
   e) HO,
   f) —S(O)$_m$R$^4$, or
   g) —C(O)NR$^6$R$^7$,
2) aryl or heterocycle,
3) halogen,
4) OR$^6$,
5) NR$^6$R$^7$,
6) CN,
7) NO$_2$,
8) CF$_3$,
9) —S(O)$_m$R$^4$,
10) —C(O)NR$^6$R$^7$, or
11) C$_3$–C$_6$ cycloalkyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3 or 4;

or a pharmaceutically acceptable salt or stereoisomer thereof.

6. The compound according to claim 4 of the formula E:

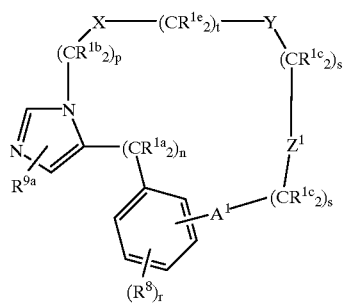

wherein:
R$^{1a}$, R$^{1b}$ and R$^{1c}$ are independently selected from:
a) hydrogen,
b) aryl, heterocycle, cycloalkyl, R$^{10}$O—, —N(R$^{10}$)$_2$ or C$_2$–C$_6$ alkenyl, and
c) C$_1$–C$_6$ alkyl unsubstituted or substituted by aryl, heterocycle, cycloalkyl, alkenyl, R$^{10}$O—, or —N(R$^{10}$)$_2$;

R$^{1e}$ is independently selected from:
a) hydrogen,
b) aryl, heterocycle, cycloalkyl, alkenyl, alkynyl, R$^{10}$O—, R$^{11}$S(O)$_m$—, R$^{10}$C(O)NR$^{10}$—, (R$^{10}$)$_2$N—

C(O)—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, c) unsubstituted or substituted C$_1$–C$_6$ alkyl wherein the substitutent on the substituted C$_1$–C$_6$ alkyl is selected from unsubstituted or substituted aryl, heterocyclic, cycloalkyl, alkenyl, alkynyl, R$^{10}$O—, R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—;

R$^4$ is selected from C$_{1-4}$ alkyl and C$_{3-6}$ cycloalkyl, unsubstituted or substituted with:
a) C$_{1-4}$ alkoxy,
b) halogen, or
c) aryl or heterocycle, R$^6$ and R$^7$ are independently selected from H; C$_{1-6}$ alkyl, C$_{3-6}$ cycloalkyl, C$_6$–C$_{10}$ multicyclic ring, aryl, aroyl, arylsulfonyl, unsubstituted or substituted with one or two:
a) C$_{1-4}$ alkoxy,
b) aryl,
c) halogen,
d) HO, e) 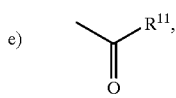

f) —SO$_2$R$^{11}$,
g) N(R$^{10}$)$_2$,
h) C$_{3-6}$ cycloalkyl,
i) C$_6$–C$_{10}$ multicyclic ring; or R$^8$ is independently selected from:
a) hydrogen,
b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^{12}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) C$_1$–C$_6$ alkyl substituted by unsubstituted or substituted aryl, C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^{9a}$ is hydrogen or methyl;

R$^{10}$ and R$^{12}$ are independently selected from hydrogen, C$_1$–C$_6$ alkyl, unsubstituted or substituted benzyl and unsubstituted or substituted aryl;

R$^{11}$ is independently selected from C$_1$–C$_6$ alkyl and unsubstituted or substituted aryl;

A$^1$ is selected from a bond and O;

X and Y are independently selected from —C(O)—, —C(O)NR$^{10}$—, —NR$^{10}$C(O)—, —NR$^{10}$C(O)NR$^{10}$—, —C(O)NR$^{10}$C(O)—, O, —N(R$^{10}$)—, —S(O)$_2$N(R$^{10}$)—, —N(R$^{10}$)S(O)$_2$—, and S(O)$_m$;

Z$^1$ is selected from unsubstituted or substituted phenyl or unsubstituted or substituted naphthyl, wherein the substituted phenyl or substituted naphthyl is substituted with one or two of:
1) C$_{1-8}$ alkyl, C$_{2-8}$ alkenyl or C$_{2-8}$ alkynyl, unsubstituted or substituted with:
a) C$_{1-4}$ alkoxy,
b) NR$^6$R$^7$,
c) C$_{3-6}$ cycloalkyl,
d) aryl or heterocycle,
e) HO,
f) —S(O)$_m$R$^4$,
g) —C(O)NR$^6$R$^7$,
h) —Si(C$_{1-4}$ alkyl)$_3$, or
i) C$_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) C$_3$–C$_6$ cycloalkyl;

m is 0, 1 or 2;

n is 0, 1, 2, 3 or 4;

p is 0, 1, 2, 3 or 4; provided p is 2, 3 or 4 when X is: —NR$^{10}$C(O)—, —NR$^{10}$C(O)NR$^{10}$—, O, —N(R$^{10}$)— or N(R$^{10}$)S(O)$_2$—;

r is 0 to 5;

s is independently 0, 1, 2 or 3; and t is 1, 2, 3 or 4;

C$_6$–C$_{10}$ multicyclic ring is selected from:

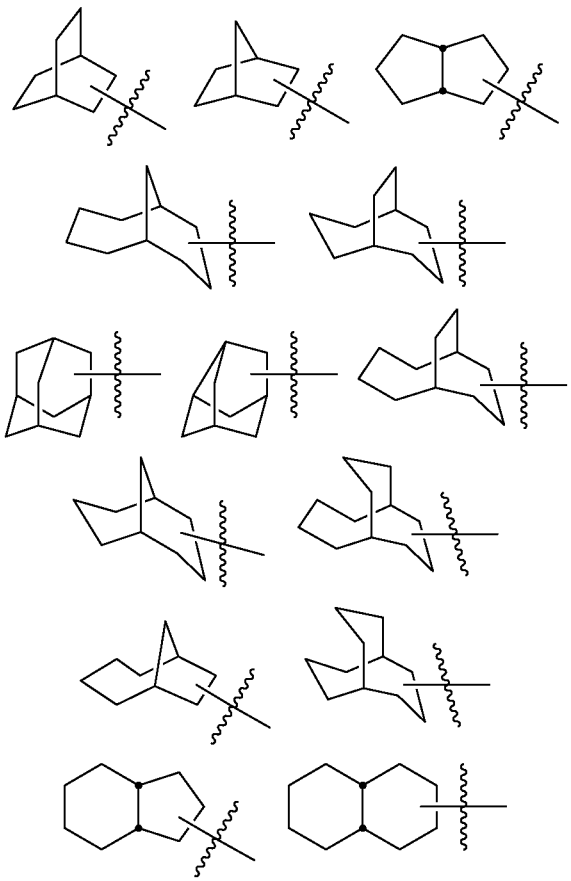

-continued

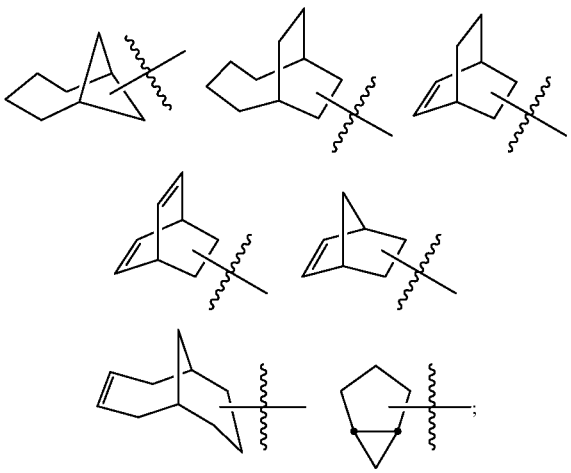

or a pharmaceutically acceptable salt or stereoisomer thereof.

7. A compound which is selected from:

20-n-Butyl-17,18,19,20-tetrahydro-17-[2,4-dimethoxybenzyl]-18-oxo-5H-6,10:12,16-dimetheno-21H-imidazo[4,3-1][1,7,10,13]oxatriazacyclononadecosine-9-carbonitrile (Compound 1)

20-n-Butyl-17,18,19,20-tetrahydro-18-oxo-5H-6,10:12,16-dimetheno-21H-imidazo[4,3-1][1,7,10,13]oxatriazacyclononadecosine-9-carbonitrile, (Compound 2)

20-n-Butyl-17,18,19,20-tetrahydro-18-oxo-17-[3-(trifluoromethyl)phenyl]-5H-6,10:12,16-dimetheno-21H-imidazo[4,3-1][1,7,10,13]oxatriazacyclononadecosine-9-carbonitrile (Compound 3)

19,20,21,22-Tetrahydro-19-oxo-5H-12,14-etheno-6,10-metheno-18H-benz[d]imidazo[4,3-k][1,6,9,12]oxatriazacyclooctadecosine-9-carbonitrile 19,20,21,22-Tetrahydro-19-oxo-17H-6,10:12,16-dimetheno-16H-imidazo[3,4-h][1,8,11,14]oxatriazacycloeicosine-9-carbonitrile (20R)-19,20,21,22-Tetrahydro-20-methyl-19-oxo-5H-12,14-etheno-6,10-metheno-18H-benz[d]imidazo[4,3-k][1,6,9,12]oxatriazacyclooctadecosine-9-carbonitrile (20S)-19,20,21,22-Tetrahydro-20-methyl-19-oxo-5H-12,14-etheno-6,10-metheno-18H-benz[d]imidazo[4,3-k][1,6,9,12]oxatriazacyclooctadecosine-9-carbonitrile (20R)-20-Benzyl-19,20,21,22-tetrahydro-19-oxo-5H-12,14-etheno-6,10-metheno-18H-benz[d]imidazo[4,3-k][1,6,9,12]oxatriazacyclooctadecosine-9-carbonitrile (20S)-20-Benzyl-19,20,21,22-tetrahydro-19-oxo-5H-12,14-etheno-6,10-metheno-18H-benz[d]imidazo[4,3-k][1,6,9,12]oxatriazacyclooctadecosine-9-carbonitrile (20R)-19,20,21,22-Tetrahydro-19-oxo-20-(3-pyridylmethyl)-5H-12,14-etheno-6,10-metheno-18H-benz[d]imidazo[4,3-k][1,6,9,12]oxatriazacyclooctadecosine-9-carbonitrile (20R)-19,20,21,22-Tetrahydro-19-oxo-20-(thiophen-2-ylmethyl)-5H-12,14-etheno-6,10-metheno-18H-benz[d]imidazo[4,3-k][1,6,9,12]oxatriazacyclooctadecosine-9-carbonitrile (20R)-19,20,22,23-Tetrahydro-20-methyl-19,22-dioxo-5H,21H-12,14-etheno-6,10-methenobenz[d]imidazo[4,3-1][1,6,9,13]oxatriazacyclononadecosine-9-carbonitrile (20R)-20-Benzyl-19,20,22,23-tetrahydro-19,22-dioxo-5H,21H-12,14-etheno-6,10-methenobenz[d]imidazo[4,3-1][1,6,9,13]oxatriazacyclononadecosine-9-carbonitrile (20R)-19,20,21,22-Tetrahydro-18,20-dimethyl-19-oxo-5H-12,14-etheno-6,10-metheno-18H-benz[d]imidazo[4,3-k][1,6,9,12]oxatriazacyclooctadecosine-9-carbonitrile (20S)-19,20,21,22-Tetrahydro-18,20-dimethyl-19-oxo-5H-12,14-etheno-6,10-metheno-18H-benz[d]imidazo[4,3-k][1,6,9,12]oxatriazacyclooctadecosine-9-carbonitrile 19,20,21,22-Tetrahydro-18-methyl-19-oxo-5H-12,14-etheno-6,10-metheno-18H-benz[d]imidazo[4,3-k][1,6,9,12]oxatriazacyclooctadecosine-9-carbonitrile 19,20,21,22-Tetrahydro-18,21-dimethyl-19-oxo-5H-12,14-etheno-6,10-metheno-18H-benz[d]imidazo[4,3-k][1,6,9,12]oxatriazacyclooctadecosine-9-carbonitrile (20R)-19,20,21,22-Tetrahydro-18,20,21-trimethyl-19-oxo-5H-12,14-etheno-6,10-metheno-18H-benz[d]imidazo[4,3-k][1,6,9,12]oxatriazacyclooctadecosine-9-carbonitrile (20S)-19,20,21,22-Tetrahydro-18,20,21-trimethyl-19-oxo-5H-12,14-etheno-6,10-metheno-18H-benz[d]imidazo[4,3-k][1,6,9,12]oxatriazacyclooctadecosine-9-carbonitrile 19,20,21,22-Tetrahydro-21-methyl-19-oxo-5H-12,14-etheno-6,10-metheno-18H-benz[d]imidazo[4,3-k][1,6,9,12]oxatriazacyclooctadecosine-9-carbonitrile (20R)-19,20,21,22-Tetrahydro-20,21-dimethyl-19-oxo-5H-12,14-etheno-6,10-metheno-18H-benz[d]imidazo[4,3-k][1,6,9,12]oxatriazacyclooctadecosine-9-carbonitrile (20S)-19,20,21,22-Tetrahydro-20,21-dimethyl-19-oxo-5H-12,14-etheno-6,10-metheno-18H-benz[d]imidazo[4,3-k][1,6,9,12]oxatriazacyclooctadecosine-9-carbonitrile 19,20,21,22-Tetrahydro-21-methyl-19-oxo-17H-6,10:12,16-dimetheno-16H-imidazo[3,4-h][1,8,11,14]oxatriazacycloeicosine-9-carbonitrile (20R)-20-Benzyl-19,20,21,22-tetrahydro-21-methyl-19-oxo-5H-12,14-etheno-6,10-metheno-18H-benz[d]imidazo[4,3-k][1,6,9,12]oxatriazacyclooctadecosine-9-carbonitrile (20S)-20-Benzyl-19,20,21,22-tetrahydro-21-methyl-19-oxo-5H-12,14-etheno-6,10-metheno-18H-benz[d]imidazo[4,3-k][1,6,9,12]oxatriazacyclooctadecosine-9-carbonitrile (20R)-20,21-Dibenzyl-19,20,21,22-tetrahydro-19-oxo-5H-12,14-etheno-6,10-metheno-18H-benz[d]imidazo[4,3-k][1,6,9,12]oxatriazacyclooctadecosine-9-carbonitrile (20S)-20,21-Dibenzyl-19,20,21,22-tetrahydro-19-oxo-5H-12,14-etheno-6,10-metheno-18H-benz[d]imidazo[4,3-k][1,6,9,12]oxatriazacyclooctadecosine-9-carbonitrile 21-Benzyl-19,20,21,22-tetrahydro-19-oxo-5H-12,14-etheno-6,10-metheno-18H-benz[d]imidazo[4,3-k][1,6,9,12]oxatriazacyclooctadecosine-9-carbonitrile (20R)-21-Benzyl-19,20,21,22-tetrahydro-20-methyl-19-oxo-5H-12,14-etheno-6,10-metheno-18H-benz[d]imidazo[4,3-k][1,6,9,12]oxatriazacyclooctadecosine-9-carbonitrile 18,19,20,21,22,23-Hexahydro-18-oxo-5H-12,14-etheno-6,10-methenobenz[d]imidazo[4,3-1][1,7,10,13]oxatriazacyclononadecosine-9-carbonitrile 18,19,20,21,22,23-Hexahydro-18,21-dioxo-5H-12,14-etheno-6,10-methenobenz[d]imidazo[4,3-l][1,7,10,13]oxatriazacyclononadecosine-9-carbonitrile 19,20,21,22,23,24-Hexahydro-18,23-dioxo-5H-12,14-etheno-6,10-18H-methenobenz[d]imidazo[4,3-m][1,7,10,14]oxatriazacycloeicosine-9-carbonitrile or a pharmaceutically acceptable salt, optical isomer or stereoisomer thereof.

8. The compound according to claim 7 which is

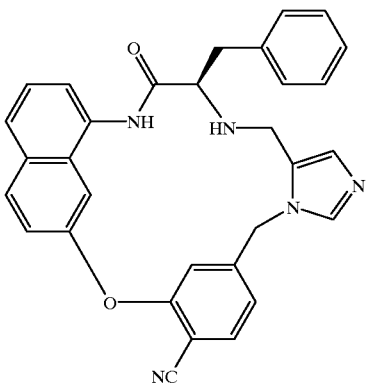

(20R)-20-Benzyl-19,20,21,22-tetrahydro-19-oxo-5H-12,14-etheno-6,10-metheno-18H-benz[d]imidazo[4,3-k][1,6,9,12]oxatriazacyclooctadecosine-9-carbonitrile or a pharmaceutically acceptable salt, optical isomer or stereoisomer thereof.

9. The compound according to claim 7 which is

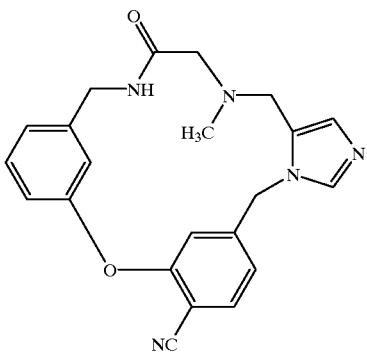

19,20,21,22-Tetrahydro-21-methyl-19-oxo-17H-6,10:12,16-dimetheno-16H-imidazo[3,4-h][1,8,11,14]oxatriazacycloeicosine-9-carbonitrile or a pharmaceutically acceptable salt, optical isomer or stereoisomer thereof.

10. The compound according to claim 7 which is

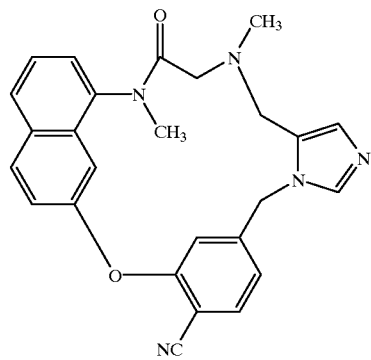

19,20,21,22-Tetrahydro-18,21-dimethyl-19-oxo-5H-12,14-etheno-6,10-metheno-18H-benz[d]imidazo[4,3-k][1,6,9,12]oxatriazacyclooctadecosine-9-carbonitrile or a pharmaceutically acceptable salt, optical isomer or stereoisomer thereof.

11. The compound according to claim 7 which is

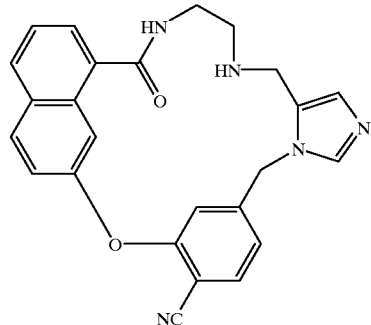

18,19,20,21,22,23-Hexahydro-18-oxo-5H-12,14-etheno-6,10-methenobenz[d]imidazo[4,3-l][1,7,10,13]oxatriazacyclononadecosine-9-carbonitrile or a pharmaceutically acceptable salt, optical isomer or stereoisomer thereof.

12. A pharmaceutical composition comprising a pharmaceutical carrier, and dispersed therein, a therapeutically effective amount of a compound of claim 1.

13. A pharmaceutical composition comprising a pharmaceutical carrier, and dispersed therein, a therapeutically effective amount of a compound of claim 4.

14. A pharmaceutical composition comprising a pharmaceutical carrier, and dispersed therein, a therapeutically effective amount of a compound of claim 6.

15. A pharmaceutical composition comprising a pharmaceutical carrier, and dispersed therein, a therapeutically effective amount of a compound of claim 7.

16. A method for treating blindness related to retinal vascularization which comprises administering to a mammal in need thereof a therapeutically effective amount of a composition of claim 12.

17. A method for treating infections from hepatitis delta and related viruses which comprises administering to a mammal in need thereof a therapeutically effective amount of a composition of claim 12.

18. A method for preventing restenosis which comprises administering to a mammal in need thereof a therapeutically effective amount of a composition of claim 12.

19. A method for treating polycystic kidney disease which comprises administering to a mammal in need thereof a therapeutically effective amount of a composition of claim 12.

20. A pharmaceutical composition made by combining the compound of claim 1 and a pharmaceutically acceptable carrier.

21. A process for making a pharmaceutical composition comprising combining a compound of claim 1 and a pharmaceutically acceptable carrier.

22. A method for treating cancer related to a mutation in the ras gene which comprises administering to a mammal in need thereof a therapeutically effective amount of a composition of claim 12.

23. A method for treating cancer related to a mutation in the ras gene which comprises administering to a mammal in need thereof a therapeutically effective amount of a composition of claim 13.

24. A method for treating cancer related to a mutation in the ras gene which comprises administering to a mammal in need thereof a therapeutically effective amount of a composition of claim 14.

25. A method of conferring radiation sensitivity on a tumor cell of a cancer related to a mutation in the ras gene which comprises administering a therapeutically effective amount of a composition of claim 12 in combination with radiation therapy.

* * * * *

SEQUENCE LISTING

<160> NUMBER OF SEQ ID NOS: 25

<210> SEQ ID NO 1
<211> LENGTH: 4
<212> TYPE: PRT
<213> ORGANISM: Artificial Sequence
<220> FEATURE:
<223> OTHER INFORMATION: completely synthetic sequence

```
<400> SEQUENCE: 1

Cys Val Leu Leu
  1

<210> SEQ ID NO 2
<211> LENGTH: 4
<212> TYPE: PRT
<213> ORGANISM: Artificial Sequence
<220> FEATURE:
<223> OTHER INFORMATION: completely synthetic sequence

<400> SEQUENCE: 2

Cys Val Leu Ser
  1

<210> SEQ ID NO 3
<211> LENGTH: 15
<212> TYPE: PRT
<213> ORGANISM: Artificial Sequence
<220> FEATURE:
<223> OTHER INFORMATION: completely synthetic sequence

<400> SEQUENCE: 3

Gly Lys Lys Lys Lys Lys Ser Lys Thr Lys Cys Val Ile Met
  1               5                  10                  15

<210> SEQ ID NO 4
<211> LENGTH: 52
<212> TYPE: DNA
<213> ORGANISM: Artificial Sequence
<220> FEATURE:
<223> OTHER INFORMATION: completely synthetic sequence

<400> SEQUENCE: 4
gagagggaat tcgggccctt cctgcatgct gctgctgctg ctgctgctgg gc        52

<210> SEQ ID NO 5
<211> LENGTH: 41
<212> TYPE: DNA
<213> ORGANISM: Artificial Sequence
<220> FEATURE:
<223> OTHER INFORMATION: completely synthetic sequence

<400> SEQUENCE: 5
gagagagctc gaggttaacc cgggtgcgcg gcgtcggtgg t                    41

<210> SEQ ID NO 6
<211> LENGTH: 42
<212> TYPE: DNA
<213> ORGANISM: Artificial Sequence
<220> FEATURE:
<223> OTHER INFORMATION: completely synthetic sequence

<400> SEQUENCE: 6
gagagagtct agagttaacc cgtggtcccc gcgttgcttc ct                   42

<210> SEQ ID NO 7
<211> LENGTH: 43
<212> TYPE: DNA
<213> ORGANISM: Artificial Sequence
<220> FEATURE:
<223> OTHER INFORMATION: completely synthetic sequence

<400> SEQUENCE: 7
gaagaggaag cttggtaccg ccactgggct gtaggtggtg gct                  43
```

```
<210> SEQ ID NO 8
<211> LENGTH: 27
<212> TYPE: DNA
<213> ORGANISM: Artificial Sequence
<220> FEATURE:
<223> OTHER INFORMATION: completely synthetic sequence

<400> SEQUENCE: 8
ggcagagctc gtttagtgaa ccgtcag                                27

<210> SEQ ID NO 9
<211> LENGTH: 27
<212> TYPE: DNA
<213> ORGANISM: Artificial Sequence
<220> FEATURE:
<223> OTHER INFORMATION: completely synthetic sequence

<400> SEQUENCE: 9
gagagatctc aaggacggtg actgcag                                27

<210> SEQ ID NO 10
<211> LENGTH: 86
<212> TYPE: DNA
<213> ORGANISM: Artificial Sequence
<220> FEATURE:
<223> OTHER INFORMATION: completely synthetic sequence

<400> SEQUENCE: 10
tctcctcgag gccaccatgg ggagtagcaa gagcaagcct aaggacccca gccagcgccg   60
gatgacagaa tacaagcttg tggtgg                                 86

<210> SEQ ID NO 11
<211> LENGTH: 33
<212> TYPE: DNA
<213> ORGANISM: Artificial Sequence
<220> FEATURE:
<223> OTHER INFORMATION: completely synthetic sequence

<400> SEQUENCE: 11
cacatctaga tcaggacagc acagacttgc agc                         33

<210> SEQ ID NO 12
<211> LENGTH: 41
<212> TYPE: DNA
<213> ORGANISM: Artificial Sequence
<220> FEATURE:
<223> OTHER INFORMATION: completely synthetic sequence

<400> SEQUENCE: 12
tctcctcgag gccaccatga cagaatacaa gcttgtggtg g                41

<210> SEQ ID NO 13
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 13
cactctagac tggtgtcaga gcagcacaca cttgcagc                    38

<210> SEQ ID NO 14
<211> LENGTH: 38
<212> TYPE: DNA
```

```
<213> ORGANISM: Artificial Sequence
<220> FEATURE:
<223> OTHER INFORMATION: completely synthetic sequence

<400> SEQUENCE: 14
gagagaattc gccaccatga cggaatataa gctggtgg                          38

<210> SEQ ID NO 15
<211> LENGTH: 33
<212> TYPE: DNA
<213> ORGANISM: Artificial Sequence
<220> FEATURE:
<223> OTHER INFORMATION: completely synthetic sequence

<400> SEQUENCE: 15
gagagtcgac gcgtcaggag agcacacact tgc                               33

<210> SEQ ID NO 16
<211> LENGTH: 22
<212> TYPE: DNA
<213> ORGANISM: Artificial Sequence
<220> FEATURE:
<223> OTHER INFORMATION: completely synthetic sequence

<400> SEQUENCE: 16
ccgccggcct ggaggagtac ag                                           22

<210> SEQ ID NO 17
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 17
gagagaattc gccaccatga ctgagtacaa actggtgg                          38

<210> SEQ ID NO 18
<211> LENGTH: 32
<212> TYPE: DNA
<213> ORGANISM: Artificial Sequence
<220> FEATURE:
<223> OTHER INFORMATION: completely synthetic sequence

<400> SEQUENCE: 18
gagagtcgac ttgttacatc accacacatg gc                                32

<210> SEQ ID NO 19
<211> LENGTH: 21
<212> TYPE: DNA
<213> ORGANISM: Artificial Sequence
<220> FEATURE:
<223> OTHER INFORMATION: completely synthetic sequence

<400> SEQUENCE: 19
gttggagcag ttggtgttgg g                                            21

<210> SEQ ID NO 20
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 20
gagaggtacc gccaccatga ctgaatataa acttgtgg                          38
```

```
<210> SEQ ID NO 21
<211> LENGTH: 36
<212> TYPE: DNA
<213> ORGANISM: Artificial Sequence
<220> FEATURE:
<223> OTHER INFORMATION: completely synthetic sequence

<400> SEQUENCE: 21
ctctgtcgac gtatttacat aattacacac tttgtc                         36

<210> SEQ ID NO 22
<211> LENGTH: 24
<212> TYPE: DNA
<213> ORGANISM: Artificial Sequence
<220> FEATURE:
<223> OTHER INFORMATION: completely synthetic sequence

<400> SEQUENCE: 22
gtagttggag ctgttggcgt aggc                                      24

<210> SEQ ID NO 23
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 23
gagaggtacc gccaccatga ctgaatataa acttgtgg                       38

<210> SEQ ID NO 24
<211> LENGTH: 45
<212> TYPE: DNA
<213> ORGANISM: Artificial Sequence
<220> FEATURE:
<223> OTHER INFORMATION: completely synthetic sequence

<400> SEQUENCE: 24
ctctgtcgac agattacatt ataatgcatt ttttaatttt cacac               45

<210> SEQ ID NO 25
<211> LENGTH: 24
<212> TYPE: DNA
<213> ORGANISM: Artificial Sequence
<220> FEATURE:
<223> OTHER INFORMATION: completely synthetic sequence

<400> SEQUENCE: 25
gtagttggag ctgttggcgt aggc                                      24
```